United States Patent
DiNardo et al.

(12)

(10) Patent No.: US 11,096,694 B2
(45) Date of Patent: Aug. 24, 2021

(54) FIRING ASSEMBLY FOR CIRCULAR STAPLER

(71) Applicant: Ethicon LLC, Guaynabo, PR (US)

(72) Inventors: Brian F. DiNardo, Cincinnati, OH (US); Charles J. Scheib, Loveland, OH (US)

(73) Assignee: Cilag GmbH International, Zug (CH)

( * ) Notice: Subject to any disclaimer, the term of this patent is extended or adjusted under 35 U.S.C. 154(b) by 124 days.

(21) Appl. No.: 16/291,055

(22) Filed: Mar. 4, 2019

(65) Prior Publication Data

US 2019/0274688 A1 Sep. 12, 2019

Related U.S. Application Data

(63) Continuation of application No. 14/751,486, filed on Jun. 26, 2015, now Pat. No. 10,226,253.

(51) Int. Cl.
*A61B 17/068* (2006.01)
*A61B 17/115* (2006.01)
(Continued)

(52) U.S. Cl.
CPC ........ *A61B 17/1155* (2013.01); *A61B 17/068* (2013.01); *A61B 17/105* (2013.01);
(Continued)

(58) Field of Classification Search
CPC .............. A61B 17/1155; A61B 17/068; A61B 2017/2903; A61B 2017/2912
See application file for complete search history.

(56) References Cited

U.S. PATENT DOCUMENTS

| 5,205,459 A | 4/1993 | Brinkerhoff et al. |
| 5,271,544 A | 12/1993 | Fox et al. |

(Continued)

FOREIGN PATENT DOCUMENTS

| CN | 104224254 A | 2/2014 |
| EP | 2 851 013 A1 | 3/2015 |

(Continued)

OTHER PUBLICATIONS

European Search Report and Written Opinion dated Oct. 25, 2016 for Application No. 16176150.7, 7 pages.
(Continued)

*Primary Examiner* — Andrew M Tecco
(74) *Attorney, Agent, or Firm* — Frost Brown Todd LLC

(57) ABSTRACT

A surgical instrument includes a body, a shaft assembly, a stapling head assembly, and a drive assembly. The shaft assembly includes an actuator. The stapling head assembly is operable to drive an annularly arranged array of staples into tissue in response to translation of the actuator along a first axis relative to the body. The drive assembly is operable to translate the actuator along the first axis. The drive assembly comprises first and second rotary members. The first rotary member is rotatable about a second axis. The second axis is non-parallel with the first axis. The second rotary member is rotatable about a third axis. The third axis is non-parallel with the first axis and non-parallel with the second axis. The first rotary member is operable to drive the second rotary member to rotate about the third axis to thereby drive the actuator along the first axis.

14 Claims, 43 Drawing Sheets

(51) Int. Cl.
*A61B 17/10* (2006.01)
*A61B 17/00* (2006.01)
*A61B 17/29* (2006.01)

(52) U.S. Cl.
CPC .............. *A61B 2017/00398* (2013.01); *A61B 2017/291* (2013.01); *A61B 2017/2903* (2013.01); *A61B 2017/2912* (2013.01); *A61B 2017/2923* (2013.01); *A61B 2017/2925* (2013.01)

(56) References Cited

U.S. PATENT DOCUMENTS

| | | | |
|---|---|---|---|
| 5,275,322 A | 1/1994 | Brinkerhoff et al. | |
| 5,285,945 A | 2/1994 | Brinkerhoff et al. | |
| 5,292,053 A | 3/1994 | Bilotti et al. | |
| 5,333,773 A | 8/1994 | Main et al. | |
| 5,350,104 A | 9/1994 | Main et al. | |
| 5,467,911 A * | 11/1995 | Tsuruta ............... | A61B 17/0682 227/175.1 |
| 5,533,661 A | 7/1996 | Main et al. | |
| 5,628,446 A * | 5/1997 | Geiste ................. | A61B 17/0684 227/175.1 |
| 6,945,444 B2 | 9/2005 | Gresham et al. | |
| 7,461,767 B2 | 12/2008 | Viola et al. | |
| 7,794,475 B2 | 9/2010 | Hess et al. | |
| 8,025,199 B2 * | 9/2011 | Whitman ........... | A61B 17/1155 227/179.1 |
| 8,408,439 B2 | 4/2013 | Huang et al. | |
| 8,453,914 B2 | 6/2013 | Laurent et al. | |
| 8,910,847 B2 | 12/2014 | Nalagatla et al. | |
| 9,060,760 B2 | 6/2015 | Sullivan et al. | |
| 9,161,803 B2 | 10/2015 | Yates et al. | |
| 10,226,253 B2 | 3/2019 | DiNardo et al. | |
| 2003/0050639 A1 | 3/2003 | Yachia et al. | |
| 2006/0278681 A1 | 12/2006 | Viola et al. | |
| 2008/0255413 A1 | 10/2008 | Zemlok et al. | |
| 2008/0255420 A1 | 10/2008 | Lee et al. | |
| 2009/0270898 A1 | 10/2009 | Chin et al. | |
| 2011/0290853 A1 | 12/2011 | Shelton, IV et al. | |
| 2012/0104071 A1 * | 5/2012 | Bryant ................. | A61B 17/068 227/175.1 |
| 2014/0144968 A1 | 5/2014 | Shelton | |
| 2014/0144969 A1 | 5/2014 | Scheib et al. | |
| 2014/0151429 A1 | 6/2014 | Scheib et al. | |
| 2014/0151430 A1 | 6/2014 | Scheib et al. | |
| 2014/0158747 A1 | 6/2014 | Measamer et al. | |
| 2014/0166717 A1 | 6/2014 | Swayze et al. | |
| 2014/0166718 A1 | 6/2014 | Swayze et al. | |
| 2014/0166728 A1 | 6/2014 | Swayze et al. | |
| 2015/0083772 A1 * | 3/2015 | Miller ................. | A61B 17/1155 227/175.1 |
| 2015/0083773 A1 * | 3/2015 | Measamer ........... | A61B 17/068 227/175.1 |
| 2015/0083774 A1 | 3/2015 | Measamer et al. | |
| 2015/0083775 A1 * | 3/2015 | Leimbach .......... | A61B 17/1155 227/175.1 |

FOREIGN PATENT DOCUMENTS

| | | |
|---|---|---|
| WO | WO 2006/132292 A2 | 12/2006 |
| WO | WO 2008/123936 A1 | 10/2008 |

OTHER PUBLICATIONS

International Search Report and Written Opinion dated Oct. 10, 2016 for International Application No. PCT/US2016/038950, 12 pages.
Brazilian Office Action, dated May 28, 2020, for Application No. BR112017028084-1, 4 pages.
Chinese Office Action and Search Report, dated Mar. 5, 2020, for Application No. 201680037447.3, 9 pages.
Japanese Notification of Reasons for Refusal, dated Aug. 11, 2020, for Application No. 2017-567145, 4 pages.

* cited by examiner

FIRING ASSEMBLY FOR CIRCULAR STAPLER

This application is a continuation of U.S. application Ser. No. 14/751,486, filed Jun. 26, 2015, entitled "Firing Assembly for Circular Stapler," issued as U.S. Pat. No. 10,226,253 on Mar. 12, 2019.

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis. The end-to-end anastomosis may provide a substantially unobstructed flow path from one portion of the digestive tract to the other portion of the digestive tract, without also providing any kind of leaking at the site of the anastomosis.

One example of an instrument that may be used to provide an end-to-end anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015; U.S. Pub. No. 2015/0083773, entitled "Surgical Stapling Instrument with Drive Assembly Having Toggle Features," published Mar. 26, 2015, issued as U.S. Pat. No. 9,936,949 on Apr. 10, 2018; U.S. Pub. No. 2015/0083774, entitled "Control Features for Motorized Surgical Stapling Instrument," published Mar. 26, 2015 issued as U.S. Pat. No. 9,907,552 on Mar. 6, 2018; and U.S. Pub. No. 2015/0083775, entitled "Surgical Stapler with Rotary Cam Drive," published Mar. 26, 2015, issued as U.S. Pat. No. 9,713,469 on Jul. 25, 2017. The disclosure of each of the above-cited U.S. Patent Publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
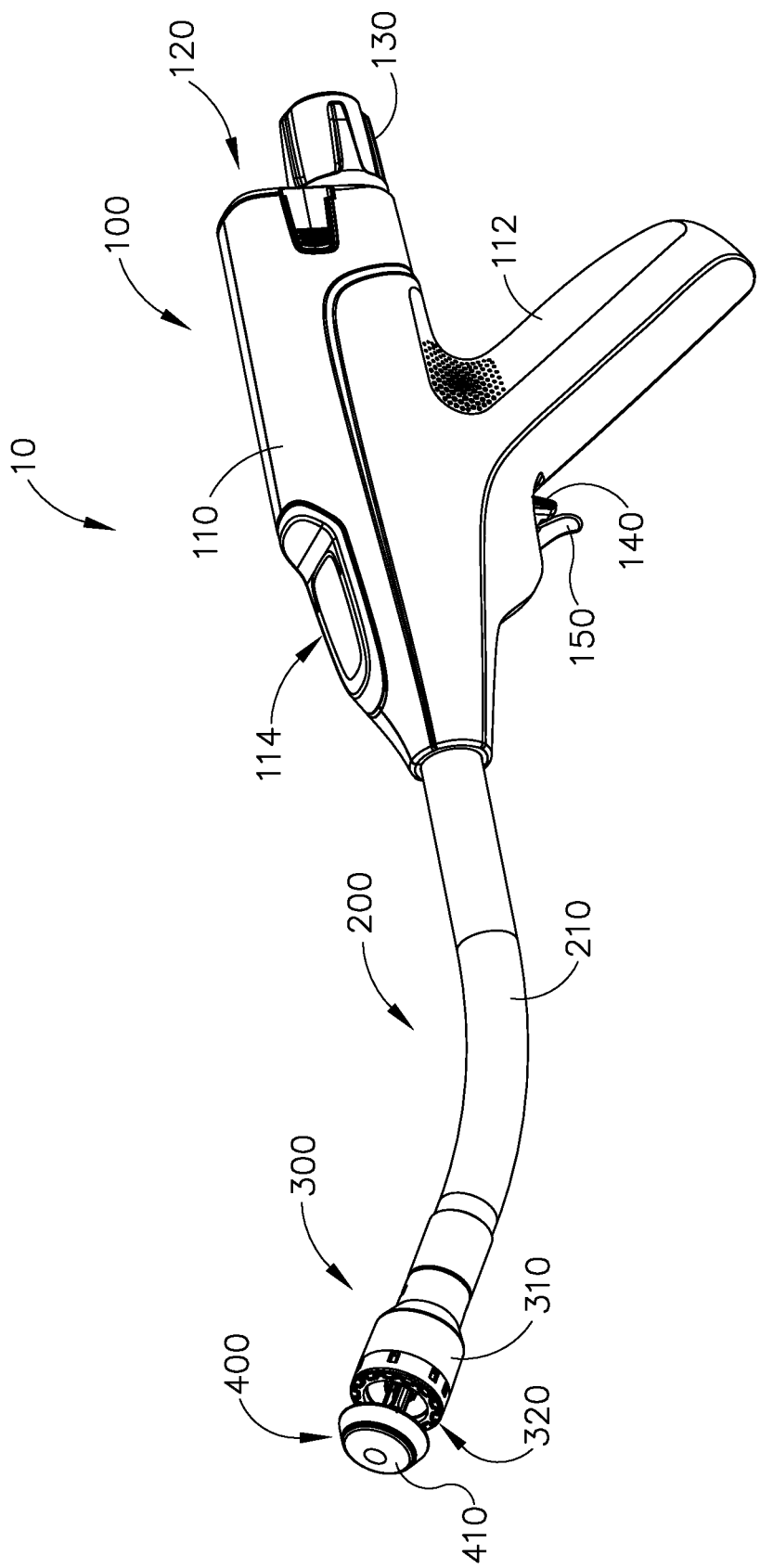
FIG. 1 depicts a perspective view of an exemplary circular stapler.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

Figure 2:
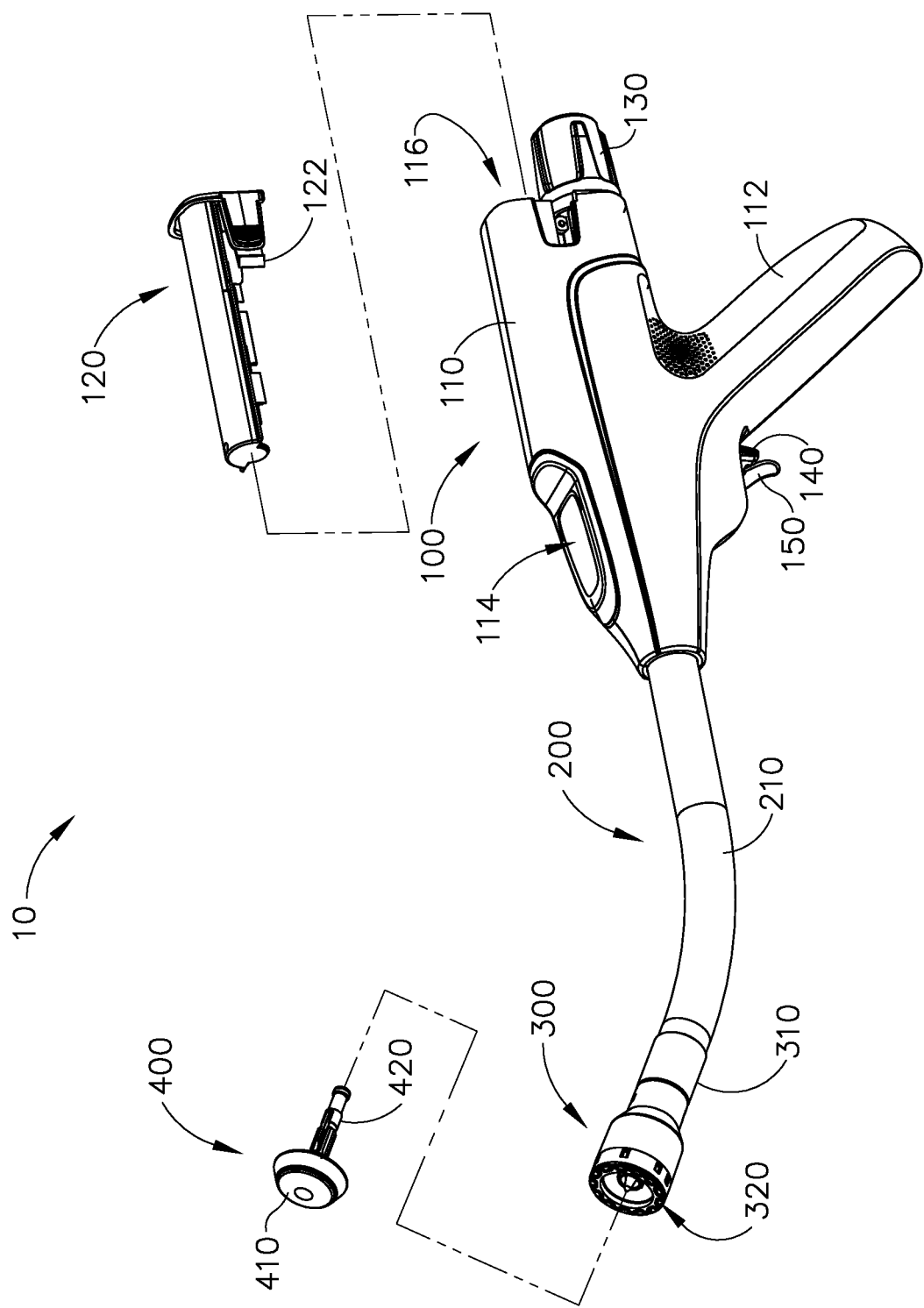
FIG. 2 depicts a perspective view of the circular stapler of FIG. 1, with a battery pack removed from a handle assembly and an anvil removed from a stapling head assembly.

FIGS. 1-2 depict an exemplary surgical circular stapling instrument (10) that may be used to provide an end-to-end anastomosis between two sections of an anatomical lumen such as a portion of a patient's digestive tract. Instrument (10) of this example comprises a handle assembly (100), a shaft assembly (200), a stapling head assembly (300), and an anvil (400). Handle assembly (100) comprises a casing (110) defining an obliquely oriented pistol grip (112). In some versions, pistol grip (112) is perpendicularly oriented. In some other versions, pistol grip (112) is omitted. Handle assembly (110) further includes a window (114) that permits viewing of a movable indicator needle (526) as will be described in greater detail below. In some versions, a series of hash marks, colored regions, and/or other fixed indicators are positioned adjacent to window (114) in order to provide a visual context for indicator needle (526), thereby facilitating operator evaluation of the position of needle (526) within window (114). Various suitable alternative features and configurations for handle assembly (112) will be apparent to those of ordinary skill in the art in view of the teachings herein.

Instrument (10) of the present example further includes a battery pack (120). Battery pack (120) is operable to provide electrical power to a motor (160) in pistol grip (112) as will be described in greater detail below. Battery pack (120) is removable from handle assembly (100). In particular, as shown in FIGS. 1-2, battery pack (120) may be inserted into a socket (116) defined by casing (110). Once battery pack (120) is fully inserted in socket (116), latches (122) of battery pack (120) may resiliently engage interior features of casing (110) to provide a snap fit. To remove battery pack (120), the operator may press latches (122) inwardly to disengage latches (122) from the interior features of casing (110) then pull battery pack (120) proximally from socket (116). It should be understood that battery pack (120) and handle assembly (100) may have complementary electrical contacts, pins and sockets, and/or other features that provide paths for electrical communication from battery pack (120) to electrically powered components in handle assembly (100) when battery pack (120) is inserted in socket (116). It should also be understood that, in some versions, battery pack (120) is unitarily incorporated within handle assembly (100) such that battery back (120) cannot be removed from handle assembly (100).

Shaft assembly (200) extends distally from handle assembly (100) and includes a preformed bend. In some versions, the preformed bend is configured to facilitate positioning of stapling head assembly (300) within a patient's colon. Various suitable bend angles or radii that may be used will be apparent to those of ordinary skill in the art in view of the teachings herein. In some other versions, shaft assembly (200) is straight, such that shaft assembly (200) lacks a preformed bend. Various exemplary components that may be incorporated into shaft assembly (100) will be described in greater detail below.

Stapling head assembly (300) is located at the distal end of shaft assembly (200). As shown in FIGS. 1-2 and as will be described in greater detail below, anvil (400) is configured to removably couple with shaft assembly (200), adjacent to stapling head assembly (300). As will also be described in greater detail below, anvil (400) and stapling head assembly (300) are configured to cooperate to manipulate tissue in three ways, including clamping the tissue, cutting the tissue, and stapling the tissue. A knob (130) at the proximal end of handle assembly (100) is rotatable relative to casing (110) to provide precise clamping of the tissue between anvil (400) and stapling head assembly (300). When a safety trigger (140) of handle assembly (100) is pivoted away from a firing trigger (150) of handle assembly (100), firing trigger (150) may be actuated to thereby provide cutting and stapling of the tissue.

A. Exemplary Anvil

In the following discussion of anvil (400), the terms "distal" and "proximal" (and variations thereof) will be used with reference to the orientation of anvil (400) when anvil (400) is coupled with shaft assembly (200) of instrument (10). Thus, proximal features of anvil (400) will be closer to the operator of instrument (10); while distal features of anvil (400) will be further from the operator of instrument (10).

Figure 3:
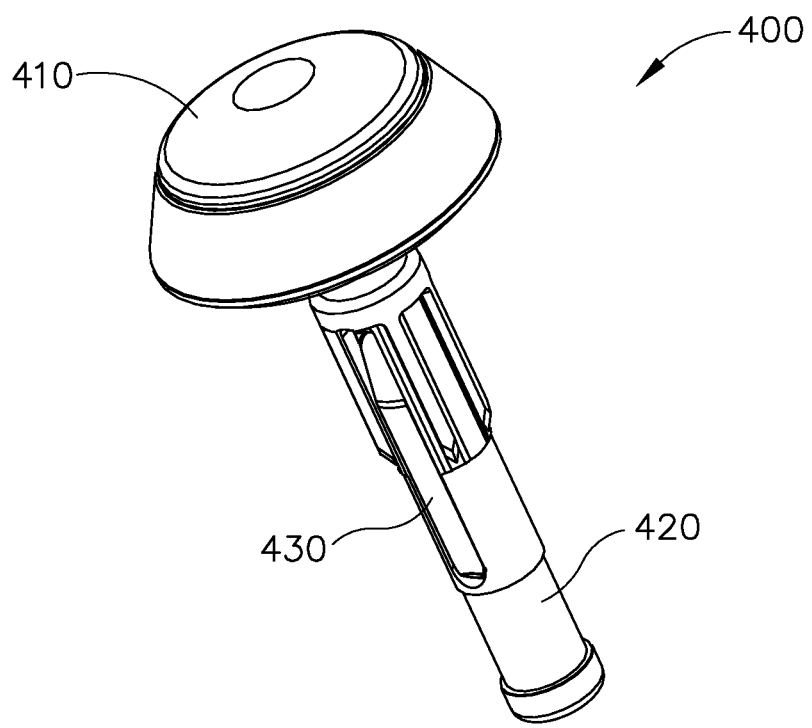
FIG. 3 depicts a perspective view of the anvil of the circular stapler of FIG. 1.
Figure 4:
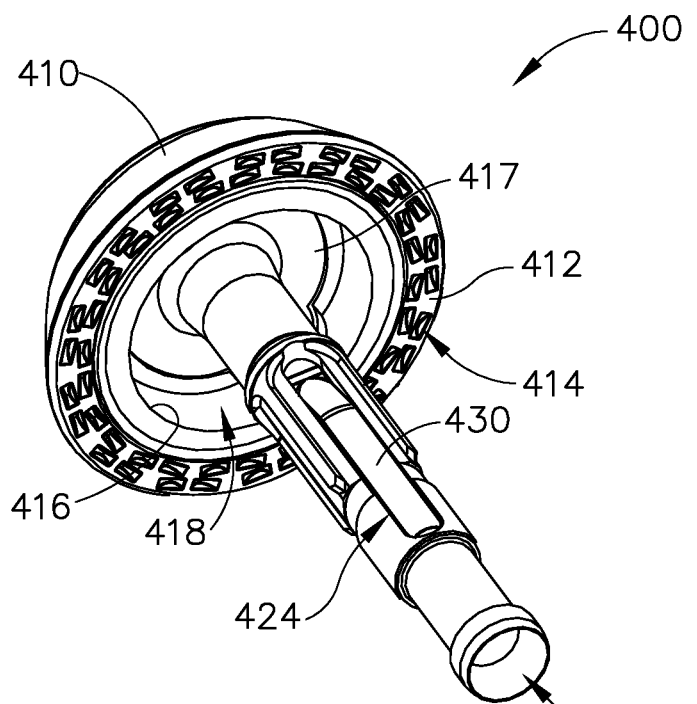
FIG. 4 depicts another perspective view of the anvil of FIG. 3.
Figure 5:
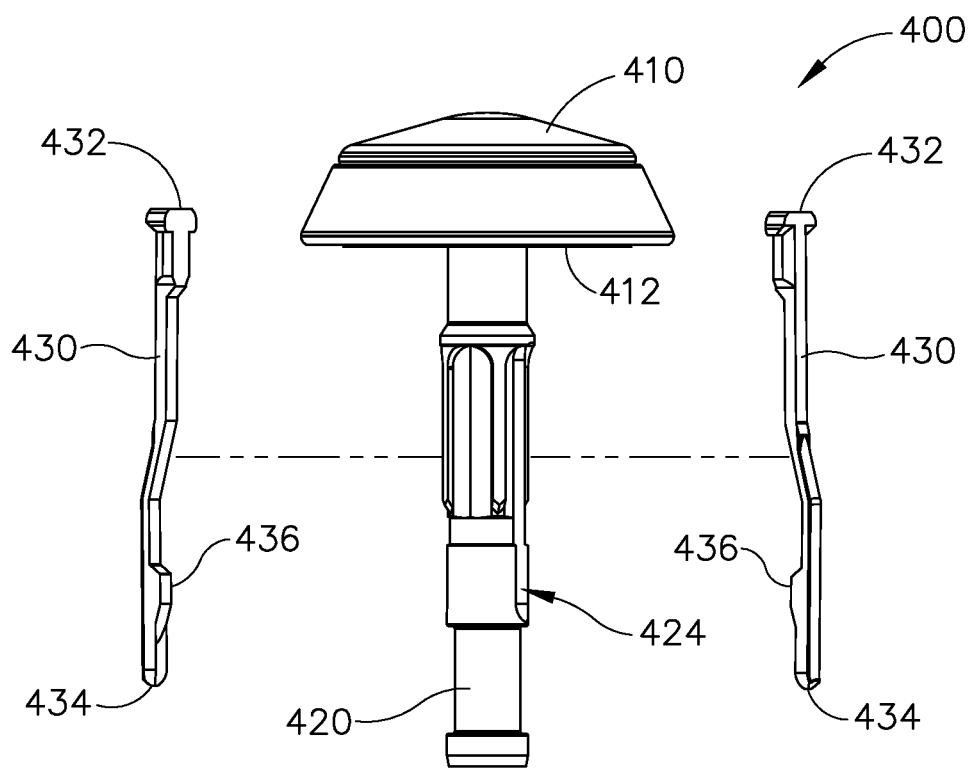
FIG. 5 depicts an exploded side elevational view of the anvil of FIG. 3.

As best seen in FIGS. 3-5, anvil (400) of the present example comprises a head (410) and a shank (420). Head (410) includes a proximal surface (412) that defines a plurality of staple forming pockets (414). Staple forming pockets (414) are arranged in two concentric annular arrays. In some other versions, staple forming pockets (414) are arranged in three or more concentric annular arrays. Staple forming pockets (414) are configured to deform staples as the staples are driven into staple forming pockets (414). For instance, each staple forming pocket (414) may deform a generally "U" shaped staple into a "B" shape as is known in the art. As best seen in FIG. 4, proximal surface (412) terminates at an inner edge (416), which defines an outer boundary of an annular recess (418) surrounding shank (420).

Shank (420) defines a bore (422) and includes a pair of pivoting latch members (430) positioned in bore (422). As best seen in FIG. 5, each latch member (430) includes a "T" shaped distal end (432), a rounded proximal end (434), and a latch shelf (436) located distal to proximal end (434). "T" shaped distal ends (432) secure latch members (430) within bore (422). Latch members (430) are positioned within bore (422) such that distal ends (434) are positioned at the proximal ends of lateral openings (424), which are formed through the sidewall of shank (420). Lateral openings (424) thus provide clearance for distal ends (434) and latch shelves (436) to deflect radially outwardly from the longitudinal axis defined by shank (420). However, latch members (430) are configured to resiliently bias distal ends (434) and latch shelves (436) to radially inwardly toward the longitudinal axis defined by shank (420). Latch members (430) thus act as retaining clips. This allows anvil (400) to be removably secured to a trocar (330) of stapling head assembly (300) as will be described in greater detail below. It should be understood, however, that latch members (436) are merely optional. Anvil (400) may be removably secured to a trocar (330) using any other suitable components, features, or techniques.

In addition to or in lieu of the foregoing, anvil (400) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or 8,910,847, the disclosures of which are incorporated by reference herein. Still other suitable configurations will be apparent to one of ordinary skill in the art in view of the teachings herein.

B. Exemplary Stapling Head Assembly

Figure 6:
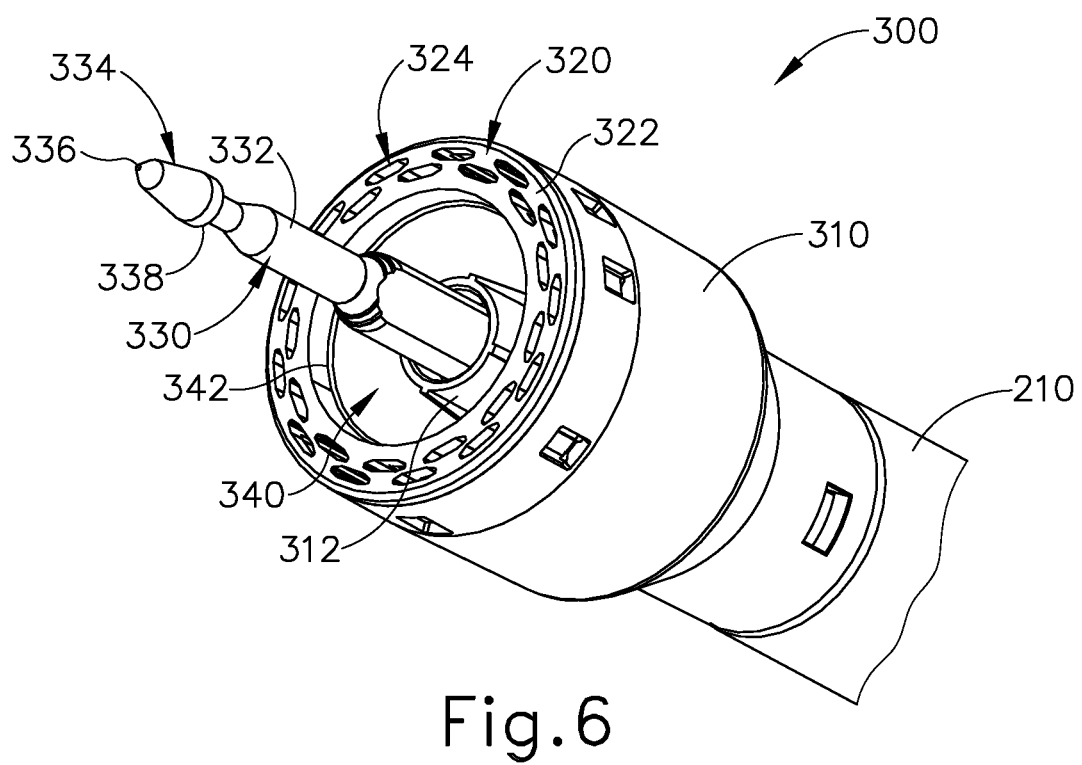
FIG. 6 depicts a perspective view of the stapling head assembly of the circular stapler of FIG. 1.
Figure 7:
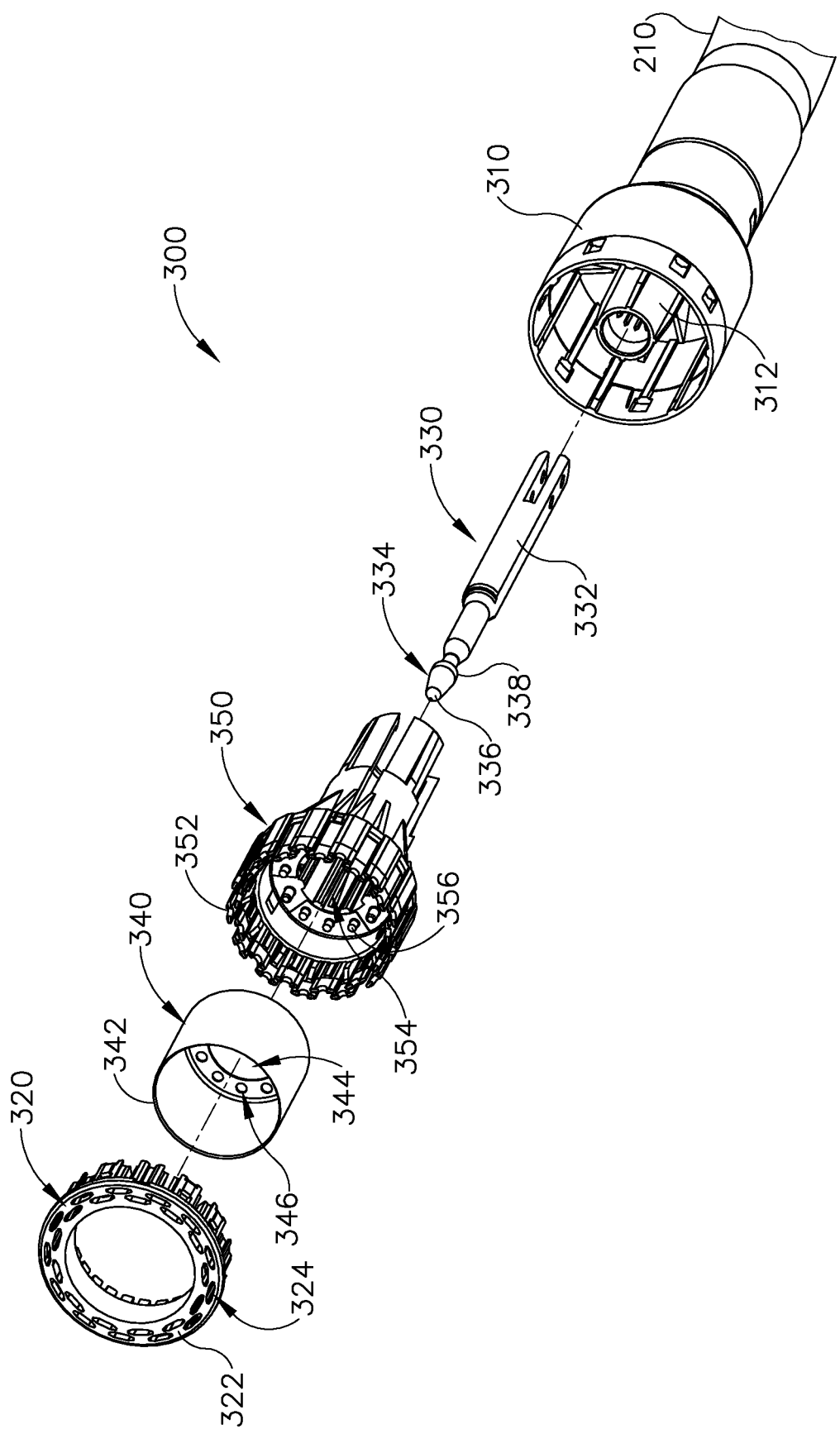
FIG. 7 depicts an exploded perspective view of the stapling head assembly of FIG. 6.

As best seen in FIGS. 6-7, stapling head assembly (300) of the present example is coupled to a distal end of shaft assembly (200) and comprises a tubular casing (310) housing a slidable staple driver member (350). A cylindraceous inner core member (312) extends distally within tubular casing (310). Tubular casing (310) is fixedly secured to an outer sheath (210) of shaft assembly (200), such that tubular casing (310) serves as a mechanical ground for stapling head assembly (300).

Trocar (330) is positioned coaxially within inner core member (312) of tubular casing (310). As will be described in greater detail below, trocar (330) is operable to translate distally and proximally relative to tubular casing (310) in response to rotation of knob (130) relative to casing (110) of handle assembly (100). Trocar (330) comprises a shaft (332) and a head (334). Head (334) includes a pointed tip (336) and an inwardly extending proximal surface (338). Shaft (332) thus provides a reduced outer diameter just proximal to head (334), with surface (338) providing a transition between that reduced outer diameter of shaft (332) and the outer diameter of head (334). While tip (336) is pointed in the present example, tip (336) is not sharp. Tip (336) will thus not easily cause trauma to tissue due to inadvertent contact with tissue. Head (334) and the distal portion of shaft (332) are configured for insertion in bore (422) of anvil (420). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit due to latch members (430).

Staple driver member (350) is operable to actuate longitudinally within tubular casing (310) in response to activation of motor (160) as will be described in greater detail below. Staple driver member (350) includes two distally presented concentric annular arrays of staple drivers (352). Staple drivers (352) are arranged to correspond with the arrangement of staple forming pockets (414) described above. Thus, each staple driver (352) is configured to drive a corresponding staple into a corresponding staple forming pocket (414) when stapling head assembly (300) is actuated. It should be understood that the arrangement of staple drivers (352) may be modified just like the arrangement of staple forming pockets (414) as described above. Staple driver member (350) also defines a bore (354) that is configured to coaxially receive core member (312) of tubular casing (310). An annular array of studs (356) project distally from a distally presented surface surrounding bore (354).

A cylindraceous knife member (340) is coaxially positioned within staple driver member (350). Knife member (340) includes a distally presented, sharp circular cutting edge (342). Knife member (340) is sized such that knife member (340) defines an outer diameter that is smaller than the diameter defined by the inner annular array of staple drivers (352). Knife member (340) also defines an opening that is configured to coaxially receive core member (312) of tubular casing (310). An annular array of openings (346) formed in knife member (340) is configured to complement the annular array of studs (356) of staple driver member (350), such that knife member (340) is fixedly secured to staple driver member (350) via studs (356) and openings (346). Other suitable structural relationships between knife member (340) and stapler driver member (350) will be apparent to those of ordinary skill in the art in view of the teachings herein.

A deck member (320) is fixedly secured to tubular casing (310). Deck member (320) includes a distally presented deck surface (322) defining two concentric annular arrays of staple openings (324). Staple openings (324) are arranged to correspond with the arrangement of staple drivers (352) and staple forming pockets (414) described above. Thus, each staple opening (324) is configured to provide a path for a corresponding staple driver (352) to drive a corresponding staple through deck member (320) and into a corresponding staple forming pocket (414) when stapling head assembly (300) is actuated. It should be understood that the arrangement of staple openings (322) may be modified just like the arrangement of staple forming pockets (414) as described above. It should also be understood that various structures and techniques may be used to contain staples within stapling head assembly (300) before stapling head assembly (300) is actuated. Such structures and techniques that are used to contain staples within stapling head assembly (300) may prevent the staples from inadvertently falling out through staple openings (324) before stapling head assembly (300) is actuated. Various suitable forms that such structures and techniques may take will be apparent to those of ordinary skill in the art in view of the teachings herein.

As best seen in FIG. 6, deck member (320) defines an inner diameter that is just slightly larger than the outer diameter defined by knife member (340). Deck member (320) is thus configured to allow knife member (340) to translate distally to a point where cutting edge (342) is distal to deck surface (322).

In addition to or in lieu of the foregoing, stapling head assembly (300) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or 8,910,847, the disclosures of which are incorporated by reference herein. Still other suitable configurations will be apparent to one of ordinary skill in the art in view of the teachings herein.

C. Exemplary Shaft Assembly

Figure 8:
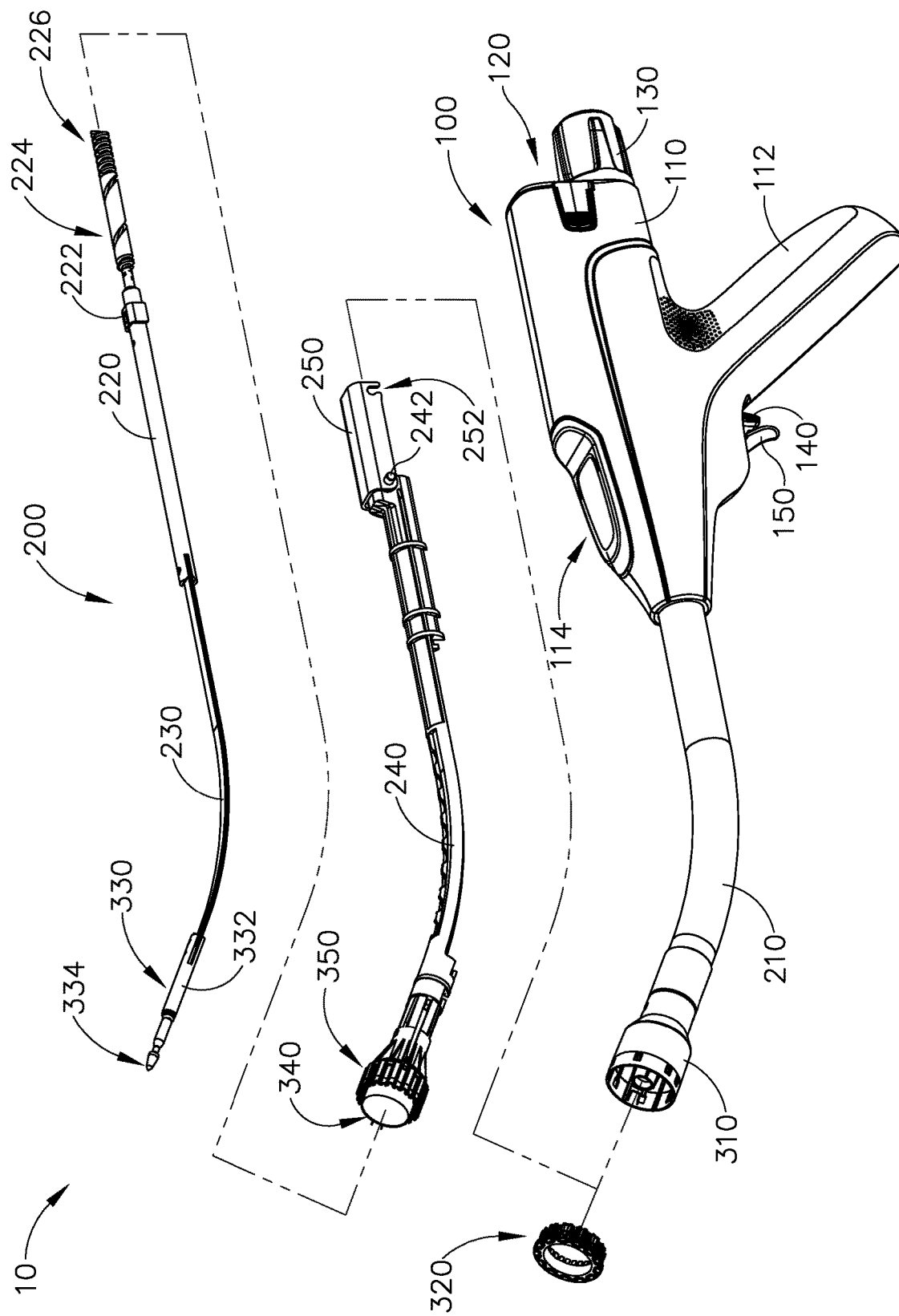
FIG. 8 depicts an exploded perspective view of the circular stapler of FIG. 1, with portions of the shaft assembly shown separately from each other.

FIG. 8 shows various components of shaft assembly (200), which couples components of stapling head assembly (300) with components of handle assembly (100). In particular, and as noted above, shaft assembly (200) includes an outer sheath (210) that extends between handle assembly (100) and tubular casing (310). In the present example, outer sheath (210) is rigid and includes a preformed curved section as noted above.

Shaft assembly (200) further includes a trocar actuation rod (220) and a trocar actuation band assembly (230). The distal end of trocar actuation band assembly (230) is fixedly secured to the proximal end of trocar shaft (332). The proximal end of trocar actuation band assembly (230) is fixedly secured to the distal end of trocar actuation rod (220). It should therefore be understood that trocar (330) will translate longitudinally relative to outer sheath (210) in response to translation of trocar actuation band assembly (230) and trocar actuation rod (220) relative to outer sheath (210). Trocar actuation band assembly (230) is configured to flex such that trocar actuation band assembly (230) may follow along the preformed curve in shaft assembly (200) as trocar actuation band assembly (230) is translated longitudinally relative to outer sheath (210). However, trocar actuation band assembly (230) has sufficient column strength and tensile strength to transfer distal and proximal forces from trocar actuation rod (220) to trocar shaft (332). Trocar actuation rod (220) is rigid. A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a coarse helical threading (224) and a fine helical threading (226). Details regarding the movement of trocar actuation rod (220) will be described in greater detail below.

Shaft assembly (200) further includes a stapling head assembly driver (240) that is slidably received within outer sheath (210). The distal end of stapling head assembly driver (240) is fixedly secured to the proximal end of staple driver member (350). The proximal end of stapling head assembly driver (240) is secured to a drive bracket (250) via a pin (242). It should therefore be understood that staple driver member (350) will translate longitudinally relative to outer sheath (210) in response to translation of stapling head assembly driver (240) and drive bracket (250) relative to outer sheath (210). Stapling head assembly driver (240) is configured to flex such that stapling head assembly driver (240) may follow along the preformed curve in shaft assembly (200) as stapling head assembly driver (240) is translated longitudinally relative to outer sheath (210). However, stapling head assembly driver (240) has sufficient column strength to transfer distal forces from drive bracket (250) to staple driver member (350). Details regarding the movement of drive bracket (250) will be described in greater detail below.

While not shown in FIG. 8, it should be understood that shaft assembly (200) may further include one or more spacer elements within outer sheath (210). Such spacer elements may be configured to support trocar actuation band assembly (230) and/or stapling head assembly driver (240) as trocar actuation band assembly (230) and/or stapling head assembly driver (240) translate through outer sheath (210). For instance, such spacer elements may prevent trocar actuation band assembly (230) and/or stapling head assembly driver (240) from buckling as trocar actuation band assembly (230) and/or stapling head assembly driver (240) translate through outer sheath (210). Various suitable forms that such spacer elements may take will be apparent to those of ordinary skill in the art in view of the teachings herein.

In addition to or in lieu of the foregoing, shaft assembly (200) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or 8,910,847, the disclosures of which are incorporated by reference herein. Still other suitable configurations will be apparent to one of ordinary skill in the art in view of the teachings herein.

D. Exemplary Actuator Handle Assembly

Figure 9:
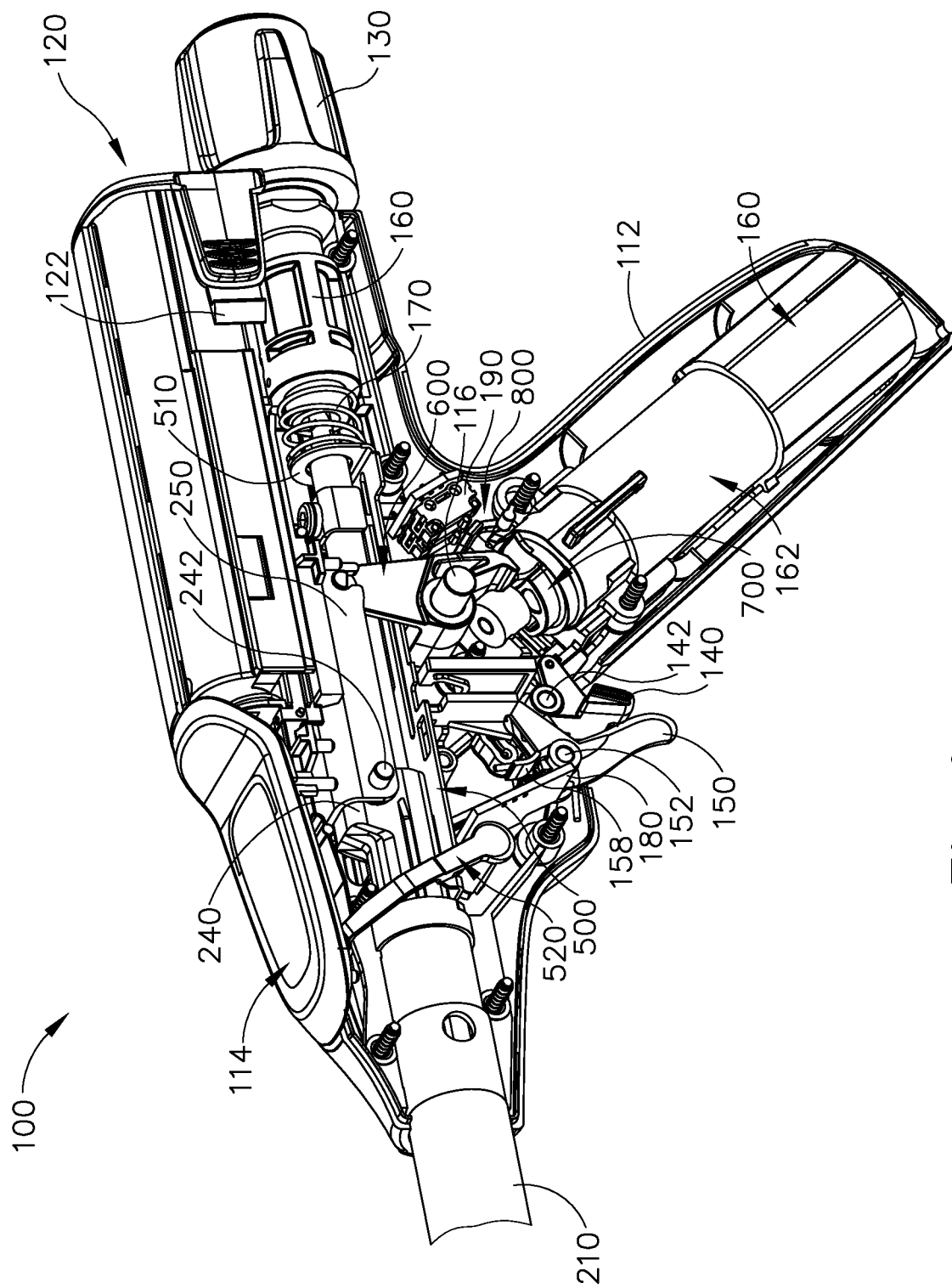
FIG. 9 depicts a perspective view of the handle assembly of the circular stapler of FIG. 1, with a housing half omitted to reveal internal components of the handle assembly.

As shown in FIG. 9, handle assembly (100) includes several components that are operable to actuate anvil (400) and stapling head assembly (300). Handle assembly (100) also includes components that are operable to selectively lock out triggers (140, 150) based on the position of anvil (400) relative to stapling head assembly (300). When triggers (140, 150) are locked out, firing trigger (150) is prevented from initiating actuation of stapling head assembly (300). Thus, trigger (150) is only operable to initiate actuation of stapling head assembly (300) when the position of anvil (400) relative to stapling head assembly (300) is within a predefined range. The components of handle assembly (100) that provide the foregoing operability will be described in greater detail below.

1. Exemplary Anvil Actuation Assembly

Knob (130) protrudes proximally from casing (110) of handle assembly and is rotatable relative to casing (110). As shown in FIG. 9, a nut (160) is secured to the distal end of knob (130). In the present example, nut (160) is fixedly secured to the distal end of knob (130) such that nut (160) will rotate unitarily with knob (130). Nut (160) and knob (130) are configured to cooperate with trocar actuation rod (220) to thereby translate trocar actuation rod (220) longitudinally relative to casing (110) in response to rotation of nut (160) and knob (130) relative to casing (110). As noted above, trocar (330) will translate longitudinally relative to outer sheath (210) in response to translation of trocar actuation rod (220) relative to outer sheath (210) and casing (110).

The proximal portion of trocar actuation rod (220) is positioned within handle assembly (100) to engage nut (160) and knob (130). In particular, trocar actuation rod (220) is positioned within handle assembly (100) such that coarse helical threading (224) will selectively engage a thread engagement feature (not shown) within the interior of nut (160); and such that fine helical threading (226) will selectively engage a thread engagement feature (not shown) within the interior of knob (130). In some versions, the thread engagement feature of nut (160) comprises an inwardly directed tab; while the thread engagement feature of knob (130) comprises a helical threading. Other suitable forms that such thread engagement features may take will be apparent to those of ordinary skill in the art in view of the teachings herein.

In the present example, when nut (160) and knob (130) are rotated relative to casing (110), trocar actuation rod (220) travels proximally through a first range of longitudinal motion where coarse helical threading (224) is engaged with nut (160) to provide a relatively rapid rate of translation. Fine helical threading (226) is not engaged with knob (130) during this range of motion. When nut (160) and knob (130) are further rotated relative to casing (110) after trocar actuation rod (220) completes the first range of motion, trocar actuation rod (220) will continue to travel proximally through a second range of longitudinal motion where fine helical threading (226) is engaged with knob (130) to provide a relatively slow rate of translation. Thus, trocar actuation rod (220) will translate proximally through a sequence of rapid translation followed by slow translation, based on engagement between coarse helical threading (224) and nut (160) followed by engagement between fine helical threading (226) and knob (130).

It should be understood that when anvil (400) is coupled with trocar (330), rotation of knob (130) will provide corresponding translation of anvil relative to stapling head assembly (300). It should also be understood that knob (130) may be rotated in a first angular direction (e.g., clockwise) to retract anvil (400) toward stapling head assembly (300); and in a second angular direction (e.g., counterclockwise) to advance anvil (400) away from stapling head assembly (300). Knob (130) may thus be used to adjust the gap distance (d) between opposing surfaces (412, 322) of anvil (400) and stapling head assembly (300) until a suitable gap distance (d) has been achieved as shown in FIG. 21C and as described in greater detail below.

2. Exemplary Trigger Lockout Assembly

As noted above, knob may be used to adjust the gap distance (d) between opposing surfaces (412, 322) of anvil (400) and stapling head assembly (300). Setting an appropriate gap distance (d) before actuating stapling head assembly (300) may be critical to the success of an anastomosis. For instance, if the gap distance (d) is too great, the staples that are deployed at the anastomosis site may not be sufficiently formed by staple forming pockets (414). This may result in leakage at the anastomosis site, and in some cases may ultimately lead to the separation of the anatomical lumen sections that are joined at the anastomosis site. If the gap distance (d) is too small, the internal structure of the tissue compressed between surfaces (412, 322) may be damaged to the point where the structural integrity of the tissue is compromised. This may prevent the tissue from adequately holding the formed staples, which again may result in leakage or other failure of the anastomosis. It may therefore be desirable to provide the operator with some form of feedback indicating whether the gap distance (d) is within an appropriate range. It may also be desirable to prevent the operator from actuating stapling head assembly (300) unless the gap distance (d) is within an appropriate range.

Figure 10:
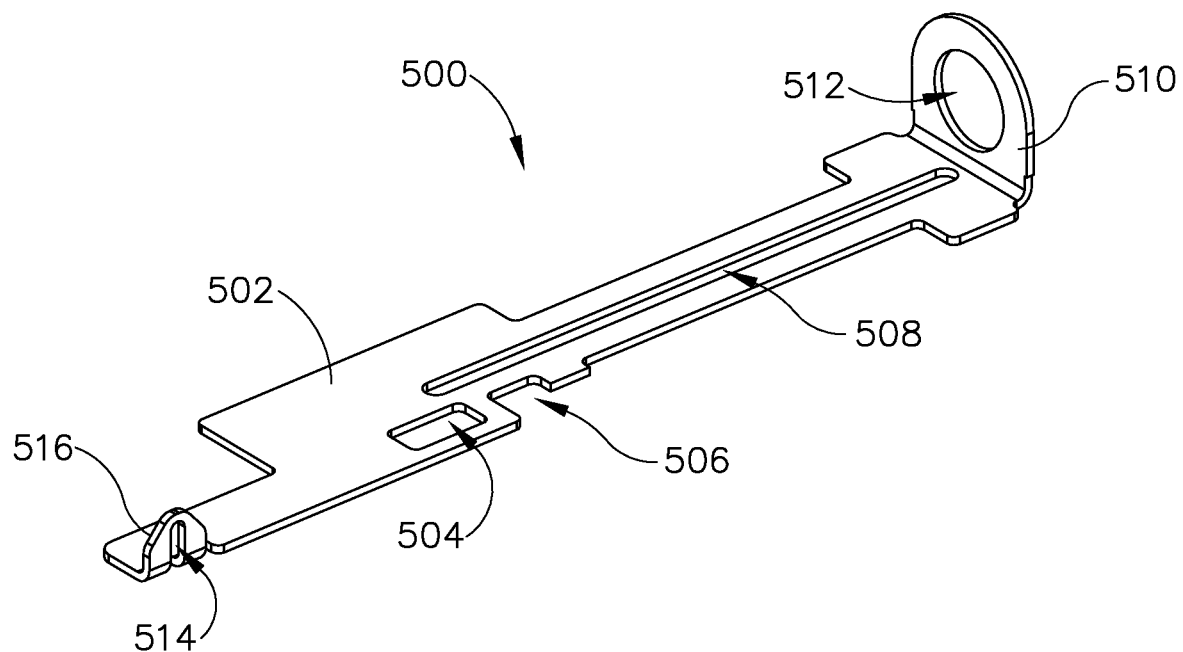
FIG. 10 depicts a perspective view of a bracket of the handle assembly of FIG. 9.

FIGS. 9-12E show components that provide feedback to the operator to indicate whether the gap distance (d) is within an appropriate range; and prevent the operator from actuating stapling head assembly (300) unless the gap distance (d) is within an appropriate range. As best seen in FIGS. 12B-12C, a bracket (500) is configured and positioned to move in response to movement of trocar actuation rod (220). As best seen in FIG. 10, bracket (500) includes a rigid body (502) that defines a first slot (504), a second slot (506), and a third slot (508). An upright feature (510) is positioned at the proximal end of body (502) and defines an opening (512). Trocar actuation rod (220) extends coaxially through opening (512). As shown in FIG. 9, a coil spring (170) is interposed between the proximal end of upright feature (510) and a rigid bulkhead feature that is defined by casing (110) and that forms a support journal for nut (160). The bulkhead is fixed within casing (110) and thereby provides a ground for the proximal end of coil spring (170), such that coil spring (170) resiliently imparts a distal bias to bracket (500) via upright feature (510). Bracket (500) further includes a laterally presented flange (516) at the distal end of body (502). Flange (516) defines a slot (514).

Figure 11:
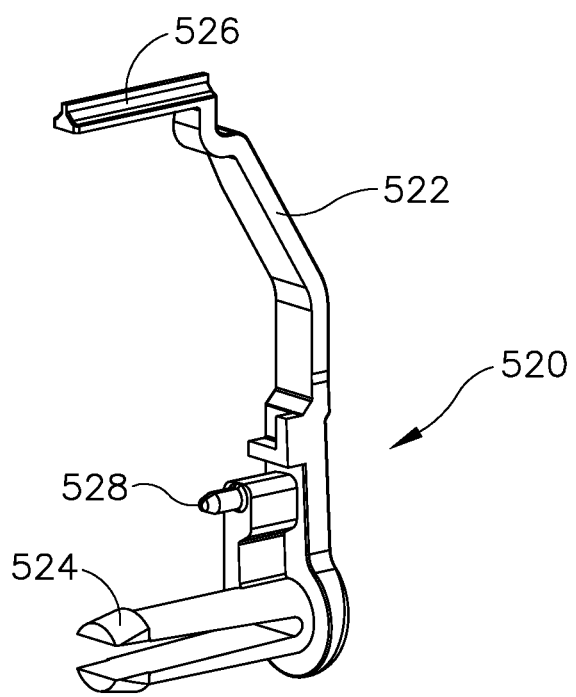
FIG. 11 depicts a perspective view of an indicator member of the handle assembly of FIG. 9.
Figure 12A:
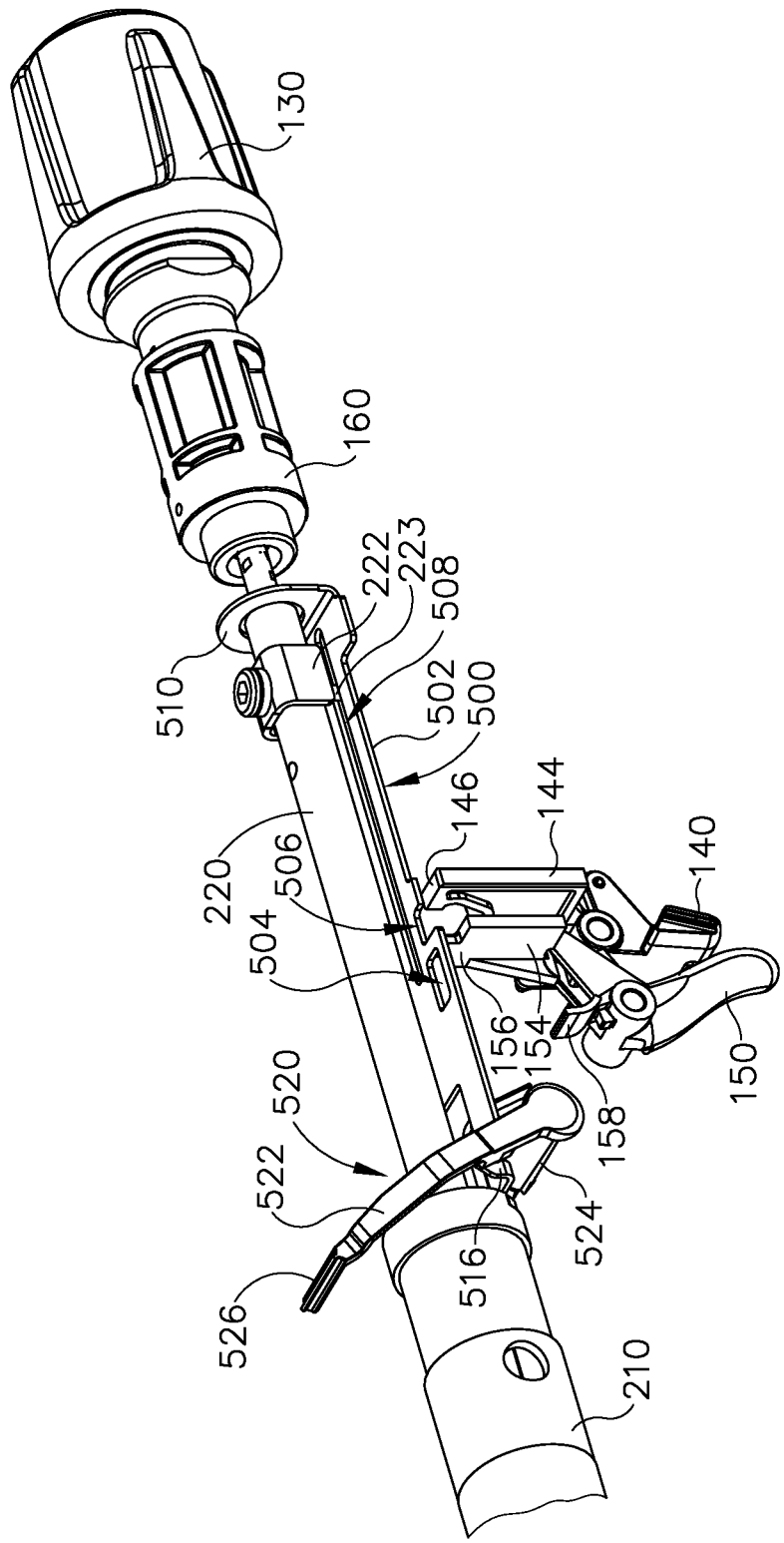
FIG. 12A depicts a perspective view of an anvil actuation assembly of the circular stapler of FIG. 1, an actuation rod in a first position.
Figure 12B:
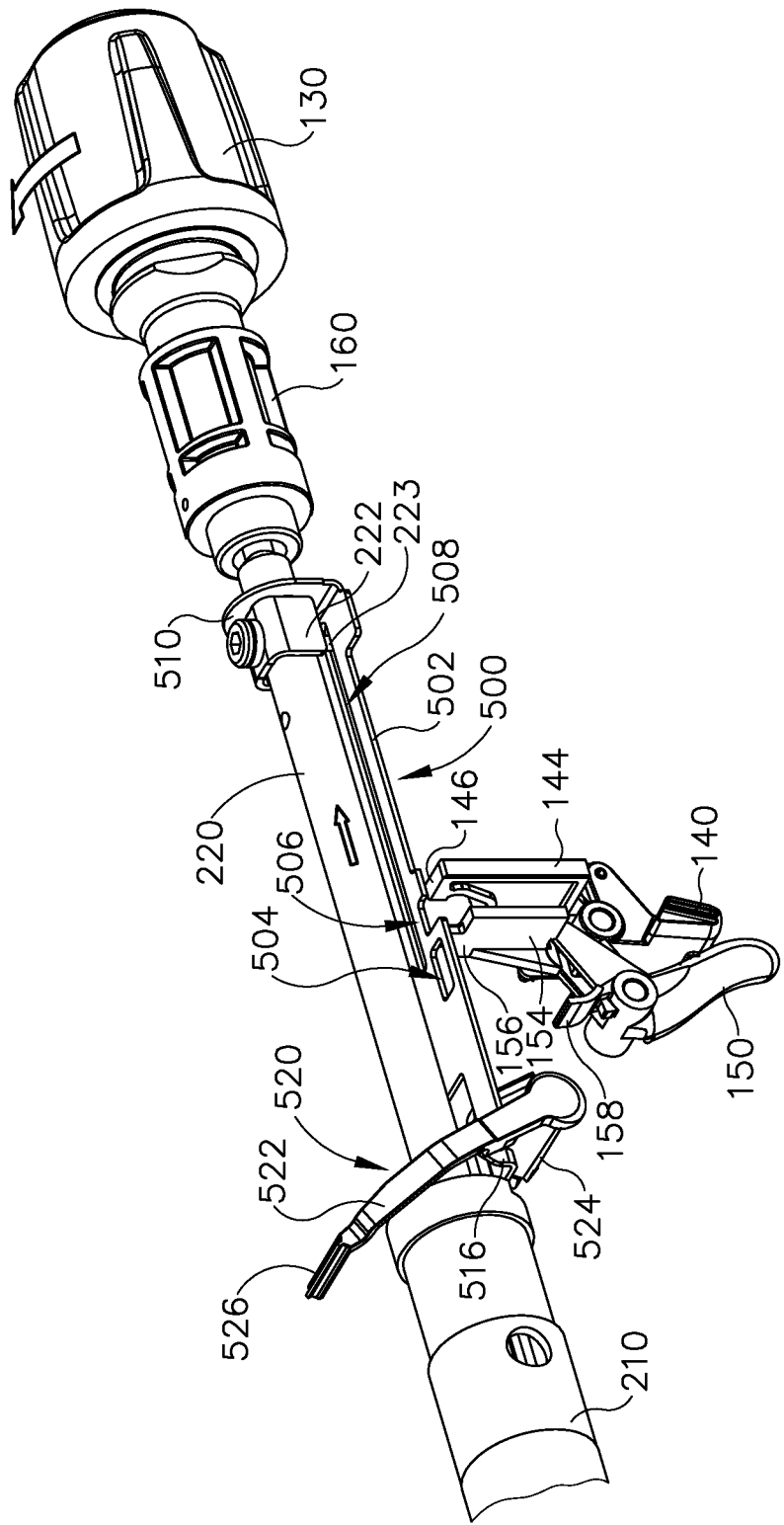
FIG. 12B depicts a perspective view of the anvil actuation assembly of FIG. 12A, with the actuation rod moved to a second position to engage the bracket of FIG. 10.
Figure 12C:
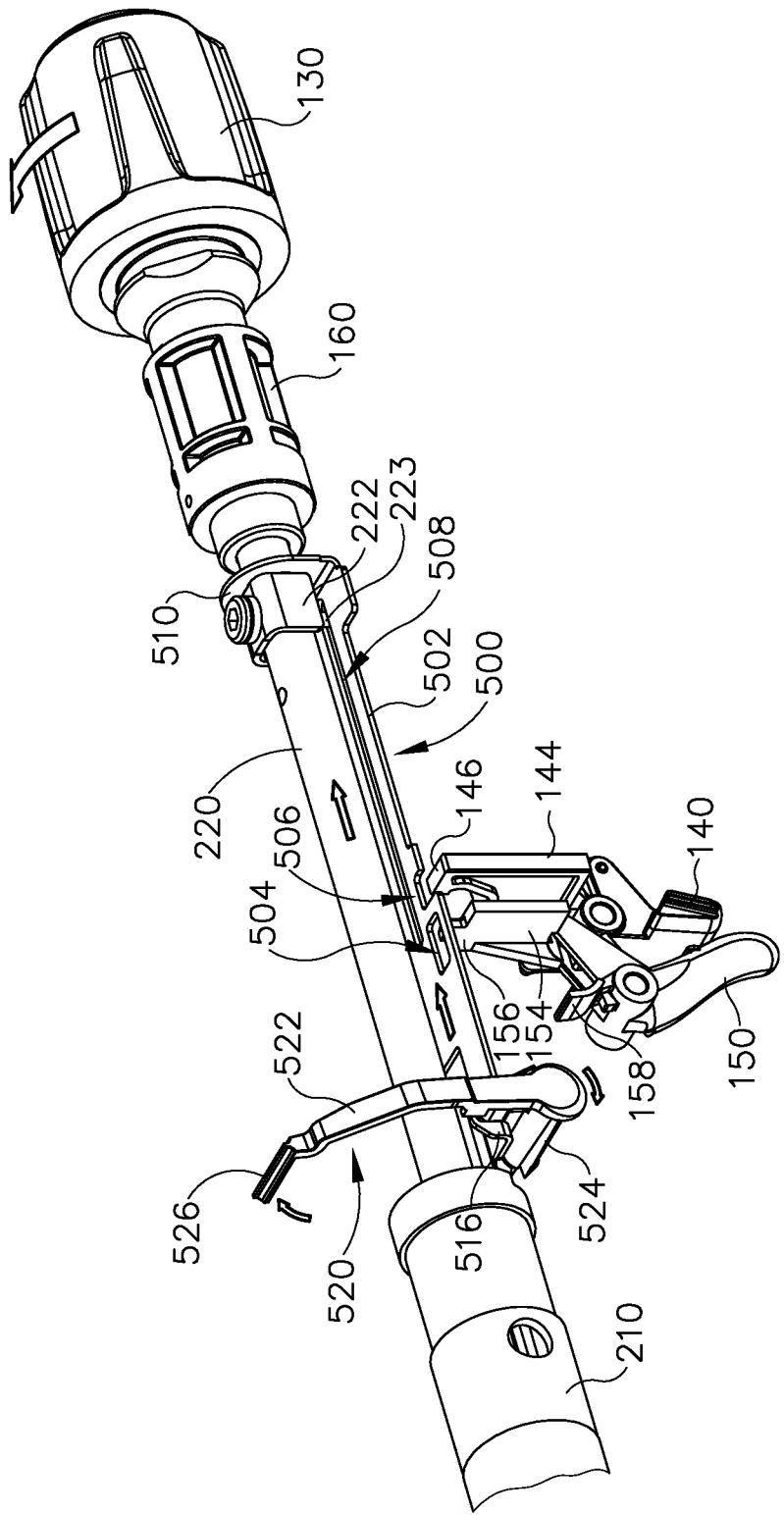
FIG. 12C depicts a perspective view of the anvil actuation assembly of FIG. 12A, with the actuation rod moved to a third position to retract the bracket of FIG. 10 proximally.

As best seen in FIGS. 12B-12C, an indicator member (520) is configured to pivot in response to translation of bracket (500). As best seen in FIG. 11, indicator member (520) comprises an upright arm (522), a snap pin (524) projecting laterally from a lower end of arm (522), an indicator needle (526) projecting laterally from an upper end of arm (522), and a coupling pin (528) projecting laterally from an intermediate region of arm (522). Snap pin (524) is configured to snap into a complementary recess provided by casing (110). Snap pin (524) thereby secures indicator member (520) to casing (110) yet permits indicator member (520) to pivot relative to casing (110) about the longitudinal axis of snap pin (524). Indicator needle (526) is positioned to be visible through window (114) of handle assembly (110) to thereby visually indicate the pivotal position of indicator member (520). Coupling pin (528) is slidably received in slot (514) of flange (516) of bracket (500). This engagement between indicator member (520), casing (110), and bracket (500) provides pivotal movement of indicator member (520) in response to translation of bracket (500).

Bracket (500) is configured to selectively prevent and permit actuation of triggers (140, 150). In particular, slots (504, 506) of bracket (500) are configured to selectively provide clearance for actuation of triggers (140, 150). As shown in FIGS. 12A-12E, safety trigger (140) is pivotably coupled with a first upright member (144). First upright member (144) is coupled with casing (110) such that first upright member (144) is configured to translate upwardly in response to pivoting of safety trigger (140) toward pistol grip (112). However, body (502) of bracket (500) is configured to prevent this movement of first upright member (144) and safety trigger (140) by engaging the upper end (146) of first upright member (144). Body (502) thus blocks movement of first upright member (144) and safety trigger (140) until bracket (500) is moved to a position where slot (506) is aligned with upper end (146) to thereby provide clearance for upward movement of first upright member (144). It should therefore be understood that safety trigger (140) cannot be pivoted toward pistol grip (112) until slot (506) is positioned over upper end (146).

Similarly, firing trigger (150) is pivotably coupled with a second upright member (154). Second upright member (154) is coupled with casing (110) such that second upright member (154) is configured to translate upwardly in response to pivoting of safety trigger (150) toward pistol grip (112). However, body (502) of bracket (500) is configured to prevent this movement of second upright member (154) and firing trigger (150) by engaging the upper end (156) of second upright member (154). Even if safety trigger (140) is pivoted out of the way to otherwise permit movement of firing trigger (150), body (502) blocks movement of second upright member (154) and firing trigger (150) until bracket (500) is moved to a position where slot (504) is aligned with upper end (156) to thereby provide clearance for upward movement of second upright member (154). It should therefore be understood that, even if safety trigger (140) is pivoted out of the way to otherwise permit movement of firing trigger (150), firing trigger (150) cannot be pivoted toward pistol grip (112) until slot (504) is positioned over upper end (156).

Third slot (508) is configured to receive a downwardly projecting boss (223) of clip (222), which is rigidly secured to trocar actuation rod (220). While casing (110) is configured to allow bracket (500) to translate longitudinally within casing (110), casing (110) includes rails, channels, and/or other features that prevent bracket (500) from rotating within casing (110). Thus, the positioning of boss (223) in slot (508) prevents clip (222) and trocar actuation rod (220) from rotating within casing (110). Boss (223) and slot (508) nevertheless allow bracket (500) to translate longitudinally within casing (110) as will be described in greater detail below.

FIGS. 12A-12E depict the above-described components at various stages of operation. In particular, in FIG. 12A, trocar actuation rod (220) is in a distal-most position, such that trocar (330) is in a distal-most position. At this stage, the operator may couple anvil (400) with trocar (330) by inserting trocar (330) into bore (422) until latch members (430) are secured to head (334) of trocar (330). The operator then rotates knob (130), which rotates nut (160). As knob (130) and nut (160) rotate, engagement between coarse helical threading (224) of trocar actuation rod (220) and the complementary feature of nut (160) causes trocar actuation rod (220) to retract proximally at a relatively rapid rate, such that trocar actuation rod (220) reaches the position shown in FIG. 12B. This provides proximal retraction of trocar actuation rod (220) provides retraction of trocar (330) and anvil (400). As trocar actuation rod (220) moves from the position shown in FIG. 12A to the position shown in FIG. 12B, bracket (500) remains stationary. This is due to the fact that clip (222) is spaced apart from upright feature (510) at the stage shown in FIG. 12A and does not engage upright feature (510) until trocar actuation rod (220) reaches the position shown in FIG. 12B.

After reaching the stage shown in FIG. 12B, the operator may continue rotating knob (130) and nut (160), which causes further proximal retraction of trocar actuation rod (220) as shown in FIG. 12C. This of course causes further proximal retraction of trocar (330) and anvil (400). As trocar actuation rod (220) moves from the position shown in FIG. 12B to the position shown in FIG. 12C, clip (222) bears against bracket (500), driving bracket (500) proximally. This proximal movement of bracket (500) causes indicator member (520) to pivot from the position shown in FIG. 12B to the position shown in FIG. 12C due to the positioning of pin (528) in slot (514) of flange (516).

As indicator member (520) pivots from the position shown in FIG. 12B to the position shown in FIG. 12C, the operator may observe the position of indicator needle (526) through window (114) of handle assembly (110). As noted above, a series of hash marks, colored regions, and/or other fixed indicators may be positioned adjacent to window (114) in order to provide a visual context for indicator needle (526), thereby facilitating operator evaluation of the position of needle (526) within window (114). It should be understood that the position of needle (526) within window (114) will be indicative of the longitudinal position of trocar (330) and anvil (400). The position of needle (526) within window (114) will thus indicate the gap distance (d) between opposing surfaces (412, 322) of anvil (400) and stapling head assembly (300). While observing the position of needle (526) within window (114), the operator may rotate knob (130) clockwise or counterclockwise to further retract or advance trocar (330) and anvil (400), thereby providing fine adjustment of the gap distance (d) until a desired gap distance (d) is reached within an appropriate range.

In order to provide fine control of the gap distance (d) adjustment at the stage shown in FIG. 12C, trocar actuation rod (220) will be at a longitudinal position where fine helical threading (226) is engaged with a complementary feature of knob (130) and coarse helical threading (224) is disengaged from the complementary feature of nut (160). In some versions, coarse helical threading (224) disengages nut (160) and fine helical threading (226) begins to engage knob (130) once trocar actuation rod (220) reaches the longitudinal position shown in FIG. 12B (i.e., when clip (222) first engages upright member (510)). In some other versions, the transition from engagement by coarse helical threading (224) to fine helical threading (226) occurs sometime between the stage shown in FIG. 12B and the stage shown in FIG. 12C. Other suitable stages at which the coarse-to-fine transition may occur will be apparent to those of ordinary skill in the art in view of the teachings herein. It should also be understood that some alternative versions of trocar actuation rod (220) may have just a single threading section, with the pitch of the threading being consistent along the length of the threading. In other words, trocar actuation rod (220) does not necessarily need to have two different sections of threading (224, 226) with different pitches.

At the stage shown in FIG. 12C, slot (506) is aligned with upper end (146) to thereby provide clearance for upward movement of first upright member (144). Similarly, slot (504) is aligned with upper end (156) to thereby provide clearance for upward movement of second upright member (154). In the present example, slots (504, 506) are sized and positioned such that slots (504, 506) only provide clearance for upward movement of upright members (144, 154) when the gap distance (d) is within a clinically acceptable range. By way of example only, a "clinically acceptable range" for the gap distance (d) may be between approximately 0.110 inches and approximately 0.040 inches. As another merely illustrative example, a "clinically acceptable range" for the gap distance (d) may be between approximately 0.110 inches and approximately 0.020 inches. Even when slots (504, 506) are positioned to provide clearance for upward movement of upright members (144, 154) as shown in FIG. 12C, safety trigger (140) will still block pivotal movement of firing trigger (150) about a pin (152) (FIG. 9) when safety trigger (140) is in the non-actuated position shown in FIG. 12C. Thus, in order to enable movement of firing trigger (150), the operator will need to first actuate safety trigger (140) about a pin (142) (FIG. 9) from the position shown in FIG. 12C to the position shown in FIG. 12D.

Figure 12D:
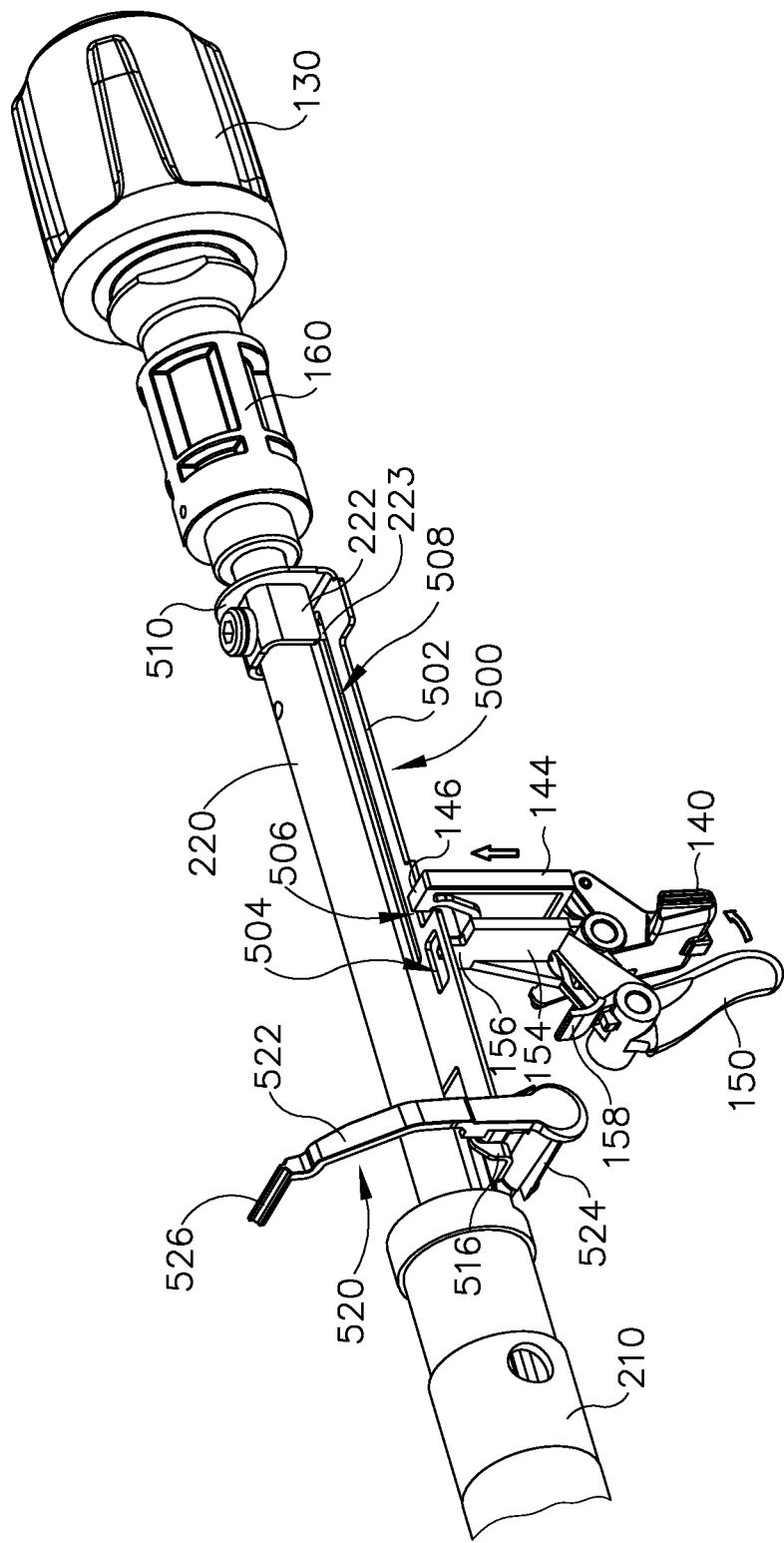
FIG. 12D depicts a perspective view of the anvil actuation assembly of FIG. 12A, with a safety trigger pivoted from a first position to a second position.

As shown in FIG. 12D, upper end (146) passes through slot (506) as safety trigger (140) is pivoted from the position shown in FIG. 12C to the position shown in FIG. 12D. It should be understood that this movement of upper end (146) would not be possible at the stages shown in FIGS. 12A-12B (when the gap distance (d) is too great) because body (502) would physically block upward movement of upright member (144), thereby physically blocking pivotal movement of safety trigger (140). In the present example, a cap (not shown) incorporated into knob (130) prevents knob (130) from rotating to a point where anvil (400) would be retracted too far proximally (such that the gap distance (d) is too small). In some other variations, even if knob (130) were to permit anvil (400) to be retracted too far proximally (such that the gap distance (d) is too small), body (502) would physically block upward movement of upright member (144), thereby physically blocking pivotal movement of safety trigger (140), in the event that the operator retracts trocar (330) and anvil (400) too far proximally (such that the gap distance (d) is too small). Regardless of whether body (502), knob (130), or some other feature prevents actuation when the gap distance (d) would be too small, it should be understood that instrument (10) permits actuation of safety trigger (140) only when the gap distance (d) is within the clinically acceptable range.

Figure 12E:
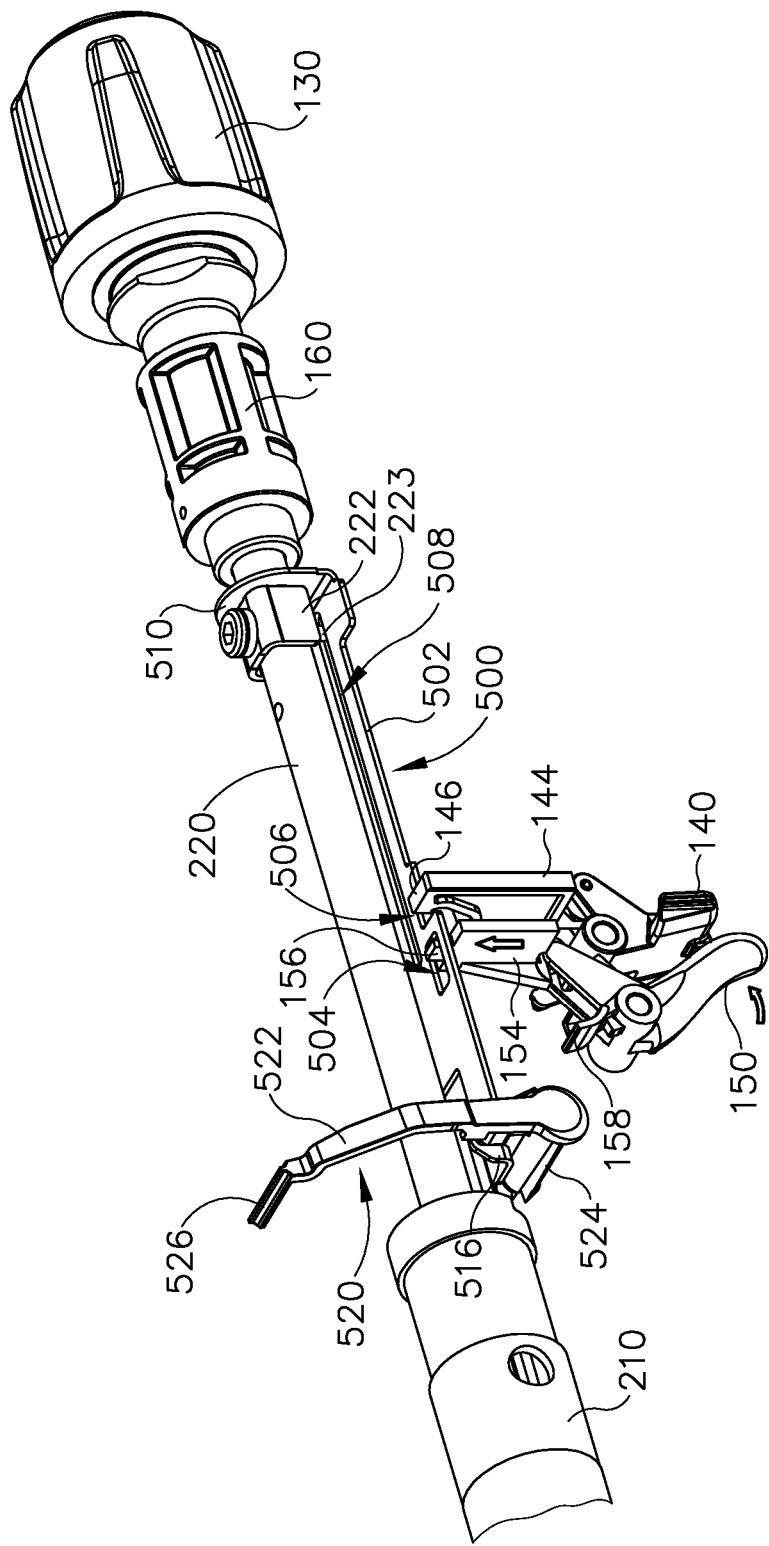
FIG. 12E depicts a perspective view of the anvil actuation assembly of FIG. 12A, with a firing trigger pivoted from a first position to a second position.
Figure 13:
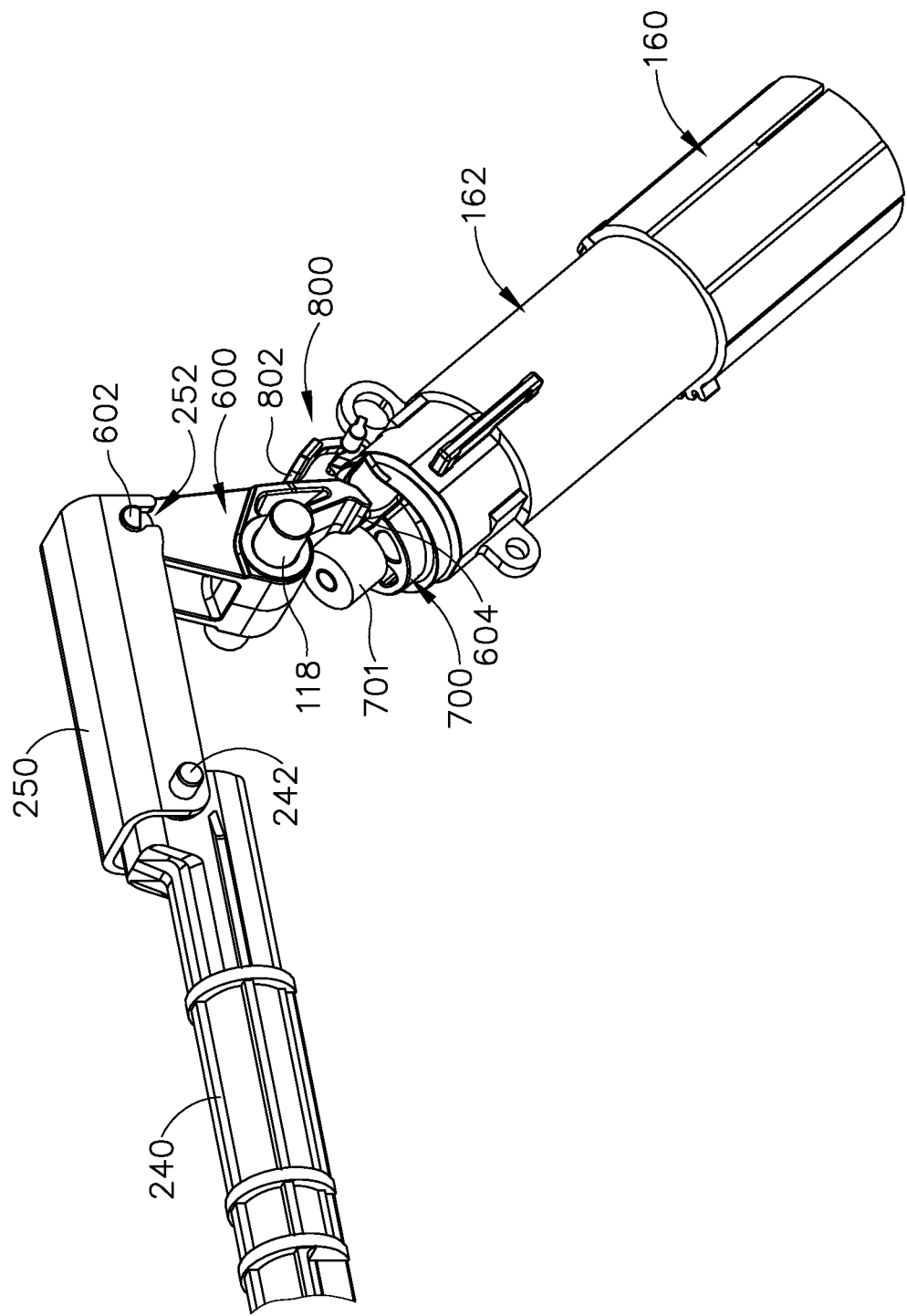
FIG. 13 depicts a perspective view of a stapling head actuation assembly of the circular stapler of FIG. 1.

As noted above, safety trigger (140) is configured to prevent actuation of firing trigger (150) until safety trigger (140) has been actuated. Once safety trigger (140) has been actuated, the operator may actuate firing trigger (150) from the position shown in FIG. 12D to the position shown in FIG. 12E. As shown in FIG. 12E, upper end (156) passes through slot (504) as firing trigger (150) is pivoted from the position shown in FIG. 12D to the position shown in FIG. 12E. It should be understood that, even in the complete absence of safety trigger (140), this movement of upper end (156) would not be possible at the stages shown in FIGS. 12A-12B (when the gap distance (d) is too great) because body (502) would physically block upward movement of upright member (154), thereby physically blocking pivotal movement of firing trigger (150). It should also be understood that body (502) would also physically block upward movement of upright member (154), thereby physically blocking pivotal movement of firing trigger (150), in the event that the operator retracts trocar (330) and anvil (400) too far proximally (such that the gap distance (d) is too small). Thus, even in the complete absence of safety trigger (140), firing trigger (150) may only be actuated when the gap distance (d) is within the clinically acceptable range.

Firing trigger (150) of the present example includes an integral actuation paddle (158). Paddle (158) pivots forwardly as firing trigger (150) pivots from the position shown in FIG. 12D to the position shown in FIG. 12E. Paddle (158) is configured to actuate a switch of a motor activation module (180), which is shown in FIG. 9, when firing trigger (150) pivots from the position shown in FIG. 12D to the position shown in FIG. 12E. Motor activation module (180) is in communication with battery pack (120) and motor (160), such that motor activation module (180) is configured to provide activation of motor (160) with electrical power from battery pack (120) in response to paddle (158) actuating the switch of motor activation module (180). Thus, motor (160) will be activated when firing trigger (150) is pivoted from the position shown in FIG. 12D to the position shown in FIG. 12E. This activation of motor (160) will actuate stapling head assembly (300) as described in greater detail below.

3. Exemplary Stapling Head Actuation Assembly

FIGS. 13-20D show various components that are operable to actuate stapling head assembly (300). These components include motor (160), a gearbox (162), a rotary cam member (700), a cam follower (600), drive bracket (250) and stapling head assembly driver (240). Gearbox (162) is coupled with a drive shaft of motor (160) and is further coupled with cam member (700). Activation of motor (160) thus causes rotation of cam member (700) via gearbox (162). Various suitable configurations that may be used for gearbox (162) will be apparent to those of ordinary skill in the art in view of the teachings herein. Cam member (700) is configured to interact with cam follower (160) to pivot cam follower (160) in two angular directions about a pin (118) as will be described in greater detail below. Pin (118) is coupled with casing (110). A bushing (701) provides rotary support to cam member (700) relative to casing (110).

Figure 14:
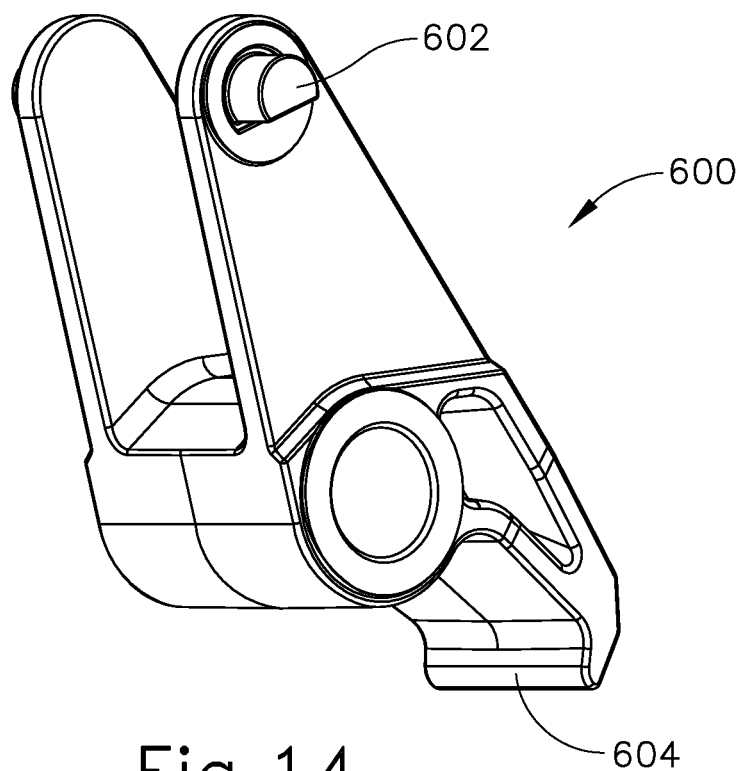
FIG. 14 depicts a perspective view of a cam follower of the stapling head actuation assembly of FIG. 13.
Figure 15:
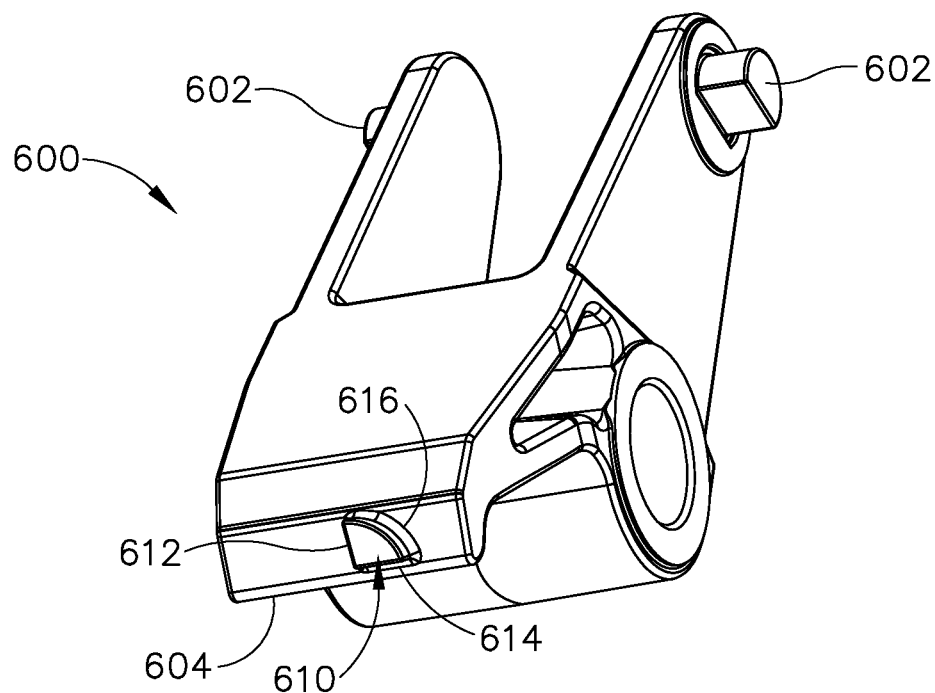
FIG. 15 depicts another perspective view of the cam follower of FIG. 14.

Cam follower (600) is pivotably coupled with drive bracket (250) via a pair of integral pins (602), which are received in complementary notches (252) of drive bracket (250). As shown in FIGS. 14-15, cam follower (600) includes a first bearing feature (604) and a second bearing feature (610). First bearing feature (604) consists of a rounded, horizontally extending surface. Second bearing feature (610) is shaped like a quarter-pie defined by a straight vertical surface (612), a horizontally extending surface (614), and a curved surface (616). Second bearing feature (610) projects proximally relative to first bearing feature (504).

Figure 16:
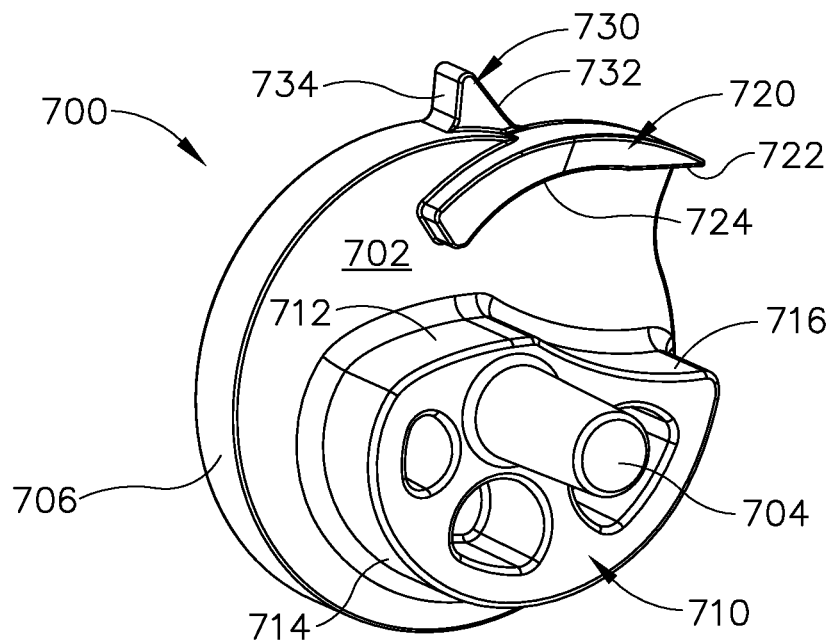
FIG. 16 depicts a perspective view of a rotary cam of the stapling head actuation assembly of FIG. 13.
Figure 17:
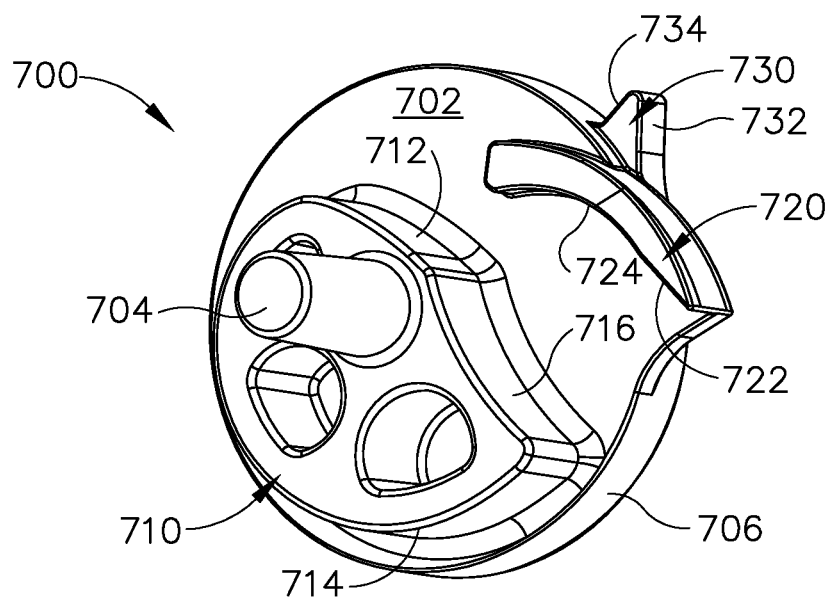
FIG. 17 depicts another perspective view of the rotary cam of FIG. 16.

FIGS. 16-17 show cam member (700) in greater detail. Cam member (700) comprises a distal face (702), a distally projecting post (704), and an outer circumferential surface (706). A first cam feature (710) and a second cam feature (720) project distally from distal face (702). Post (704) engages bushing (701). First cam feature (710) comprises a first surface region (712), a second surface region (714), and a third surface region (716). First surface region (712) is convexly defined by a relatively large radius of curvature, such that first surface region (712) is nearly flat. Second surface region (714) is convexly defined by a progressively increasing radius of curvature. Third surface region (716) is concavely defined by a relatively large radius of curvature. In addition to projecting distally from distal face (702), second cam feature (720) projects outwardly from outer circumferential surface (706). Second cam feature (720) includes a first surface region (722) and a second surface region (724). First surface region (722) is substantially flat while second surface region (724) is concavely curved. The origin of the radius of curvature for each curved surface region (712, 714, 716, 724) is offset from the center of post (704).

Figure 18A:
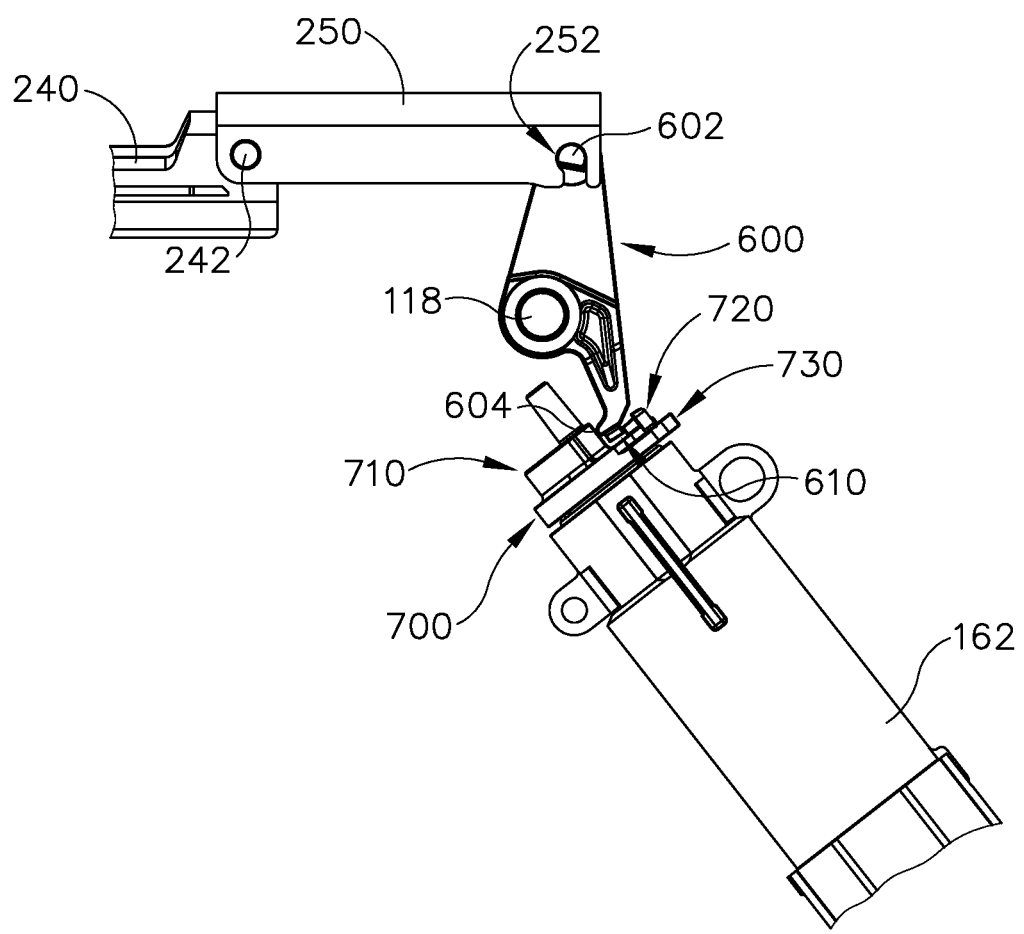
FIG. 18A depicts a side elevational view of the stapling head actuation assembly of FIG. 13, with the rotary cam in a first angular position and the cam follower in a first pivotal position.
Figure 18B:
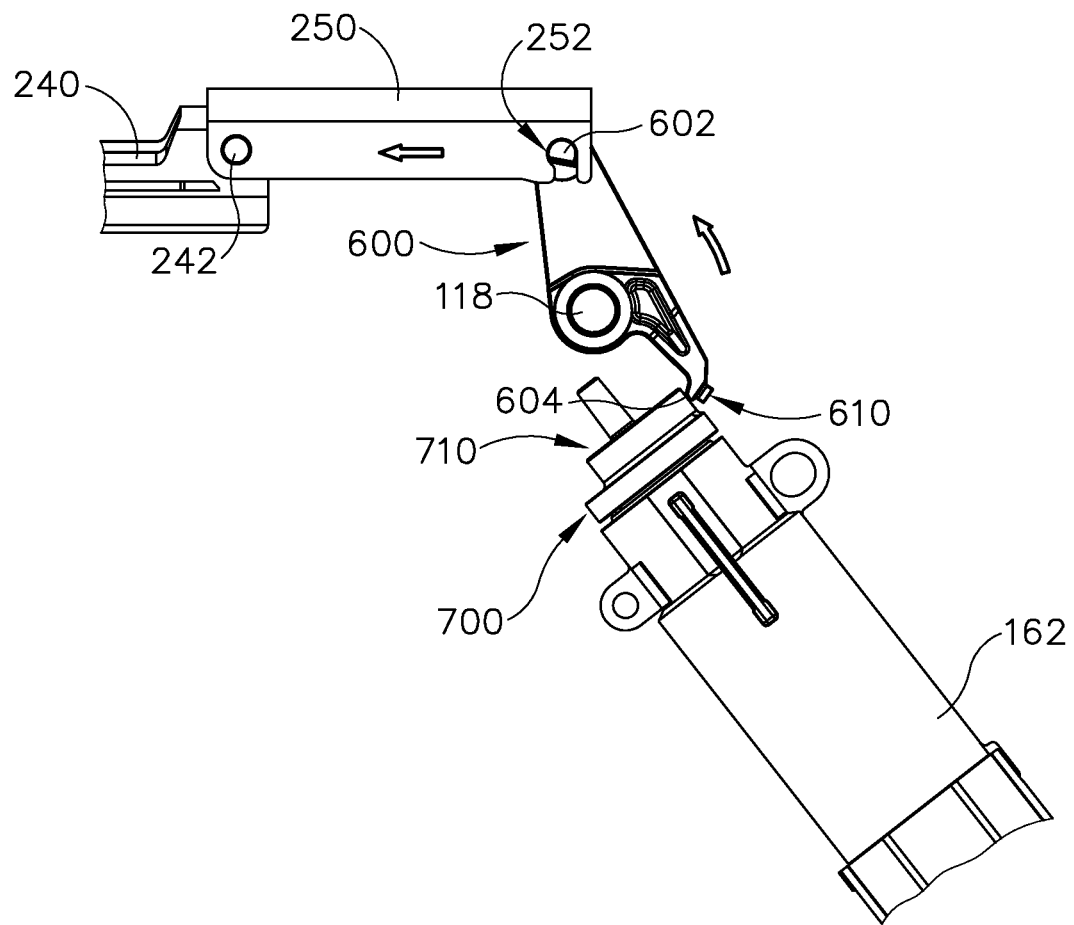
FIG. 18B depicts a side elevational view of the stapling head actuation assembly of FIG. 13, with the rotary cam in a second angular position and the cam follower in a second pivotal position.

FIGS. 18A-18B show the general interaction between cam follower (600) and first and second cam features (710, 720), though this interaction will be described in greater detail below with reference to FIGS. 20A-20D. As cam member (700) is rotated from the position shown in FIG. 18A to the position shown in FIG. 18B, first cam feature (710) bears against first bearing feature (604) of cam follower (600), causing cam follower to pivot about pin (118). In the view shown in FIGS. 18A-18B, cam follower (600) pivots counterclockwise as cam member (700) is rotated from the position shown in FIG. 18A to the position shown in FIG. 18B. As can be seen in the transition from FIG. 18A to FIG. 18B, this counterclockwise pivoting of cam follower (600) drives drive bracket (250) and stapling head assembly driver (240) distally, thereby actuating stapling head assembly (300). As cam member (700) continues to rotate in the same direction back toward the position shown in FIG. 18A, second cam feature (720) engages and bears against second bearing feature (610) of cam follower (600), causing cam follower (600) to pivot clockwise about pin (118). This clockwise pivoting of cam follower (600) about pin (118) retracts drive bracket (250) and stapling head assembly driver (240) proximally back toward the position shown in FIG. 18A.

Figure 19A:
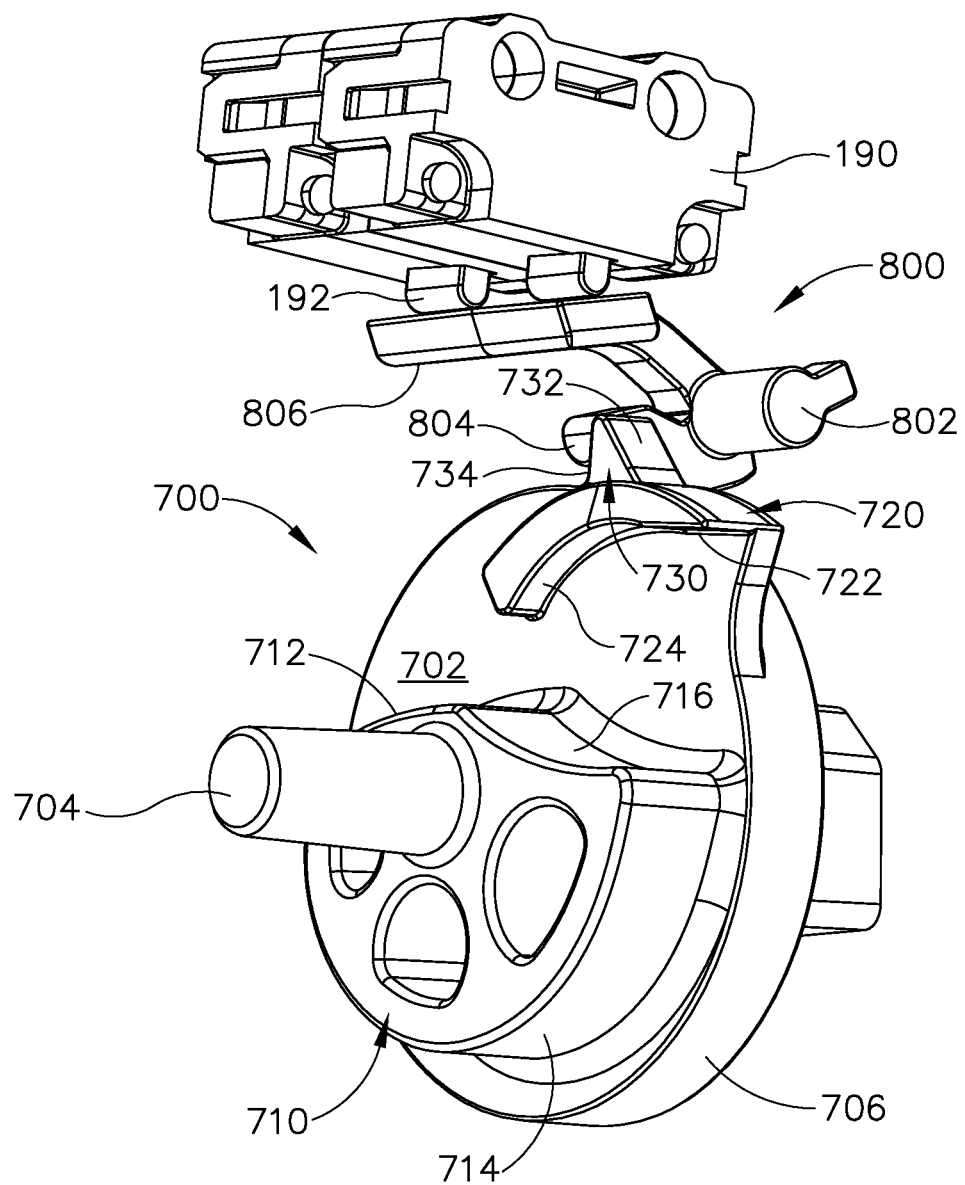
FIG. 19A depicts a perspective view of the rotary cam of FIG. 16, a rocker member, and a stop switch, with the rotary cam in a first angular position and the rocker member in a first pivotal position.
Figure 19B:
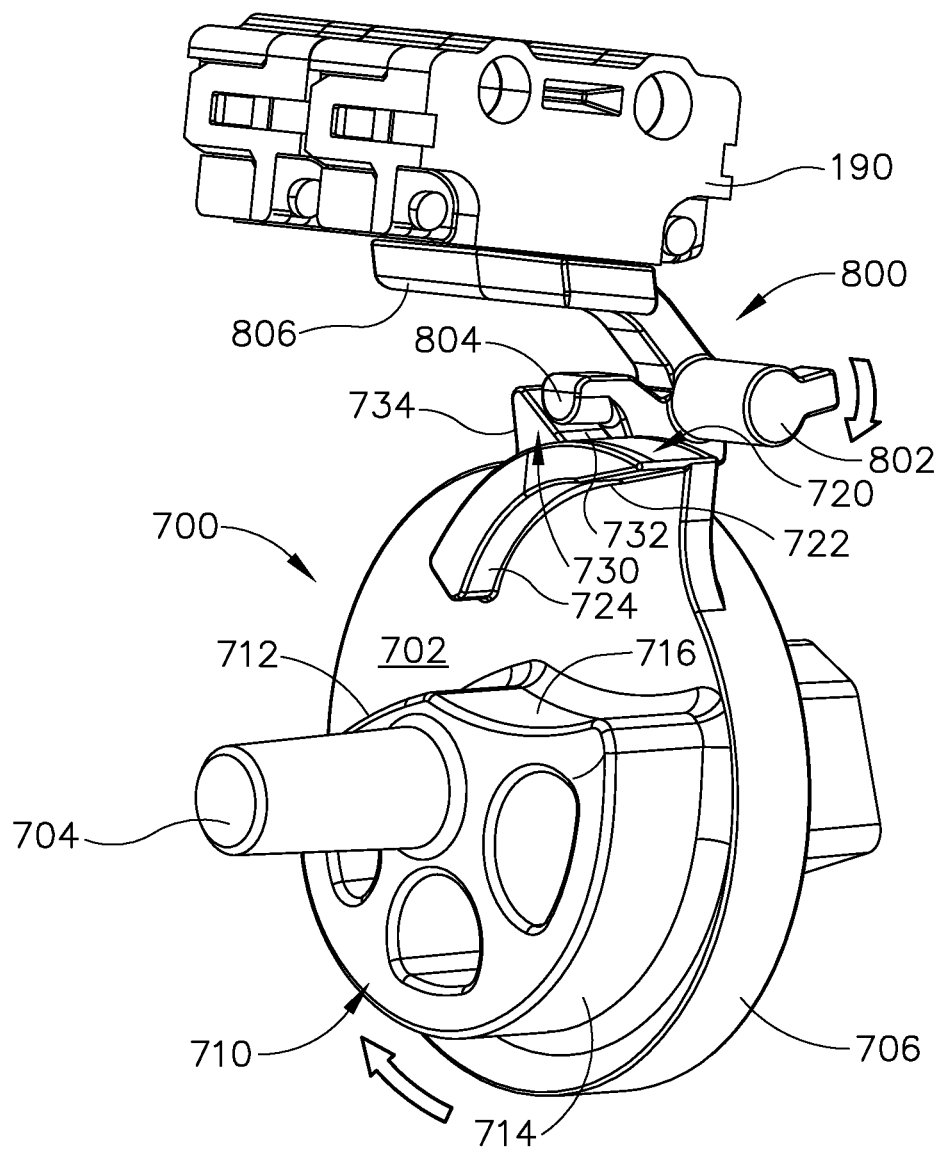
FIG. 19B depicts a perspective view of the rotary cam of FIG. 16, the rocker member of FIG. 19A, and the stop switch of FIG. 19A, with the rotary cam in a fourth angular position and the rocker member in a second pivotal position.

Referring back to FIGS. 16-17, a third cam feature (730) projects outwardly from outer circumferential surface (706). Third cam feature (730) comprises a first surface region (732) and a second surface region (734). First surface region (732) is flat and is oriented generally tangentially relative to outer circumferential surface (706). Second surface region (732) is also flat and is oriented radially outwardly relative to outer circumferential surface (706). Third cam feature (730) is configured to interact with a rocker member (800) as shown in FIGS. 19A-19B. Rocker member (800) comprises an integral pin (802), a bearing member (804), and a paddle (806). Pin (802) is pivotably coupled with casing (110), such that rocker member (800) is pivotable within casing (110) about the longitudinal axis defined by pin (802). Bearing member (804) is configured to interact with third cam feature (730) as will be described in greater detail below. Paddle (806) is configured to actuate a switch button (192) of a short circuit module (190) as will also be described in greater detail below.

FIG. 19A shows cam member (700) in the same position as shown in FIG. 18A. At this stage, second surface region (734) of third cam feature (730) is adjacent to bearing member (804) of rocker member (800). FIG. 19B shows cam member (700) in a position where cam member (700) has been rotated past the position shown in FIG. 18B and back toward the position shown in FIG. 18A. However, cam member (700) has not completed a full revolution. At the stage shown in FIG. 19B, first surface region (732) has engaged and borne against bearing member (804), thereby pivoting rocker member (800) about the longitudinal axis defined by pin (802). This has caused paddle (806) to actuate switch button (192) of short circuit module (190). Short circuit module (190) is configured to prevent motor (160) from further activation when switch button (192) has been actuated. In some versions, short circuit module (190) couples battery pack (120) with a power sink, in addition to short circuiting motor (160), when switch button (192) is actuated. This may result in discharge of battery pack (120)

in addition to stopping activation of motor (160) once an actuation stroke of stapling head assembly (300) has been completed. By way of example only, short circuit module (190) may be configured and operable in accordance with at least some of the teachings of U.S. Pub. No. 2015/0083774, issued as U.S. Pat. No. 9,907,552, the disclosure of which is incorporated by reference herein. Other suitable configurations will be apparent to those of ordinary skill in the art in view of the teachings herein.

Figure 20A:
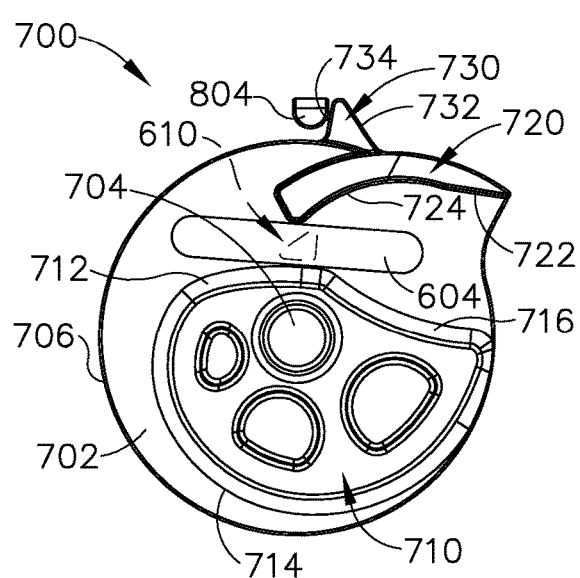
FIG. 20A depicts a schematic end view of the rotary cam of FIG. 16, the cam follower of FIG. 14, and the rocker member of FIG. 19A, with the rotary cam in the first angular position, the cam follower in the first pivotal position, and the rocker member in the first pivotal position.
Figure 20B:
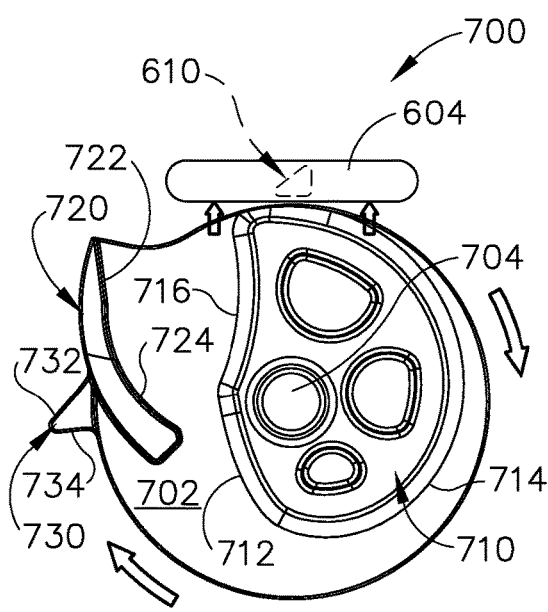
FIG. 20B depicts a schematic end view of the rotary cam of FIG. 16 and the cam follower of FIG. 14, with the rotary cam in the second angular position, the cam follower in the second pivotal position, and the rocker member of FIG. 19A in the first pivotal position.

FIGS. 20A-20D schematically depict the interaction between cam member (700), features of cam follower (600), and features of rocker member (800) as cam member (700) rotates. It should be understood that the rotation of cam member (700) throughout the stages shown in FIGS. 20A-20D is driven by motor (160) and gearbox (162). FIG. 20A shows cam member (700) in the same position as shown in FIGS. 18A and 19A. At this stage, first bearing feature (604) of cam follower (600) is positioned on first surface region (712) and bearing member (804) or rocker member (800) is adjacent to second surface region (734) of third cam feature (730). Also at this stage, knife member (340) and staple driver member (350) are in proximal positions, such that stapling head assembly (300) is in a non-actuated state. As cam member (700) is rotated to the position shown in FIG. 20B, second surface region (714) bears against bearing member (804), thereby driving bearing member (804) upwardly. This causes cam follower (600) to pivot about pin (118) to the position shown in FIG. 18B. Cam follower (600) thus drives knife member (340) and staple driver member (350) distally via drive bracket (250) and stapling head assembly driver (240). Stapling head assembly (300) is thus in an actuated state at the stage shown in FIG. 20B. In some versions, cam member (700) rotates through an angular range of approximately 270° in order to transition stapling head assembly (300) from the non-actuated state to the actuated state.

Figure 20C:
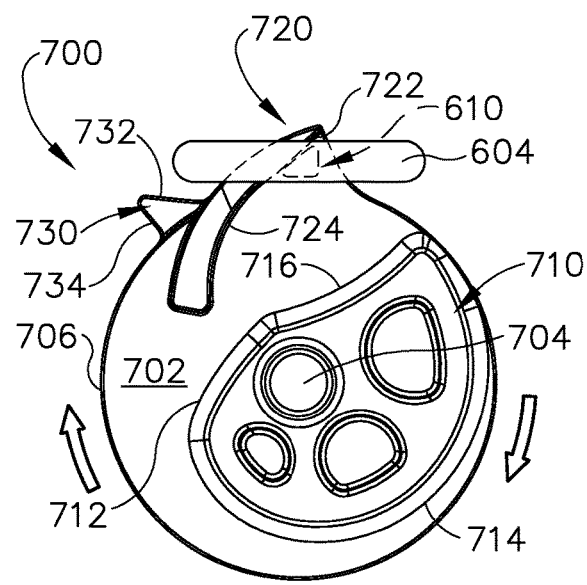
FIG. 20C depicts a schematic end view of the rotary cam of FIG. 16 and the cam follower of FIG. 14, with the rotary cam in a third angular position, the cam follower in the second pivotal position, and the rocker member of FIG. 19A in the first pivotal position.
Figure 20D:
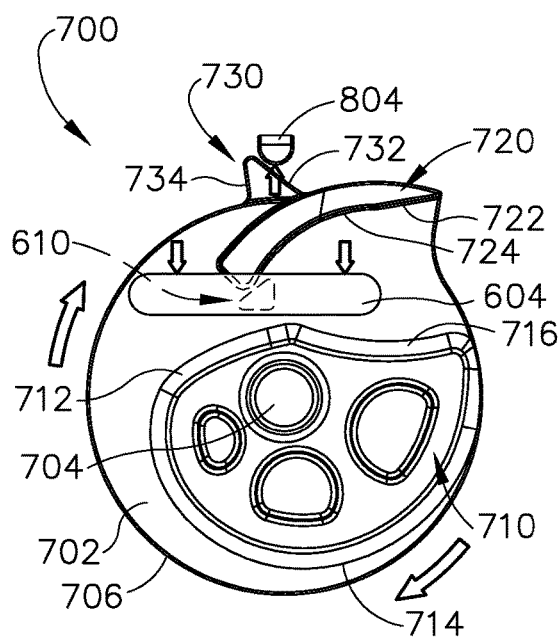
FIG. 20D depicts a schematic end view of the rotary cam of FIG. 16, the cam follower of FIG. 14, and the rocker member of FIG. 19A, with the rotary cam in a fourth angular position, the cam follower in a third pivotal position, and the rocker member in a second pivotal position.

After stapling head assembly (300) has been actuated, cam member (700) continues to rotate to the position shown in FIG. 20C. At this stage, first surface region (722) of second cam member (720) begins to engage curved surface (616) of second bearing feature (610) of cam follower (600). As cam member (700) continues to rotate to the position shown in FIG. 20D, second surface region (724) engages curved surface (616) of second bearing feature (610), driving second bearing feature (610) downwardly. This causes cam follower (600) to pivot about pin (118) back from the position shown in FIG. 18B toward the position shown in FIG. 18A. Cam follower (600) thus drives knife member (340) and staple driver member (350) proximally via drive bracket (250) and stapling head assembly driver (240). In addition, first surface region (732) has engaged and borne against bearing member (804), thereby pivoting rocker member (800) about the longitudinal axis defined by pin (802) at the stage shown in FIG. 20D. Rocker member (800) is thus in the same state in FIG. 20D as shown in FIG. 19B. Short circuit module (190) has thus been actuated at the stage shown in FIG. 20D.

It should be understood from the foregoing that cam member (700) is operable to drive knife member (340) and staple driver member (350) distally, then drive knife member (340) and staple driver member (350) proximally and actuate short circuit module (190) by rotating in a single angular direction through the range of motion shown in FIGS. 20A-20D. Other suitable ways in which knife member (340), staple driver member (350), and short circuit module (190) may be actuated will be apparent to those of ordinary skill in the art in view of the teachings herein.

E. Exemplary Anastomosis Procedure

Figure 21A:
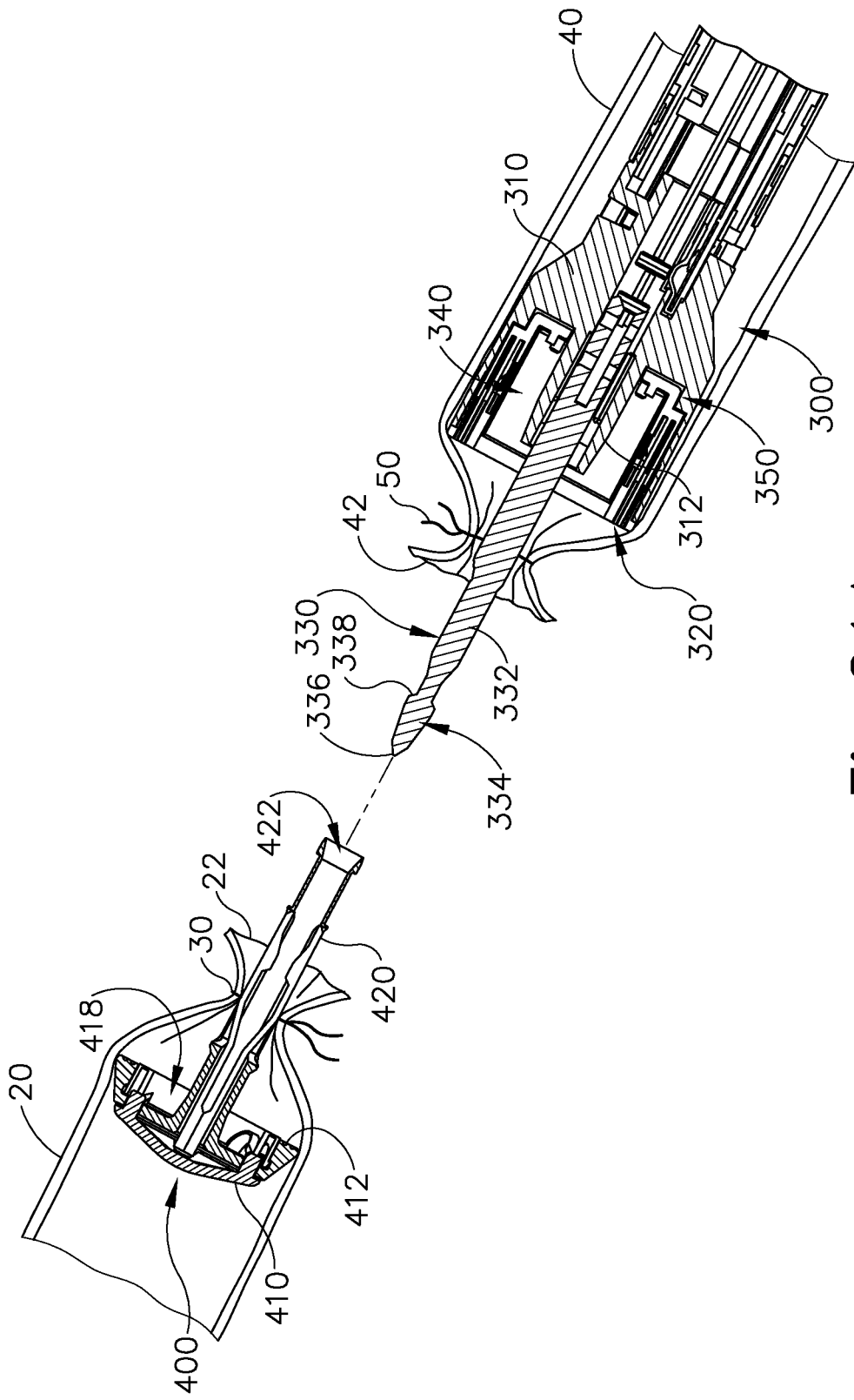
FIG. 21A depicts a cross-sectional side view of the anvil of FIG. 3 positioned within a first section of a digestive tract and the stapling head assembly of FIG. 6 positioned in a second section of the digestive tract, with the anvil separated from the stapling head assembly.
Figure 21B:
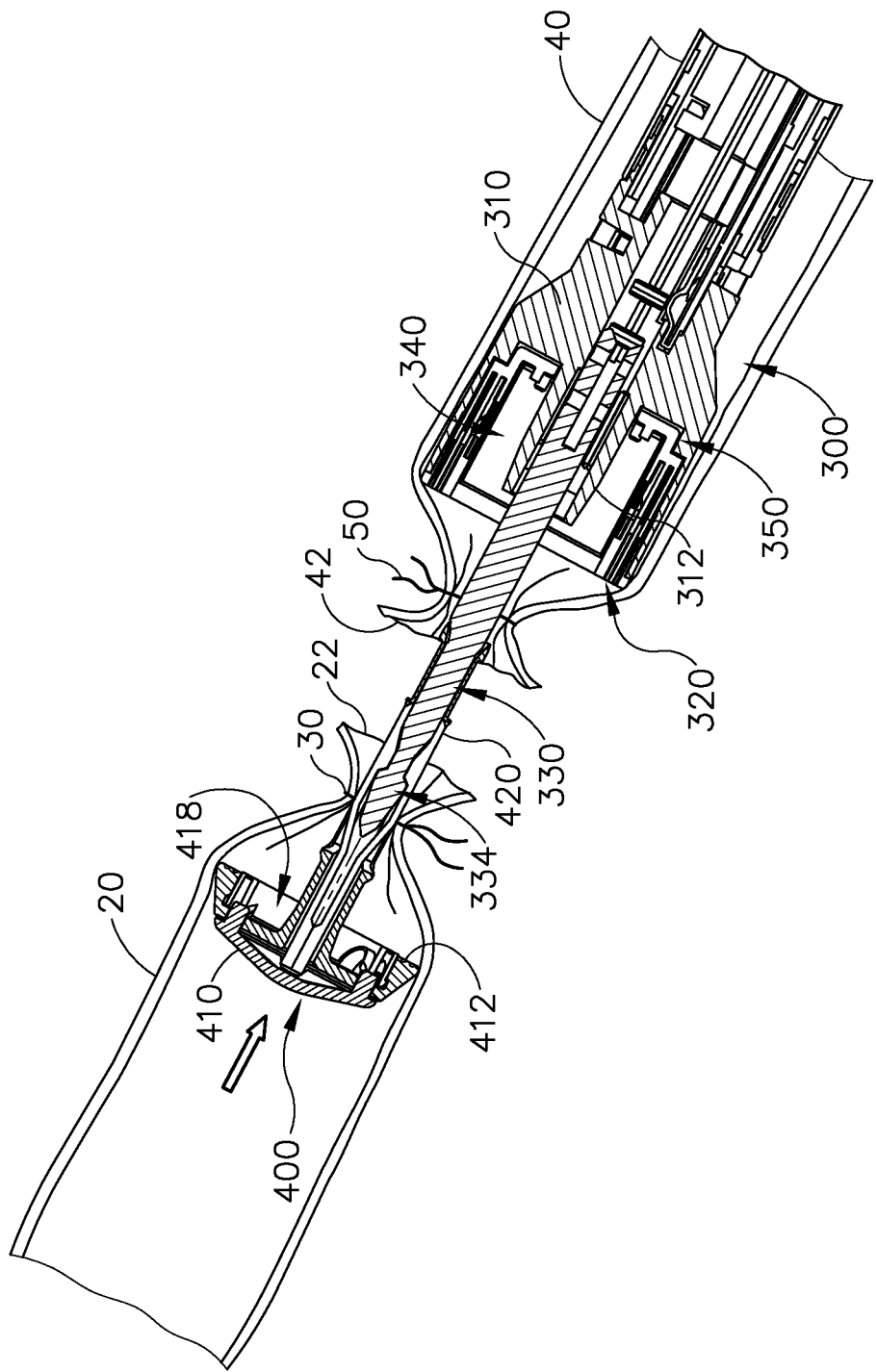
FIG. 21B depicts a cross-sectional side view of the anvil of FIG. 3 positioned within the first section of the digestive tract and the stapling head assembly of FIG. 6 positioned in the second section of the digestive tract, with the anvil secured to the stapling head assembly.
Figure 21C:
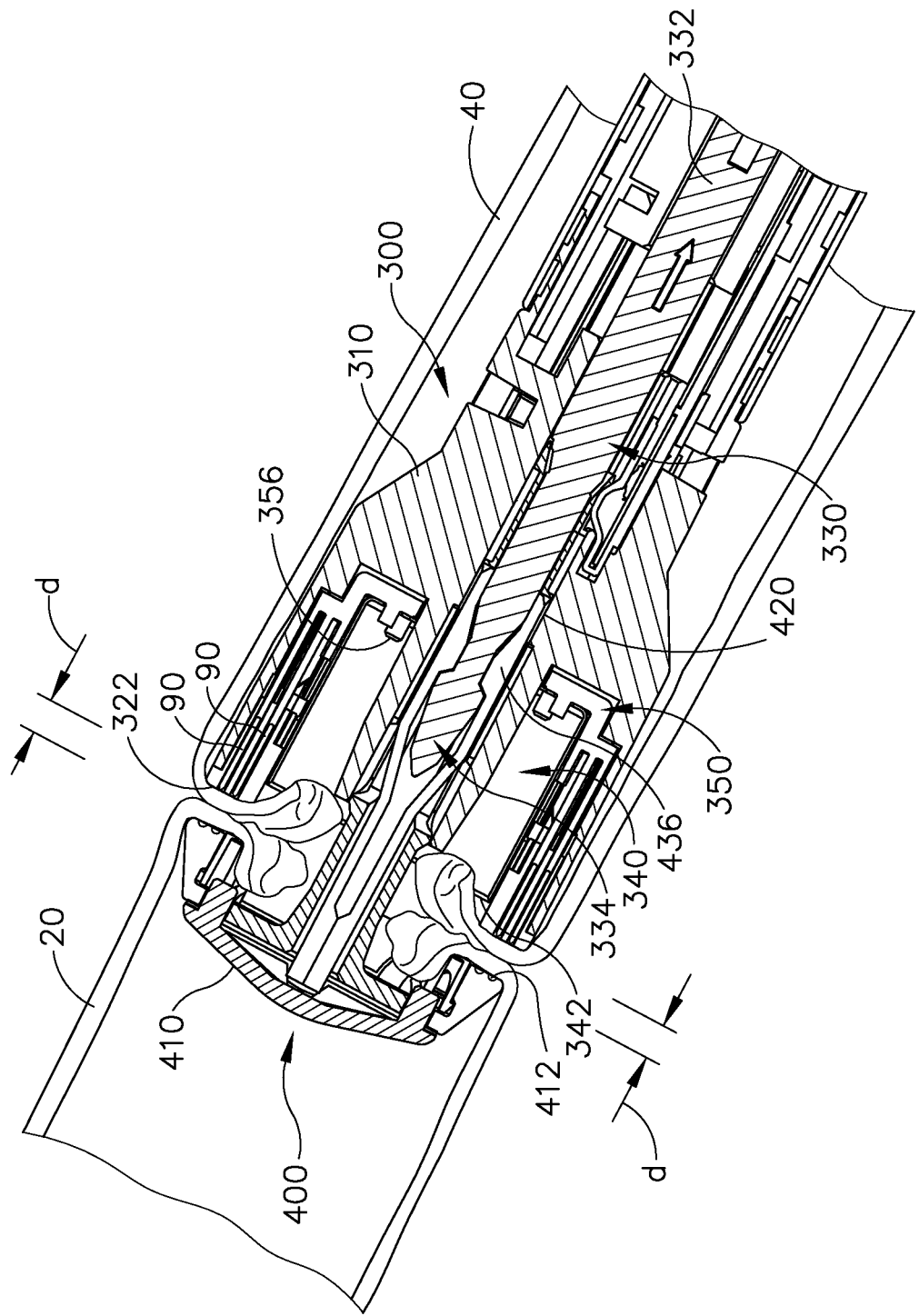
FIG. 21C depicts a cross-sectional side view of the anvil of FIG. 3 positioned within the first section of the digestive tract and the stapling head assembly of FIG. 6 positioned in the second section of the digestive tract, with the anvil retracted toward the stapling head assembly to thereby clamp tissue between the anvil and the stapling head assembly.

FIGS. 21A-21E show instrument (10) being used to form an anastomosis (70) between two tubular anatomical structures (20, 40). By way of example only, the tubular anatomical structures (20, 40) may comprise sections of a patient's esophagus, sections of a patient's colon, other sections of the patient's digestive tract, or any other tubular anatomical structures. As shown in FIG. 21A, anvil (400) is positioned in one tubular anatomical structure (20) and stapling head assembly (300) is positioned in another tubular anatomical structure (40). In versions where tubular anatomical structures (20, 40) comprise sections of a patient's colon, stapling head assembly (300) may be inserted via the patient's rectum. It should also be understood that the procedure depicted in FIGS. 21A-21E is an open surgical procedure, though the procedure may instead be performed laparoscopically. Various suitable ways in which instrument (10) may be used to form an anastomosis (70) in a laparoscopic procedure will be apparent to those of ordinary skill in the art in view of the teachings herein.

As shown in FIG. 21A, anvil (400) is positioned in tubular anatomical structure (20) such that shank (420) protrudes from the open severed end (22) of tubular anatomical structure (20). A purse-string suture (30) is provided about a mid-region of shank (420) to generally secure the position of anvil (400) in tubular anatomical structure (20). Similarly, stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40).

Next, anvil (400) is secured to trocar (330) by inserting trocar (330) into bore (422) as shown in FIG. 21B. Latch members (430) engage head (334) of trocar (330), thereby providing a secure fit between anvil (400) and trocar (330). The operator then rotates knob (130) while holding casing (110) stationary via pistol grip (112). This rotation of knob (130) causes trocar (330) and anvil (400) to retract proximally (as described above with reference to FIGS. 12A-12C). As shown in FIG. 21C, this proximal retraction of trocar (330) and anvil (400) compresses the tissue of tubular anatomical structures (20, 40) between surfaces (412, 322) of anvil (400) and stapling head assembly (300). The operator observes the position of needle (526) within window (114) to determine whether the gap distance (d) between opposing surfaces (412, 322) of anvil (400) and stapling head assembly (300) is appropriate; and makes any necessary adjustments via knob (130).

Figure 21D:
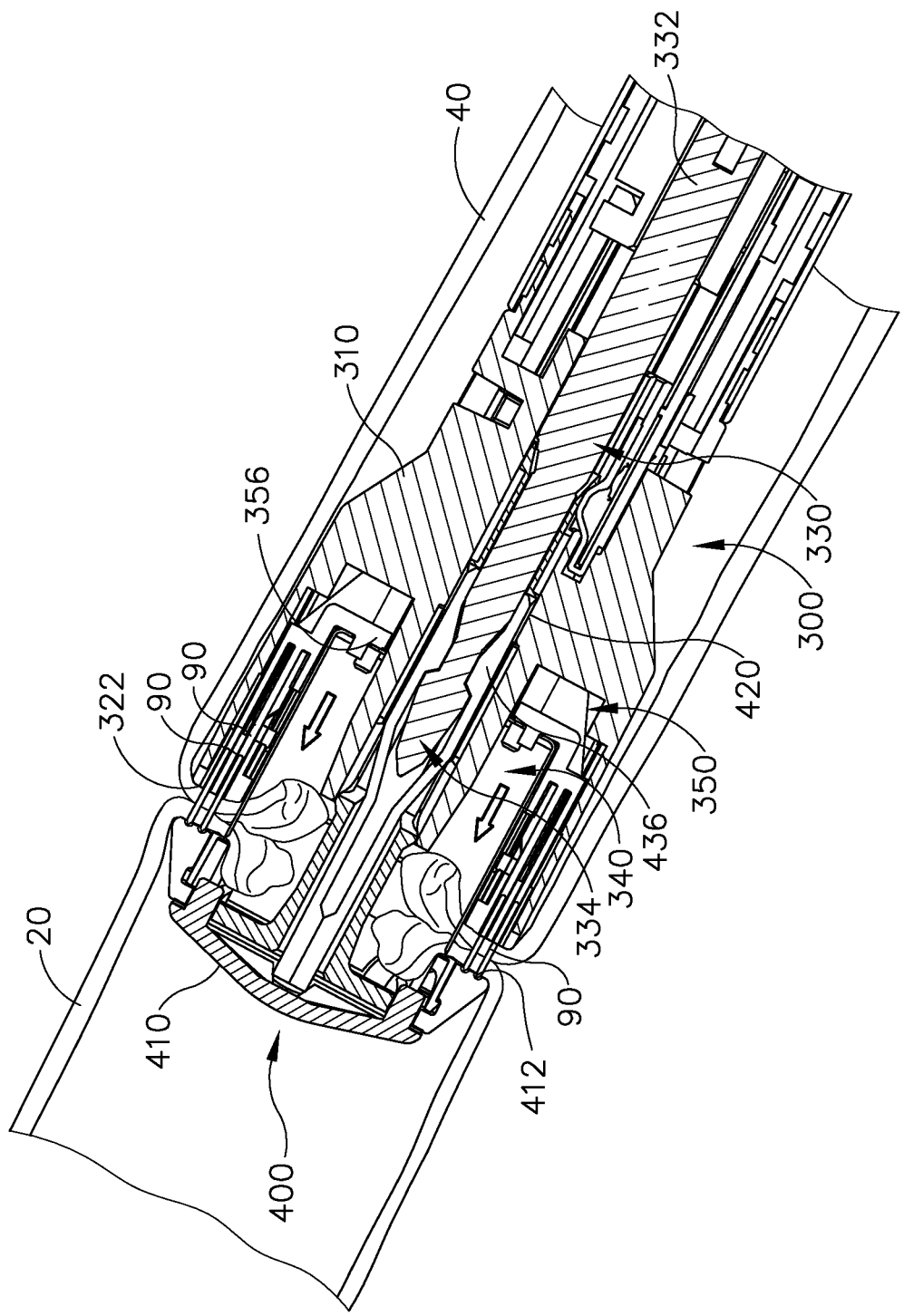
FIG. 21D depicts a cross-sectional side view of the anvil of FIG. 3 positioned within the first section of the digestive tract and the stapling head assembly of FIG. 6 positioned in the second section of the digestive tract, with the stapling head assembly actuated to sever and staple the clamped tissue.

Once the operator has appropriately set the gap distance (d) via knob (130), the operator actuates safety trigger (140) (as shown in FIG. 12D) to enable actuation of firing trigger (150). The operator then actuates firing trigger (150) (as shown in FIG. 12D). This causes paddle (158) to actuate the switch of a motor activation module (180), thereby activating motor to rotate cam member (700) (as shown in FIGS. 20A-20D). This rotation of cam member (700) actuates stapling head assembly (300) by driving knife member (340) and staple driver member (350) distally as shown in FIG. 21D. As knife member (340) translates distally, cutting edge (342) of knife member (340) cooperates with inner edge (416) of anvil (400), thereby shearing excess tissue that is positioned within annular recess (418) of anvil (400) and the interior of knife member (340).

As shown in FIG. 4, anvil (400) of the present example includes a breakable washer (417) within annular recess (418). This washer (417) is broken by knife member (340) when the knife member (340) completes a full distal range of motion from the position shown in FIG. 21C to the position shown in FIG. 21D. The progressively increasing radius of curvature of second surface region may provide an increasing mechanical advantage as knife member (340) reaches the end of its distal movement, thereby providing greater force by which to break the washer (417). Of course, the breakable washer (417) may be omitted entirely in some versions. In versions where washer (417) is included, it should be understood that washer (417) may also serve as a cutting board for knife member (340) to assist in cutting of tissue. Such a cutting technique may be employed in addition to or in lieu of the above-noted shearing action between inner edge (416) and knife member (340).

As staple driver member (350) translates distally from the position shown in FIG. 21C to the position shown in FIG. 21D, staple driver member (350) drives staples (90) through the tissue of tubular anatomical structures (20, 40) and into staple forming pockets (414) of anvil (400). Staple forming pockets (414) deform the driven staples (90) into a "B" shape as is known in the art. The formed staples (90) thus secure the ends of tissue together.

Figure 21E:
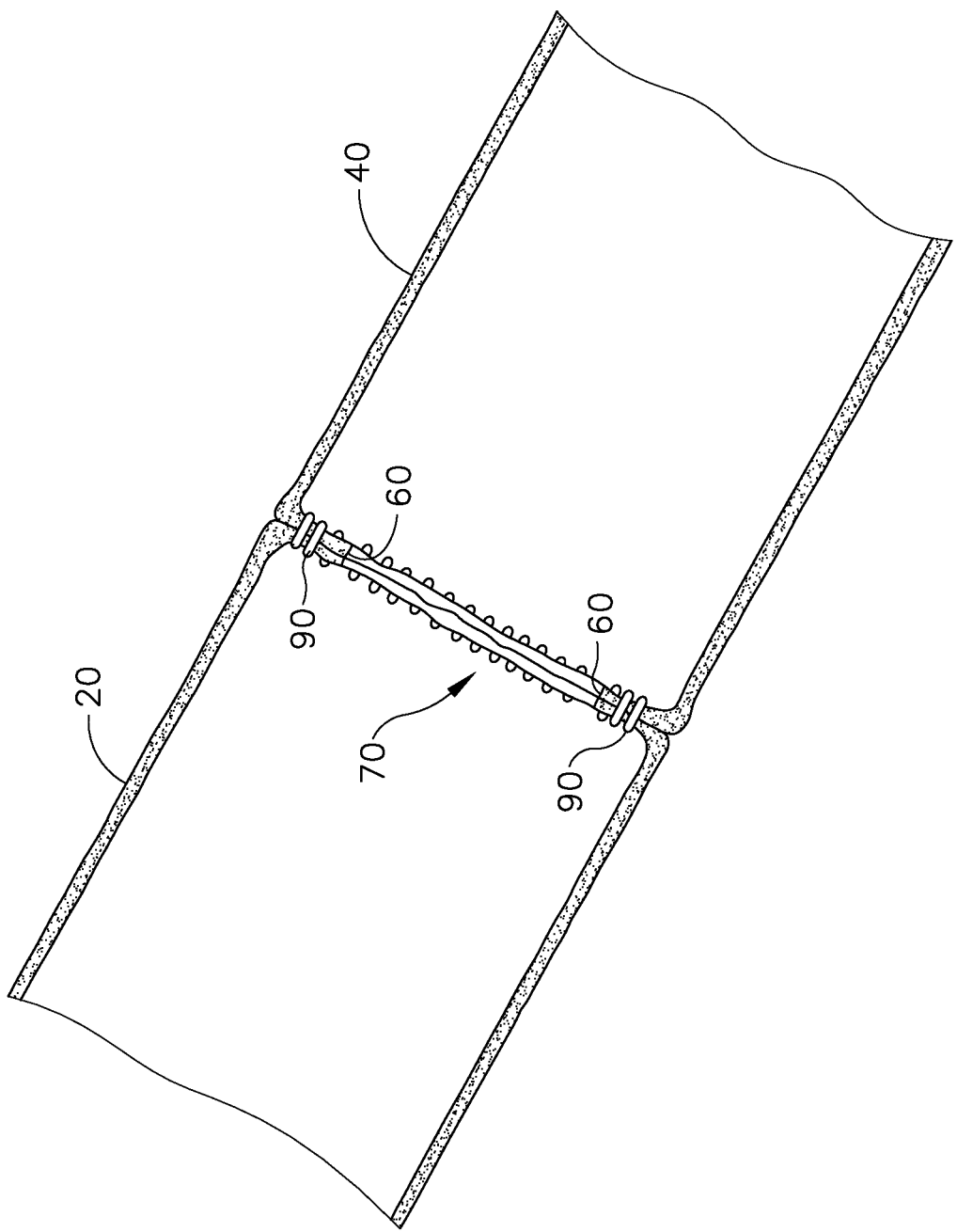
FIG. 21E depicts a cross-sectional side view of the first and second sections of the digestive tract of FIG. 21A joined together at an end-to-end anastomosis.

After the operator has actuated stapling head assembly (300) as shown in FIG. 21D, the operator rotates knob (130) to drive anvil (400) distally away from stapling head assembly (300), increasing the gap distance (d) to facilitate release of the tissue between surfaces (412, 322). The operator then removes instrument (10) from the patient, with anvil (400) still secured to trocar (330). Referring back to the example where the tubular anatomical structures (20, 40) comprise sections of a patient's colon, instrument (10) may be removed via the patient's rectum. With instrument (10) is removed, the tubular anatomical structures (20, 40) are left secured together by two annular arrays of staples (90) at an anastomosis (70) as shown in FIG. 21E. The inner diameter of the anastomosis (70) is defined by the severed edge (60) left by knife member (340).

II. Exemplary Alternative Stapling Head Actuation Assemblies

In some instances, it may be desirable to provide an alternative assembly to actuate stapling head assembly (300). Such an alternative actuation assembly may be integrated into instrument (10) in place of the actuation assembly shown in FIGS. 13-20D and described above. Such an alternative actuation assembly may be driven by motor (160) and may provide both distal translation of stapling head assembly driver (240) and proximal translation of stapling head assembly driver (240) in response to rotation by motor (160) in just a single angular direction (e.g., through an angular range of just less than 360°). Such an alternative actuation assembly may also be used in conjunction with gearbox (162) or may permit gearbox (162) to be omitted altogether. Regardless, such an alternative actuation assembly may be capable of providing a high drive load that is sufficient to fully actuate stapling head assembly (300), including breakage of a breakable washer within annular recess (418) of anvil (400) if such an anvil (400) is used. Several merely illustrative examples of alternative assemblies to actuate stapling head assembly (300) are described in greater detail below. It should be understood that the assemblies described below may be readily incorporated into instrument (10) in place of the actuation assembly shown in FIGS. 13-20D and described above.

A. Rotary Link Based Firing and Return System

Figure 22:
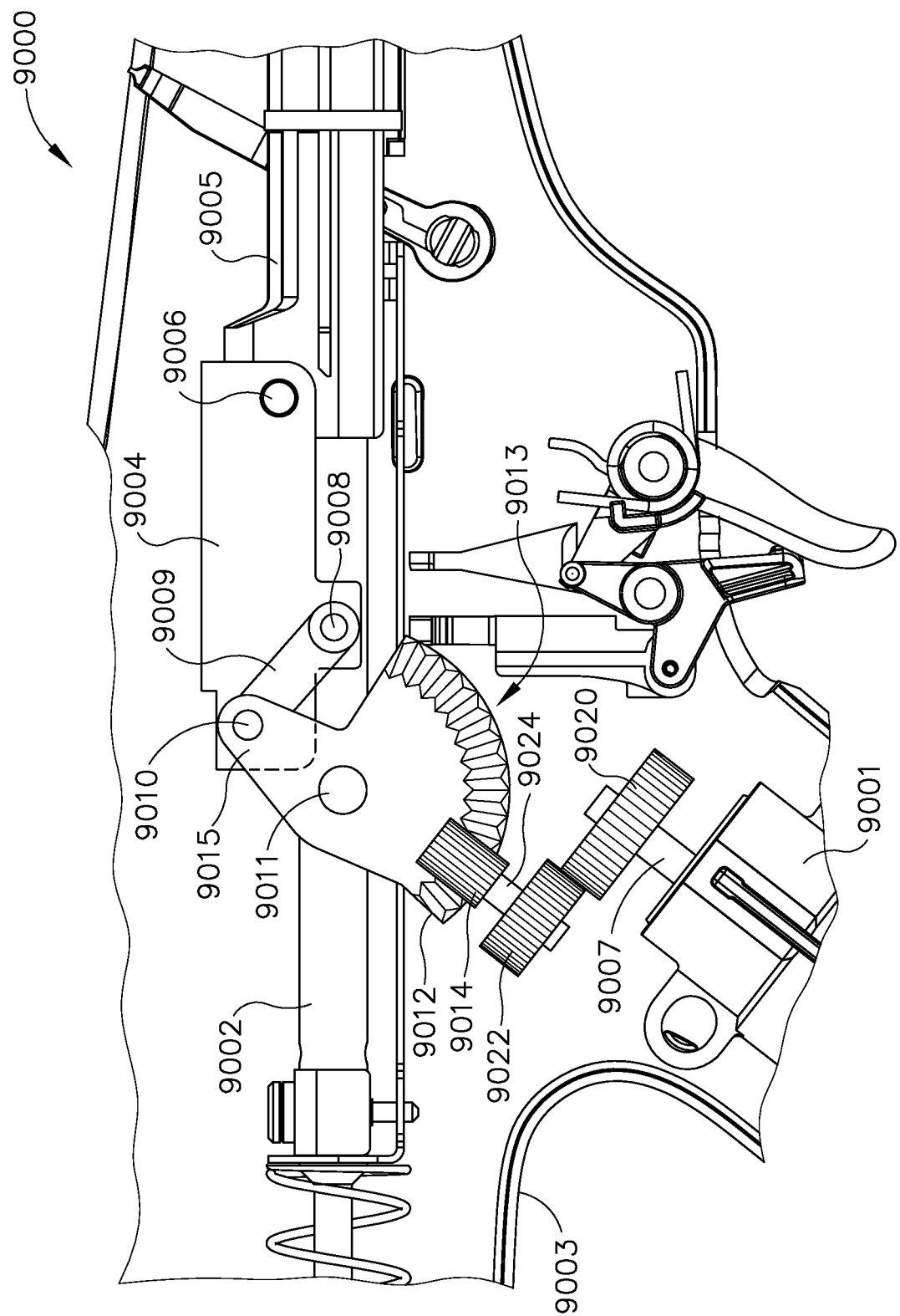
FIG. 22 depicts a side elevational view of an alternative stapling head actuation assembly that may be incorporated into the circular stapler of FIG. 1.

FIG. 22 shows various components of a stapling head actuation assembly (9000) that is operable to actuate stapling head assembly (300). These components include a motor (9001), a motor drive shaft (9007) that is driven by motor (9001), a primary drive gear (9022), an idler gear (9022), an idler shaft (9024), a secondary drive gear (9014), a rotary member (9013), a link (9009), a drive bracket (9004), and a stapling head assembly driver (9005). Motor (9001) is similar to motor (160) described above. In particular, motor (9001) is coupled with motor drive shaft (9007) and is further coupled with drive gear (9020). Therefore, activation of a motor (9001) causes rotation of drive gear (9020). Various suitable configurations that may be used for motor (9001) will be apparent to those of ordinary skill in the art in view of the teachings herein.

Figure 23A:
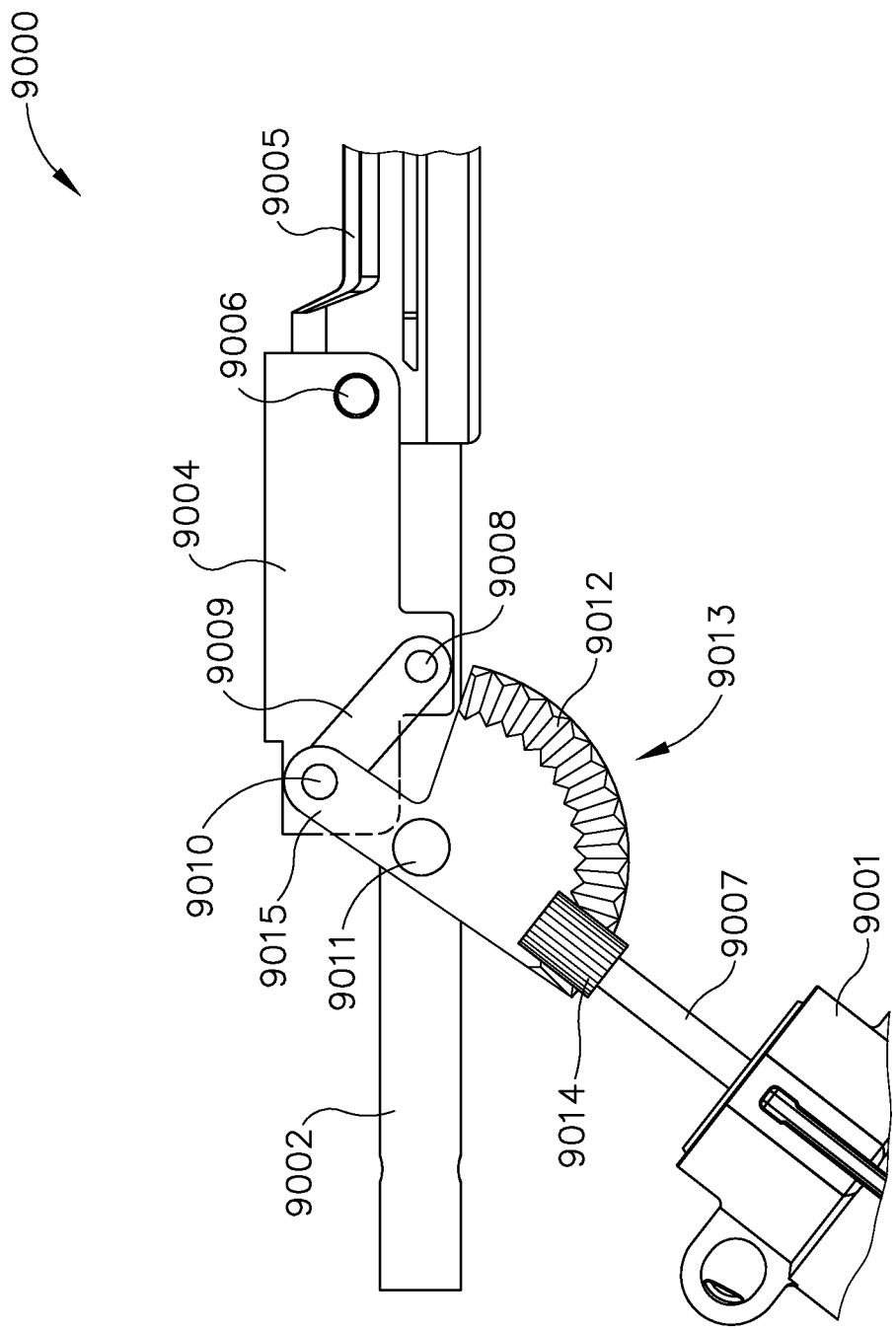
FIG. 23A depicts a partial side elevational view the stapling head actuation assembly of FIG. 22, with a rotary member in a first angular position and a drive bracket in a first linear position.
Figure 23B:
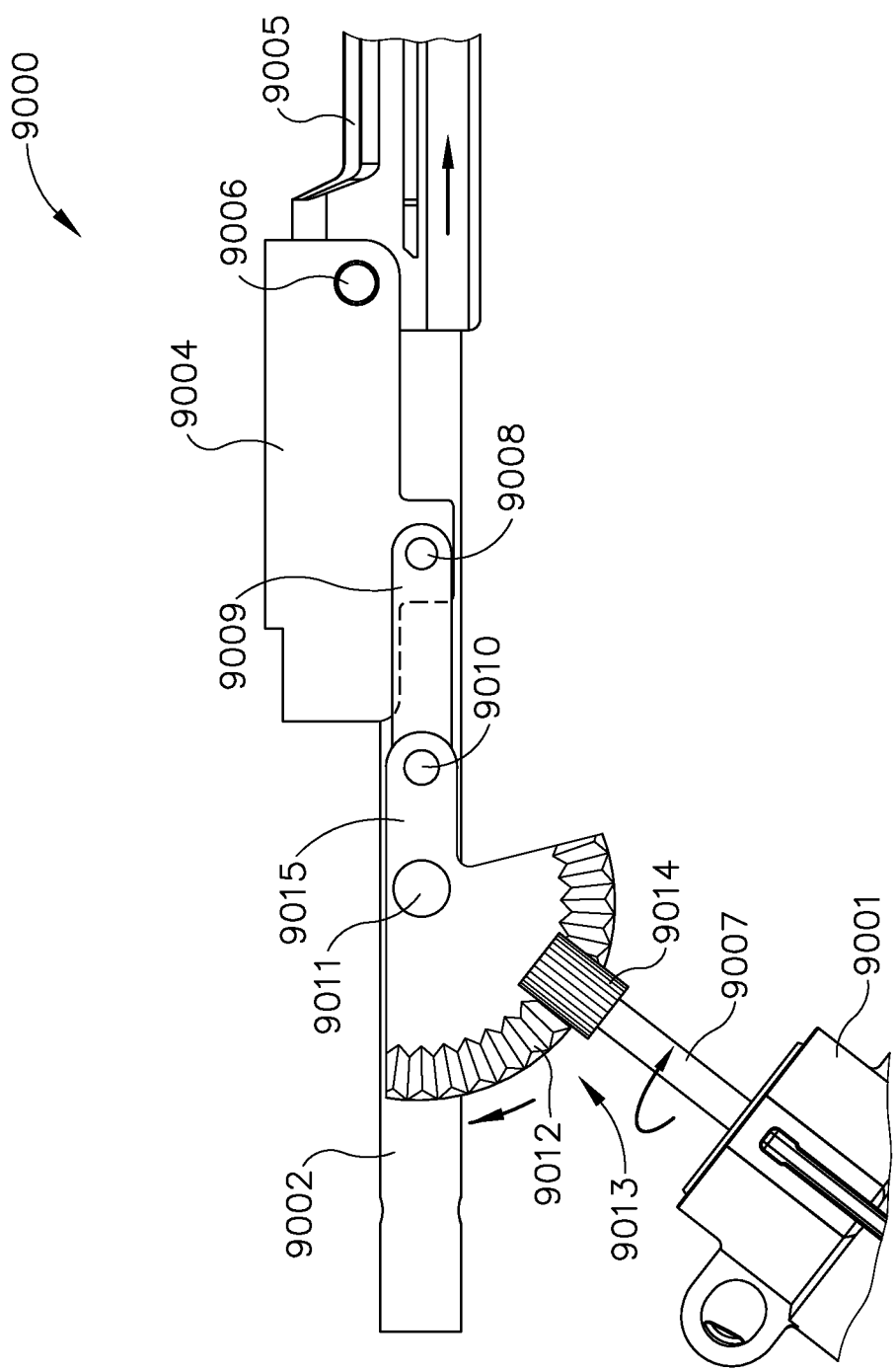
FIG. 23B depicts a partial side elevational view of the stapling head actuation assembly of FIG. 22, with the rotary member in a second angular position and the drive bracket in a second linear position.
Figure 23C:
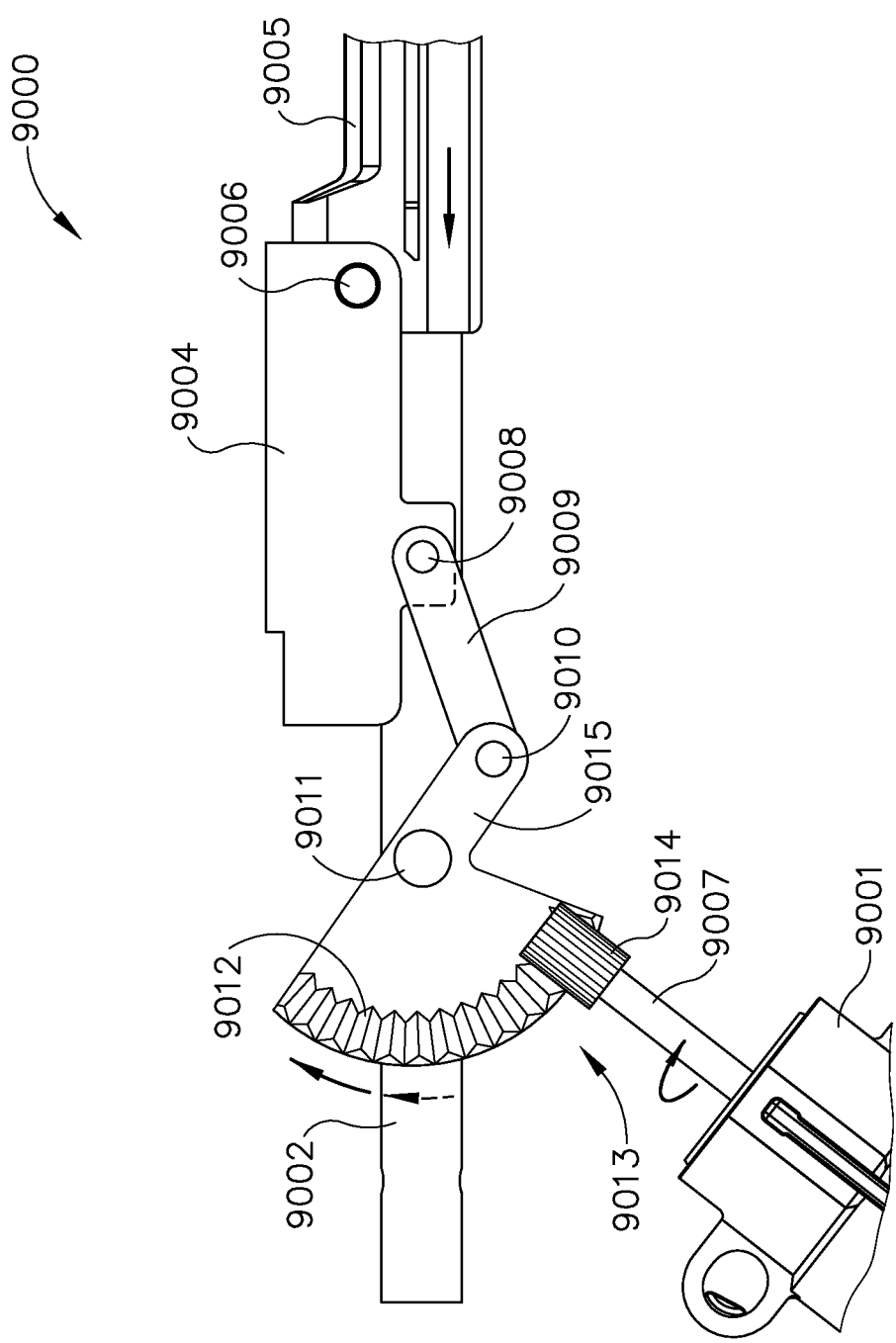
FIG. 23C depicts a partial side elevational view of the stapling head actuation assembly of FIG. 22, with the rotary member in a third angular position and the drive bracket in a third linear position.

In the present example, assembly (9000) lacks a gearbox that is analogous to gearbox (162), though it should be understood that a gearbox and/or any other suitable components may be interposed between motor (9001) and drive gear (9020) to provide desired operational characteristics (e.g., torque, speed, etc.). Idler gear (9022) meshes with drive gear (9020) such that rotation of drive gear (9020) will rotate idler gear (9022). Idler gear (9022) is fixedly secured to idler shaft (9024). Drive gear (9014) is also fixedly secured to idler shaft (9024). It should therefore be understood that rotation of drive gear (9020) will rotate drive gear (9014) via idler gear (9022) and idler shaft (9024). Of course, any other suitable components may be interposed between motor (9001) and drive gear (9014). For instance, FIGS. 23A-23C show a variation of stapling head actuation assembly (9000) where gears (9020, 9022) and idler shaft (9024) are omitted. In this variation, drive gear (9014) is secured to drive shaft (9007) and is thereby driven directly by motor (9001).

In the version of stapling head actuation assembly (9000) shown in FIG. 22 and the version of stapling head actuation assembly (9000) shown in FIGS. 23A-23C, rotary member (9013) is pivotably fixed to casing (9003) via pin (9011). Drive gear (9014) is configured to rotate rotary member (9013) in a clockwise angular direction about a pin (9011) as will be described in greater detail below. Pin (9011) is coupled with casing (9003), such that rotary member (9013) is only capable of rotating relative to casing (9003). Casing (9003) of this example is substantially similar to casing (110) described above.

Trocar actuation rod (9002) is substantially similar to trocar actuation rod (220) described above. In the present example, trocar actuation rod (9002) is presumed to be located at a position to define a desirable "clinically acceptable range" for gap distance (d). So while trocar actuation rod (9002) is in fact movable, trocar actuation rod (9002) is assumed to be stationary through the stages shown in FIGS. 23A-23C.

Drive bracket (9004) is substantially similar to drive bracket (250) described above, except that drive bracket (9004) is pivotably coupled to link (9009) via pin (9008) instead of being pivotably coupled to cam follower (600). Drive bracket (9004) is fixed to stapling head assembly driver (9005) via pin (9006). However, drive bracket (9004) and stapling head assembly driver (9005) may instead be formed as a single unitary piece if desired. Stapling head assembly driver (9005) is substantially similar to stapling head assembly driver (240) described above. Therefore, it should be understood that staple driver member (350) will translate longitudinally relative to trocar actuation rod (9002) in response to translation of stapling head assembly driver (9005) and drive bracket (9005) relative to trocar actuation rod (9002).

Rotary member (9013) includes a semi-annular array of laterally presented teeth (9012) on one side of pin (9011) and a rotary arm (9015) on the other side of pin (9011). Teeth (9012) extend along a quarter-pie angular range perimeter of rotary member (9013). Teeth (9012) are configured to complement drive gear (9014) in such a way that rotation of drive gear (9014) drives rotary member (9013) in an angular direction about pin (9011). Once drive gear (9014) reaches the termination of the quarter-pie perimeter of rotary member (9013), drive gear (9014) and teeth (9013) may disengage in such a manner that rotary member (9013) is no longer is capable of engaging drive gear (9014). After drive gear (9014) and teeth (9013) disengage, rotary member (9013) is then incapable of angular movement about pin (9011). In the present example, however, motor (9001) is not activated in a manner that would provide disengagement of drive gear (9014) from teeth (9013). Instead, motor (9001) is deactivated before drive gear (9014) disengages teeth (9013).

Rotary arm (9015) extends generally tangentially in relation to pin (9011) and pivotably couples to link (9009) via pin (9010). Link (9009) is also pivotably coupled to drive bracket (9004) via pin (9008). While rotary member (9013) is limited to rotational movement about pin (9011), and drive bracket (9004) is limited to linear translation relative to outer sheath (210), link (9009) is capable of both linear translation and rotation. Therefore, link (9009) converts the angular movement of rotary member (9013) into linear movement of drive bracket (9004). In other words, the angular position of rotary member (9013) directly corresponds to a linear position of drive bracket (9004).

FIGS. 23A-23C schematically depict the interaction between drive gear (9014), rotary member (9013), link (9009), drive bracket (9004), and stapling head assembly driver (9005). It should be understood that the rotation of drive gear (9014) throughout the stages shown in FIGS. 23A-23C is driven by motor (9001). It should also be understood that the variation of stapling head actuation assembly (9000) shown in FIG. 22 will operate substantially identically to the variation of stapling head actuation assembly (9000) shown in FIGS. 23A-23C.

FIG. 23A shows stapling head actuation assembly (9000) in a first, pre-firing configuration. Drive gear (9014) is located on a proximal portion of the semi-annular array of teeth (9012). The angular location of rotary member (9013), and therefore the angular location of rotary arm (9015) as shown in FIG. 23A corresponds to the most proximal location of drive bracket (9004). At this stage, the proximal end of link (9009), as defined by pin (9010) is located at its highest vertical placement relative to the distal end of link (9009), as defined by pin (9008). At this stage, knife member (340) and staple driver member (350) are in proximal positions, such that stapling head assembly driver (9005) and therefore stapling head assembly (300) are in a non-actuated state.

As drive gear (9014) is rotated by motor drive shaft (9007), this causes drive gear (9014) to travel along the semi-annular array of teeth (9012), thereby rotating rotary member (9013) about pin (9011) to the position shown in FIG. 23B. The angular location of rotary member (9013), and therefore the angular location of rotary arm (9015) as shown in FIG. 23B, corresponds to the most distal location of drive bracket (9004). Rotary member (9013) and link (9009) thus drive knife member (340) and staple driver member (350) distally via drive bracket (9004) and stapling head assembly driver (9005). Stapling head assembly (300) is thus in an actuated state at the stage shown in FIG. 23B.

In the present example, drive gear (9014) is located at a position that is approximately mid-way along the length of the semi-annular array of teeth (9012) at the stage shown in FIG. 23B.

At the stage shown in FIG. 23B, pins (9008, 9010, 9011) are aligned with each other along a single axis. It is important to note that at this point, the proximal end of link (9009), as defined by pin (9010) is located at the same vertical level relative to the distal end of link (9009), as defined by pin (9008). This occurs because vertically fixed pins (9011, 9008) are located at the same vertical level. While this placement is optional, it may provide optimal torque to force transfer while knife member (340) and staple driver member (350) are in their most distal position, helping ensure knife member (340) and staple driver member (350) properly operate. However, as described below, this placement of vertically fixed pins (9011, 9008) is optional.

After stapling head assembly (300) has been actuated through a full distal drive stroke as shown in the transition from FIG. 23A to FIG. 23B, drive gear (9014) continues to rotate in the same angular direction, therefore rotating rotary member (9013) to the position shown in FIG. 23C. At this stage, rotary arm (9015) and link (9009) have pulled drive bracket (9004) and stapling head assembly driver (9005) proximally. The proximal end of link (9009), at pin (9010), is located at a vertical level that is lower than the vertical level of the distal end of link (9009), at pin (9008). At this stage, knife member (340) and staple driver member (350) are back to proximal positions, such that stapling head assembly driver (9005) and therefore stapling head assembly (300) are back in a non-actuated state. In the present example, drive gear (9014) is located at the distal end of the semi-annular array of teeth (9012) at the stage shown in FIG. 23C.

Optionally, rotary gear (9014) may keep rotating past the location shown on FIG. 23C so that teeth (9012) disengage from drive gear (9014). This may help ensure that actuation of knife member (340) and staple driver member (350) only occurs once. Additionally or alternatively, motor (9001) may be utilized to rotate drive shaft (9007) in one direction. Therefore, the quarter-pie array of teeth (9012) ensures that actuation of knife member (340) and staple driver member (350) only occurs once.

Figure 24A:
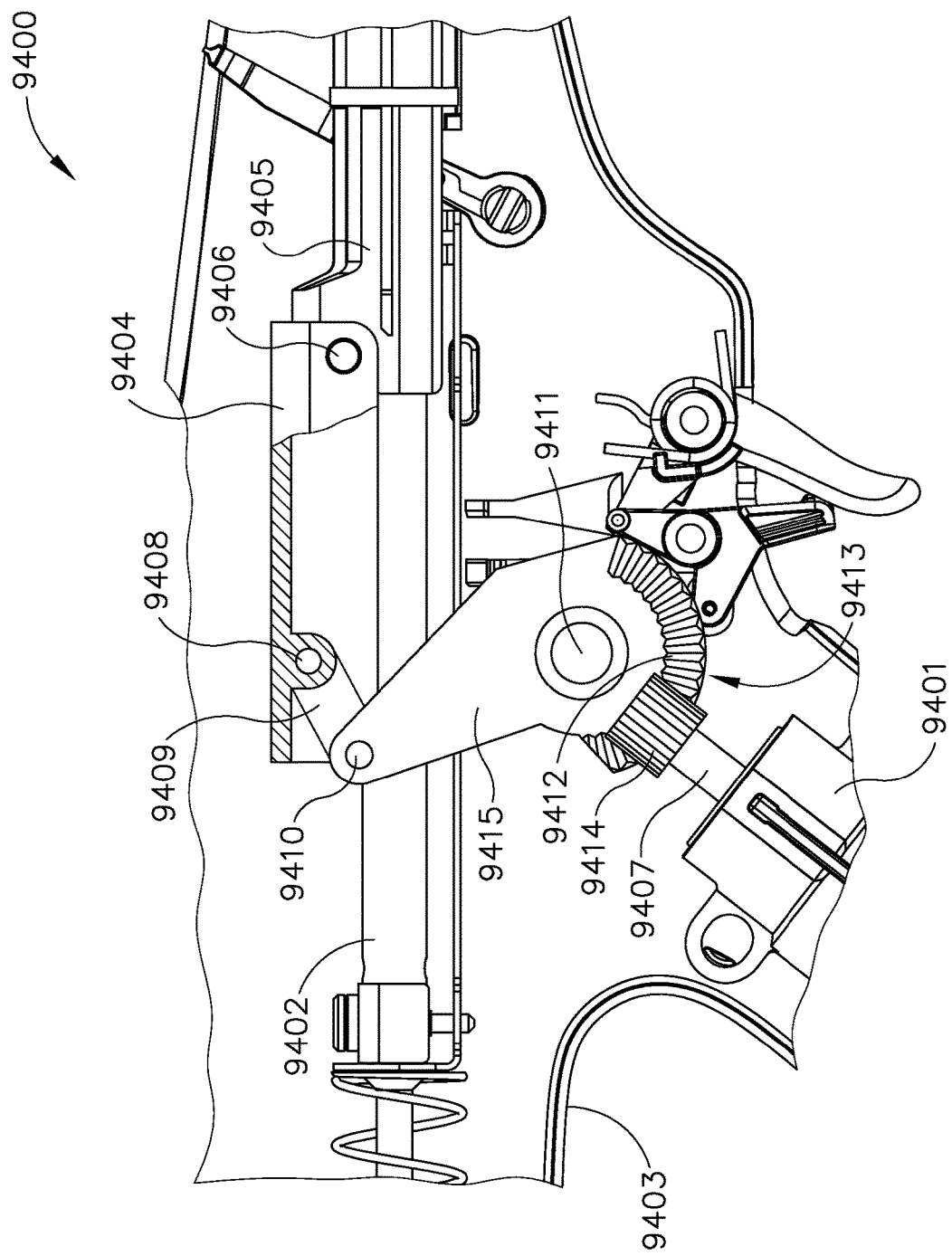
FIG. 24A depicts a partial side elevational view of another alternative stapling head actuation assembly that may be incorporated into the circular stapler of FIG. 1, with a rotary member in a first angular position and a drive bracket in a first linear position.
Figure 24B:
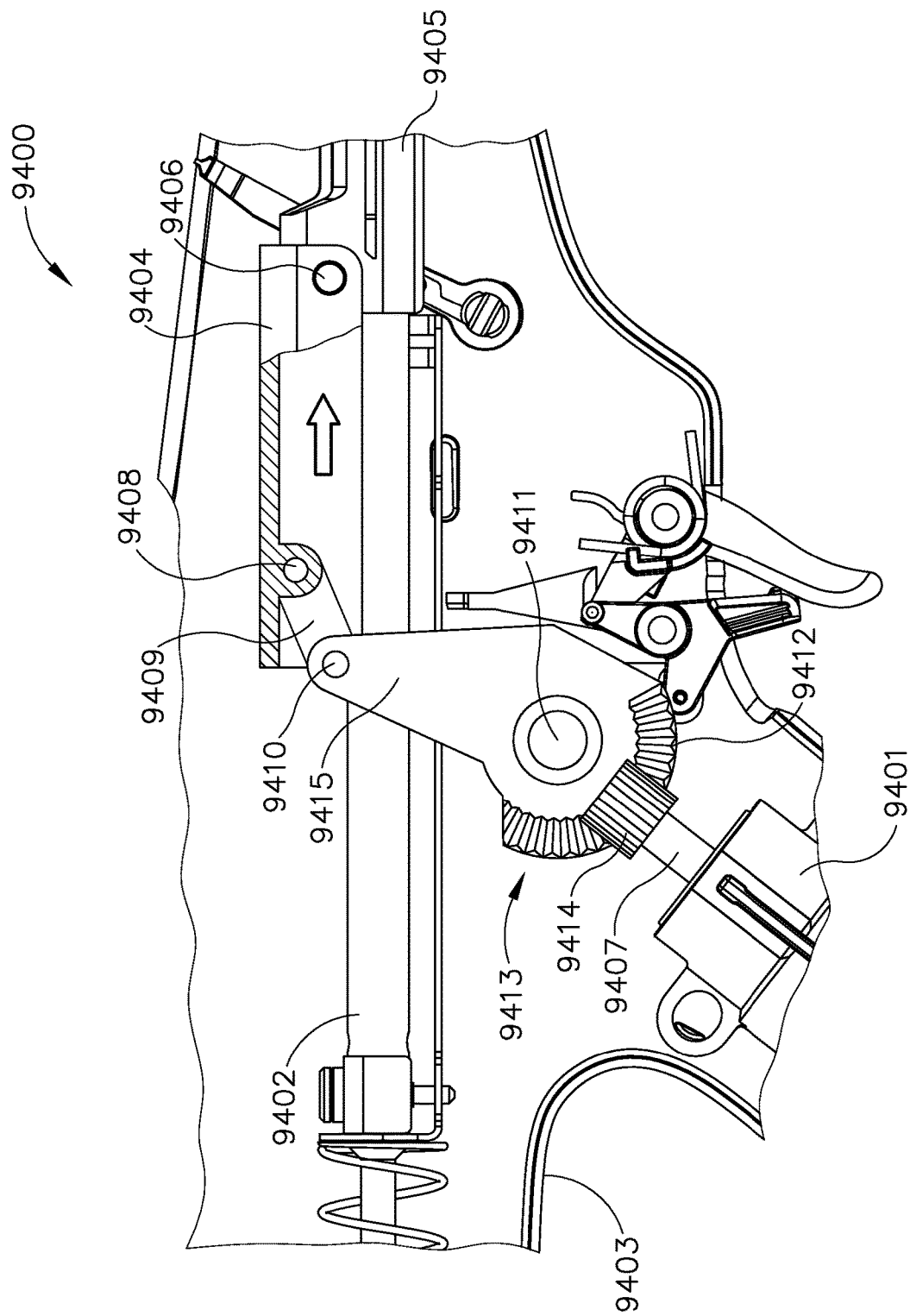
FIG. 24B depicts a partial side elevational view of the stapling head actuation assembly of FIG. 24A, with the rotary member in a second angular position and the drive bracket in a second linear position.
Figure 24C:
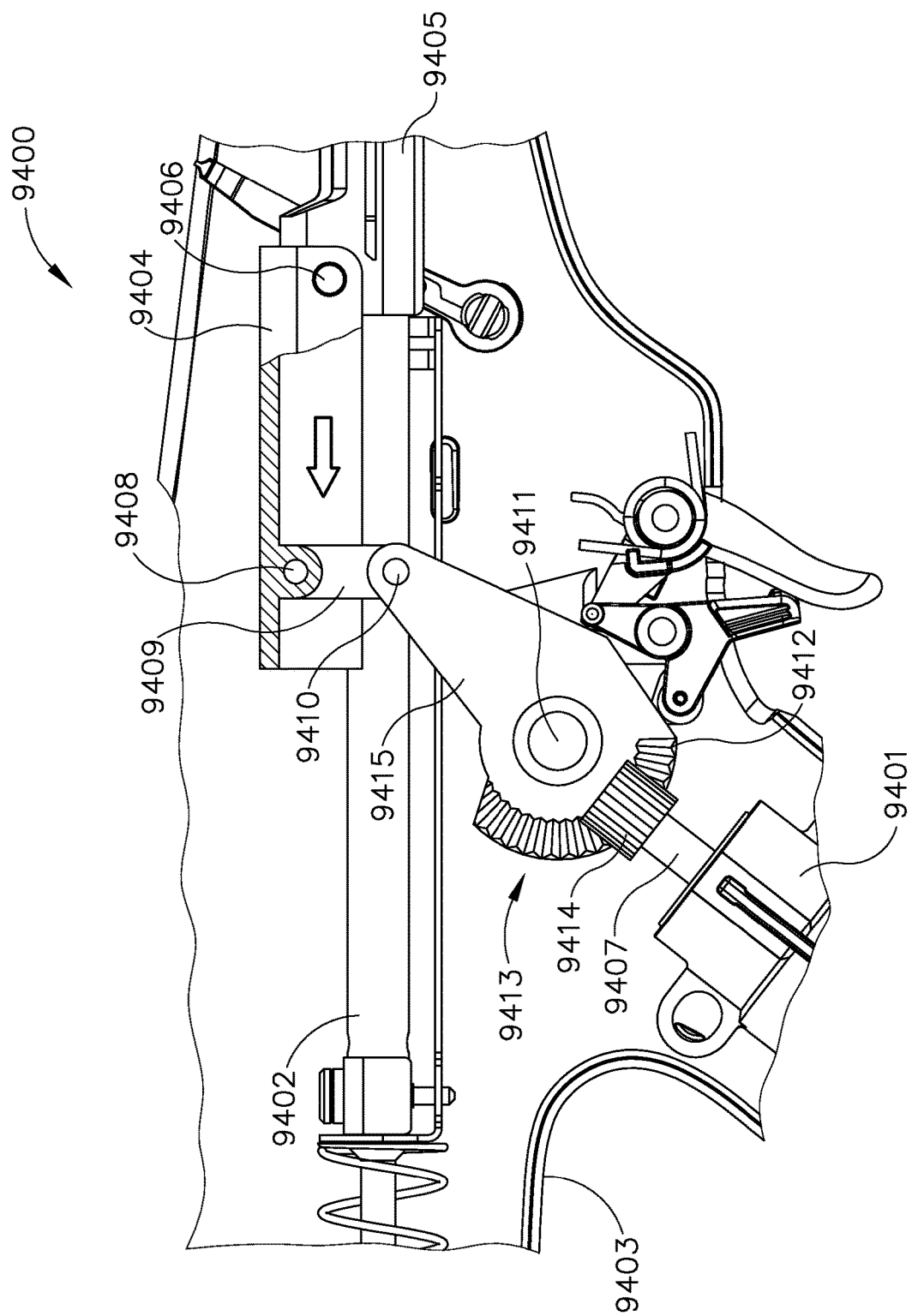
FIG. 24C depicts a partial side elevational view of the stapling head actuation assembly of FIG. 24A, with the rotary member in a third angular position and the drive bracket in a third linear position

FIGS. 24A-24C show various components of another exemplary stapling head actuation assembly (9400) that is operable to actuate stapling head assembly (300). These components include a motor (9401), a motor drive shaft (9407) that is driven by motor (9401), a drive gear (9414), a rotary member (9413), a link (9409), a drive bracket (9404), and a stapling head assembly driver (9405). Motor (9401) is similar to motor (160) described above. In particular, motor (9401) is coupled with motor drive shaft (9407) and is further coupled with drive gear (9414). Therefore, activation of motor (9401) causes rotation of drive gear (9414). Various suitable configurations that may be used for motor (9401) will be apparent to those of ordinary skill in the art in view of the teachings herein. In the present example, assembly (9400) lacks a gearbox that is analogous to gearbox (162), though it should be understood that a gearbox and/or any other suitable components may be interposed between motor (9401) and drive gear (9414) to provide desired operational characteristics (e.g., torque, speed, etc.).

Rotary member (9413) is pivotably fixed to casing (9403) via pin (9411). Drive gear (9414) is configured to rotate rotary member (9413) in an angular direction about a pin (9411) as will be described in greater detail below. Pin (9411) is coupled with casing (9403), such that rotary member (9413) is only capable of rotating relative to casing (9403). Casing (9403) is substantially similar to casing (110) described above.

Trocar actuation rod (9402) is substantially similar to trocar actuation rod (220) described above. In the present example, trocar actuation rod (9402) is presumed to be located at a position to define a desirable "clinically acceptable range" for gap distance (d). So while trocar actuation rod (9402) is in fact movable, trocar actuation rod (9402) is assumed to be stationary through the stages shown in FIGS. 24A-24C.

Drive bracket (9404) is substantially similar to drive bracket (250) described above, except that drive bracket (9404) is pivotably coupled to link (9409) via pin (9408) instead of being pivotably coupled to cam follower (600). Drive bracket (9404) is fixed to stapling head assembly driver (9405) via pin (9406). However, drive bracket (9404) and stapling head assembly driver (9405) may instead be formed as a single unitary piece if desired. Stapling head assembly driver (9405) is substantially similar to stapling head assembly driver (240) described above. Therefore, it should be understood that staple driver member (350) will translate longitudinally relative to trocar actuation rod (9402) in response to translation of stapling head assembly driver (9405) and drive bracket (9405) relative to trocar actuation rod (9402).

Rotary member (9413) includes a semi-annular array of laterally presented teeth (9412) on one side of pin (9411) and a rotary arm (9415) on the other side of pin (9411). Teeth (9412) extend along a quarter-pie angular range along the perimeter of rotary member (9413). Teeth (9412) are configured to complement drive gear (9414) in such a way that rotation of drive gear (9414) drives rotary member (9413) in an angular direction about pin (9411). Once drive gear (9414) reaches the termination of the array of teeth (9412), drive gear (9414) and teeth (9412) may disengage in such a manner that rotary member (9413) is no longer is capable of engaging drive gear (9414). After drive gear (9414) and teeth (9412) disengage, rotary member (9413) is then incapable of angular movement about pin (9411). In the present example, however, motor (9401) is not activated in a manner that would provide disengagement of drive gear (9414) from teeth (9412). Instead, motor (9401) is deactivated before drive gear (9414) disengages teeth (9412).

Rotary arm (9415) extends outwardly relative to pin (9411) and pivotably couples to link (9409) via pin (9410). Link (9409) is also pivotably coupled to drive bracket (9404) via pin (9408). While rotary member (9413) is limited to rotational movement about pin (9411) and drive bracket (9404) is limited to linear translation relative to outer sheath (210), link (9409) is capable of both linear translation and rotation. Therefore, link (9409) converts the angular movement of rotary member (9413) into linear movement of drive bracket (9404). In other words, the angular position of rotary member (9413) directly corresponds to a linear position of drive bracket (9404).

FIGS. 24A-24C schematically depict the interaction between drive gear (9414), rotary member (9413), link (9409), drive bracket (9404), and stapling head assembly driver (9405). It should be understood that the rotation of drive gear (9414) throughout the stages shown in FIGS. 24A-24C is driven by motor (9401).

FIG. 24A shows stapling head actuation assembly (9400) in a first, pre-firing configuration. Drive gear (9414) is located on a proximal portion of the semi-annular array of teeth (9412). The angular location of rotary member (9413), and therefore the angular location of rotary arm (9415) as shown in FIG. 24A, corresponds to the most proximal location of drive bracket (9404). At this stage, knife member (340) and staple driver member (350) are in proximal positions, such that stapling head assembly driver (9405) and therefore stapling head assembly (300) are in a non-actuated state.

As drive gear (9414) is rotated by motor drive shaft (9407), this causes drive gear (9414) to travel along the semi-annular array of teeth (9412), thereby rotating rotary member (9413) about pin (9411) to the position shown in FIG. 24B. The angular location of rotary member (9413), and therefore the angular location of rotary arm (9415) as shown in FIG. 24B, corresponds to the most distal location of drive bracket (9404). Rotary member (9413) and link (9409) thus drive knife member (340) and staple driver member (350) distally via drive bracket (9404) and stapling head assembly driver (9405). Stapling head assembly (300) is thus in an actuated state at the stage shown in FIG. 24B. In the present example, drive gear (9414) is located at a position that is approximately mid-way along the length of the semi-annular array of teeth (9412) at the stage shown in FIG. 24B. At the stage shown in FIG. 24B, pins (9408, 9410, 9411) are aligned with each other along a single axis, which is obliquely oriented relative to the longitudinal axis of stapling head assembly driver (9405). This placement is merely optional.

After stapling head assembly (300) has been actuated through a full distal drive stroke as shown in the transition from FIG. 24A to FIG. 24B, drive gear (9414) continues to rotate in the same angular direction, therefore rotating rotary member (9413) to the position shown in FIG. 24C. At this stage, rotary arm (9415) and link (9409) have pulled drive bracket (9404) and stapling head assembly driver (9405) proximally. Thus, at this stage, knife member (340) and staple driver member (350) are back to proximal positions, such that stapling head assembly driver (9405) and therefore stapling head assembly (300) is back in a non-actuated state. In the present example, drive gear (9414) is located at the distal end of the semi-annular array of teeth (9412) at the stage shown in FIG. 24C.

Optionally, rotary gear (9414) may keep rotating past the location shown on FIG. 24C so that teeth (9412) disengage from drive gear (9414). This may help ensure that actuation of knife member (340) and staple driver member (350) only occurs once. Additionally or alternatively, motor (9401) may be utilized to rotate drive shaft (9407) in one direction. Therefore, the quarter-pie array of teeth (9412) ensures that actuation of knife member (340) and staple driver member (350) only occurs once.

B. Rotary Pawl Based Firing and Return System

Figure 25A:
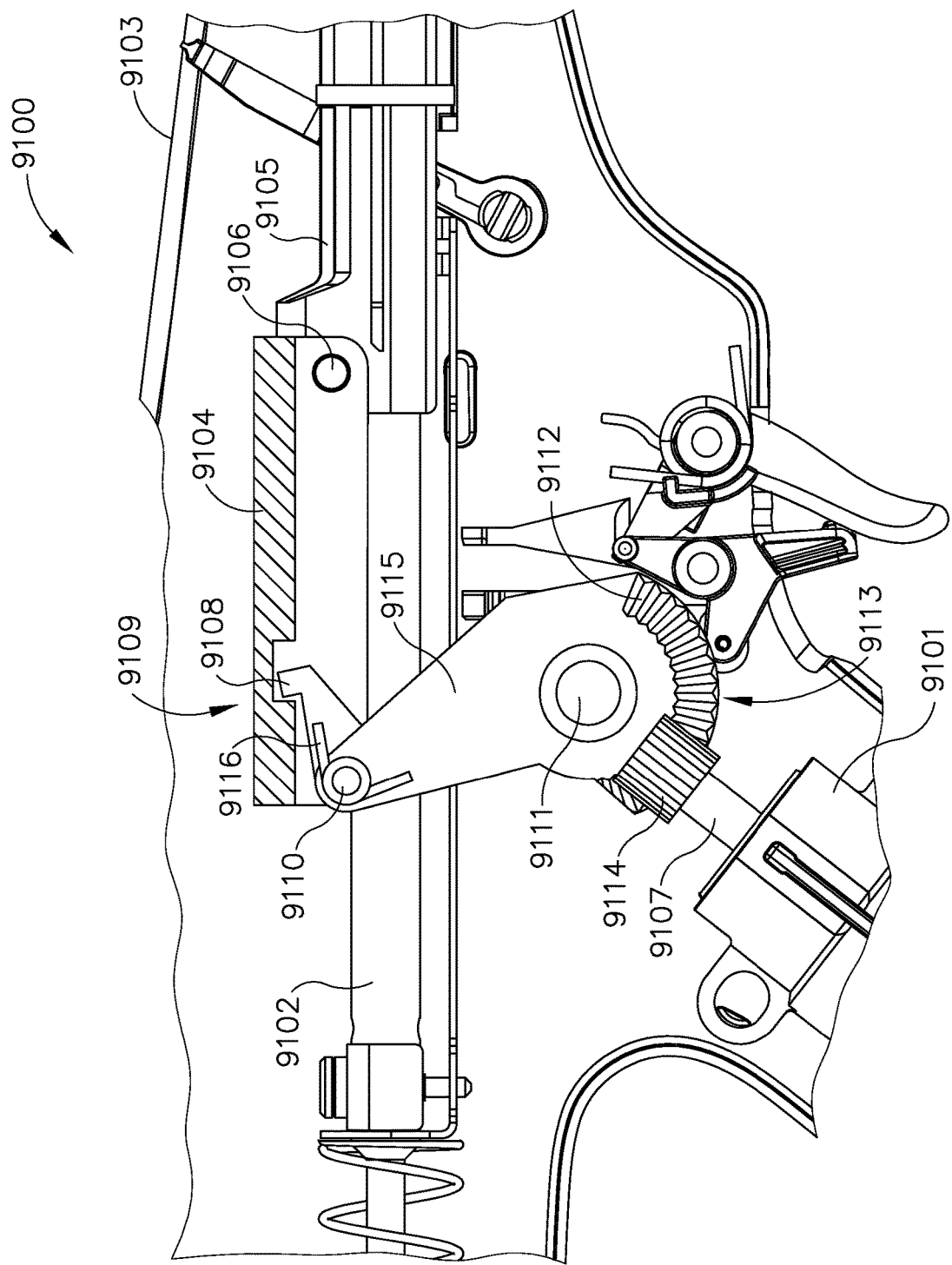
FIG. 25A depicts a partial side elevational view of another alternative stapling head actuation assembly that may be incorporated into the circular stapler of FIG. 1, with a rotary member in a first angular position and a drive bracket in a first linear position.
Figure 25B:
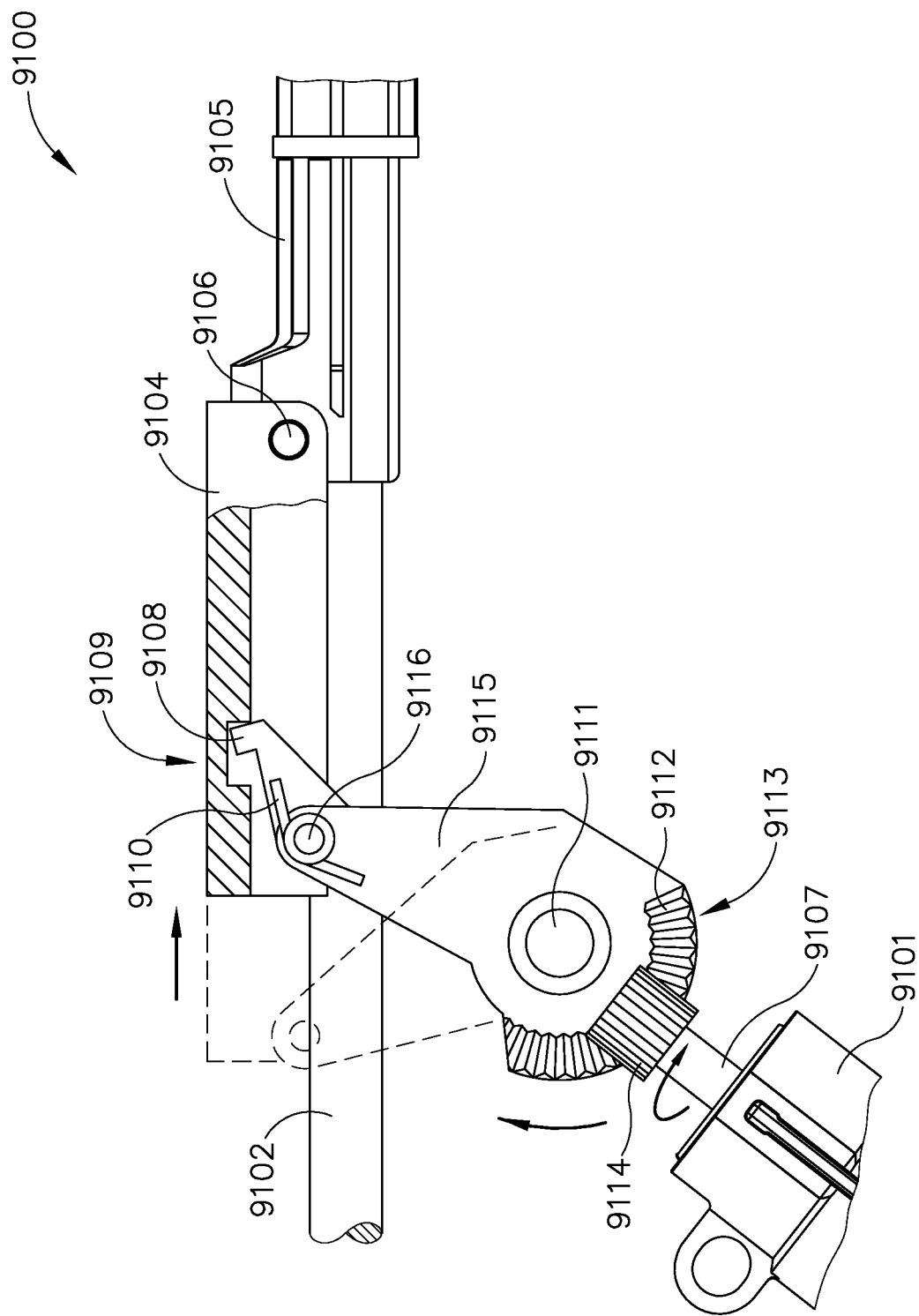
FIG. 25B depicts a partial side elevational view of the stapling head actuation assembly of FIG. 25A, with the rotary member in a second angular position and the drive bracket in a second linear position.

FIGS. 25A-25B show various components of another exemplary stapling head actuation assembly (9100) that is operable to actuate stapling head assembly (300). These components include a motor (9101), a motor drive shaft (9107) that is driven by motor (9101), a drive gear (9114), a rotary member (9113), a pin (9116) coupled to a torsion spring (9110), a drive bracket (9104), and a stapling head assembly driver (9105). Motor (9101) is similar to motor (160) described above. In particular, motor (9101) is coupled with motor drive shaft (9107) and is further coupled with drive gear (9114). Therefore, activation of motor (9101) causes rotation of drive gear (9114). Various suitable configurations that may be used for motor (9101) will be apparent to those of ordinary skill in the art in view of the teachings herein. In the present example, assembly (9100)

lacks a gearbox that is analogous to gearbox (162), though it should be understood that a gearbox and/or any other suitable components may be interposed between motor (9101) and drive gear (9114) to provide desired operational characteristics (e.g., torque, speed, etc.).

Rotary member (9113) is pivotably fixed to casing (9103) via pin (9111). Drive gear (9114) is configured to rotate rotary member (9113) in an angular direction about a pin (9111) as will be described in greater detail below. Pin (9111) is coupled with casing (9103), such that rotary member (9113) is only capable of rotating relative to casing (9103). Casing (9103) is substantially similar to casing (110) described above.

Trocar actuation rod (9102) is substantially similar to trocar actuation rod (220) described above. In the present example, trocar actuation rod (9102) is presumed to be located at a position to define a desirable "clinically acceptable range" for gap distance (d). So while trocar actuation rod (9102) is in fact movable, it is assumed to be stationary through the stages shown in FIGS. 25A-25B.

Drive bracket (9104) is substantially similar to drive bracket (250) described above, except that drive bracket (9104) defines a recess (9109) that receives pawl (9108) instead of being pivotably coupled to cam follower (600). Drive bracket (9104) is fixed to stapling head assembly driver (9105) via pin (9106). However, drive bracket (9104) and stapling head assembly driver (9105) may instead be formed as a single unitary piece if desired. Stapling head assembly driver (9105) is substantially similar to stapling head assembly driver (240) described above. Therefore, it should be understood that staple driver member (350) will translate longitudinally relative to trocar actuation rod (9102) in response to translation of stapling head assembly driver (9105) and drive bracket (9105) relative to trocar actuation rod (9102).

Rotary member (9113) includes a semi-annular array of teeth (9112) on one side of pin (9111) and a rotary arm (9115) on the other side of pin (9111). Teeth (9112) extend along a quarter-pie angular range along the perimeter of rotary member (9113). Teeth (9112) are configured to complement drive gear (9114) in such a way that rotation of drive gear (9114) drives rotary member (9113) in an angular direction about pin (9111). Once drive gear (9014) reaches the termination of the array of teeth (9112), drive gear (9114) and teeth (9112) may disengage in such a manner that rotary member (9113) is no longer is capable of engaging drive gear (9114). After drive gear (9114) and teeth (9112) disengage, rotary member (9113) is then incapable of angular movement about pin (9111). In the present example, however, motor (9101) is not activated in a manner that would provide disengagement of drive gear (9114) from teeth (9112). Instead, motor (9101) is deactivated before drive gear (9114) disengages teeth (9112).

Rotary arm (9115) extends outwardly relative to pin (9111) and pivotably couples to the proximal end of pawl (9108) via pin (9116). Pin (9116) is also coupled to resiliently biased torsion spring (9110). Torsion spring (9110) is attached to both pawl (9108) and rotary arm (9115). Distal end of pawl (9108) is located within recess (9109) of drive bracket (9104). Torsion spring (9110) is positioned in such a way as to bias pawl (9108) against the proximal portion of recess (9109), therefore biasing drive bracket (9104) in a proximal direction.

FIGS. 25A-25B schematically depict the interaction between drive gear (9114), rotary member (9113), pawl (9108), drive bracket (9104), and stapling head assembly driver (9105). It should be understood that the rotation of drive gear (9014) throughout the stages shown in FIGS. 25A-25B is driven by motor (9101).

FIG. 25A shows stapling head actuation assembly (9100) in a first, pre-firing configuration. Drive gear (9114) is located in a proximal portion of the semi-annular array of teeth (9112). The angular location of rotary member (9113), and therefore the angular location of rotary arm (9115) as shown in FIG. 25A, corresponds to the most proximal location of drive bracket (9104). Additionally, as mentioned before, pawl (9108) is resiliently biased against the proximal portion of recess (9109), therefore further pushing drive bracket (9104) in a proximal direction. At this stage, knife member (340) and staple driver member (350) are in proximal positions, such that stapling head assembly driver (9105) and therefore stapling head assembly (300) are in a non-actuated state.

As drive gear (9114) is rotated by motor drive shaft (9007), this causes drive gear (9014) to travel along the semi-annular array of teeth (9012), thereby rotating rotary member (9113) to the position shown in FIG. 25B. Rotary member (9113) pushes pawl (9108) against the distal portion of recess (9109), thereby actuating drive bracket (9104) and stapling head assembly driver (9105) in a distal direction. Stapling head assembly (300) is thus in an actuated state at the stage shown in FIG. 25B. Torsion spring (9110) has a spring constant strong enough to allow pawl (9108) to push drive bracket (9104) in the distal direction without having pawl (9108) over-rotate around pin (9116), thereby slipping out of recess (9109). In other words, torsion spring (9110) has a large enough spring contact to keep pawl (9108) within recess (9109) while pawl (9108) pushes drive bracket (9104) distally.

After stapling head assembly (300) has been actuated through a full distal drive stroke as shown in the transition from FIG. 25A to FIG. 25B, motor (9101) rotates shaft (9107) and gear (9114) in a reverse direction, thereby pivoting rotary arm (9115) about pin (9111) back to the position shown in FIG. 25A. As rotary arm (9115) pivots back to the position shown in FIG. 25A, pawl (9108) pulls drive bracket (9104) and stapling head assembly driver (9105) proximally back to the position shown in FIG. 25A. The bias imposed by torsion spring (9110) maintains engagement between pawl (9108) and bracket (9104). At this stage, knife member (340) and staple driver member (350) are back to proximal positions, such that stapling head assembly driver (9105) and therefore stapling head assembly (300) is back in a non-actuated state.

In some alternative versions, a resilient member resiliently urges drive bracket (9104) and stapling head assembly driver (9105) proximally, such that motor (9101) is simply deactivated to allow the resilient member to return drive bracket (9104) and stapling head assembly driver (9105) from the position shown in FIG. 25B back to the position shown in FIG. 25A. In such versions, deactivated motor (9101) may allow shaft (9107) to rotate freely. Thus, motor (9101) need not necessarily be reversed in order to return drive bracket (9104) and stapling head assembly driver (9105) from the position shown in FIG. 25B back to the position shown in FIG. 25A. Other suitable ways in which drive bracket (9104) and stapling head assembly driver (9105) may be returned from the position shown in FIG. 25B back to the position shown in FIG. 25A will be apparent to those of ordinary skill in the art in view of the teachings herein.

C. Direct Gear Based Firing and Return System

Figure 26A:
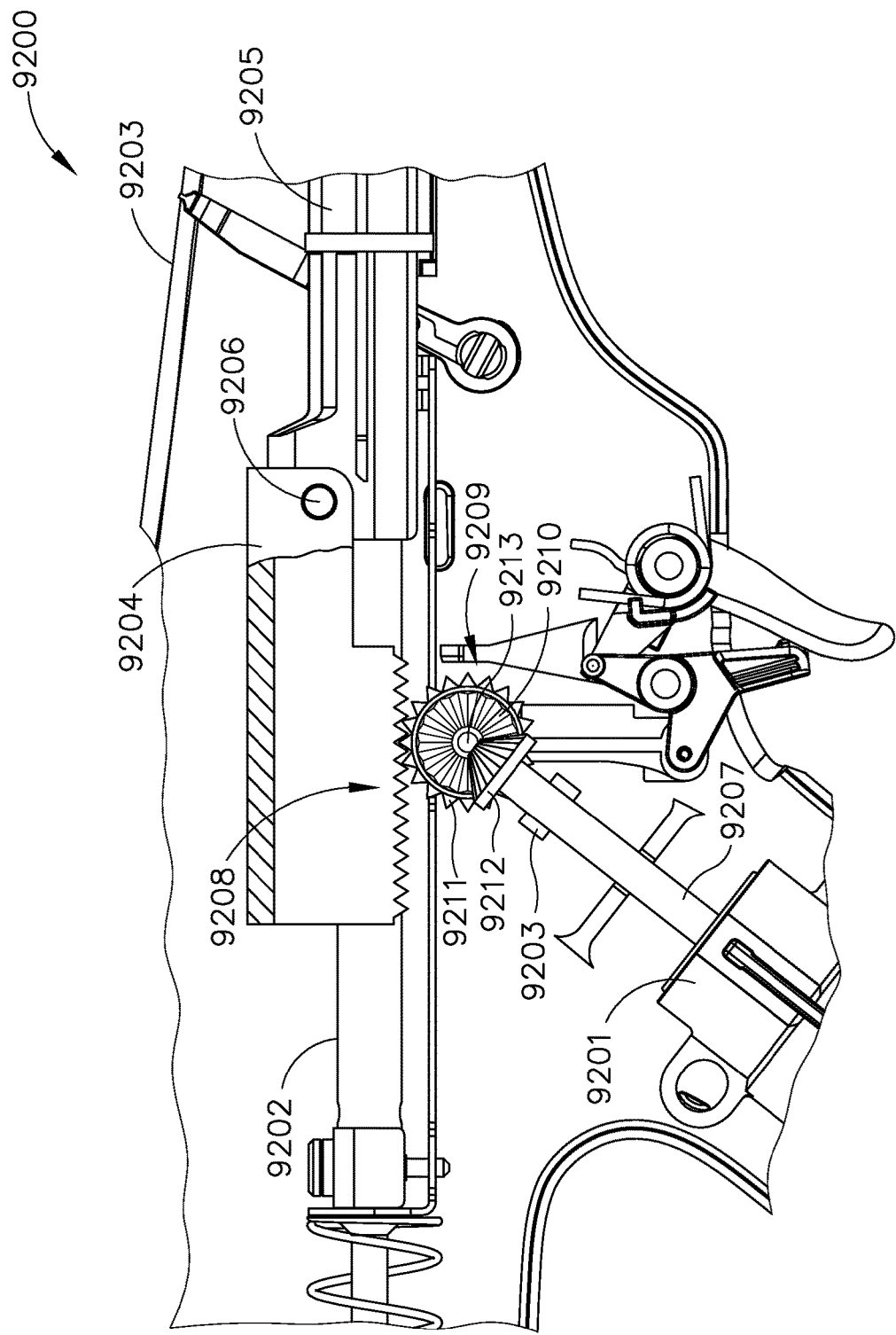
FIG. 26A depicts a partial side elevational view of another alternative stapling head actuation assembly that may be incorporated into the circular stapler of FIG. 1, with a drive bracket in a first linear position.
Figure 26B:
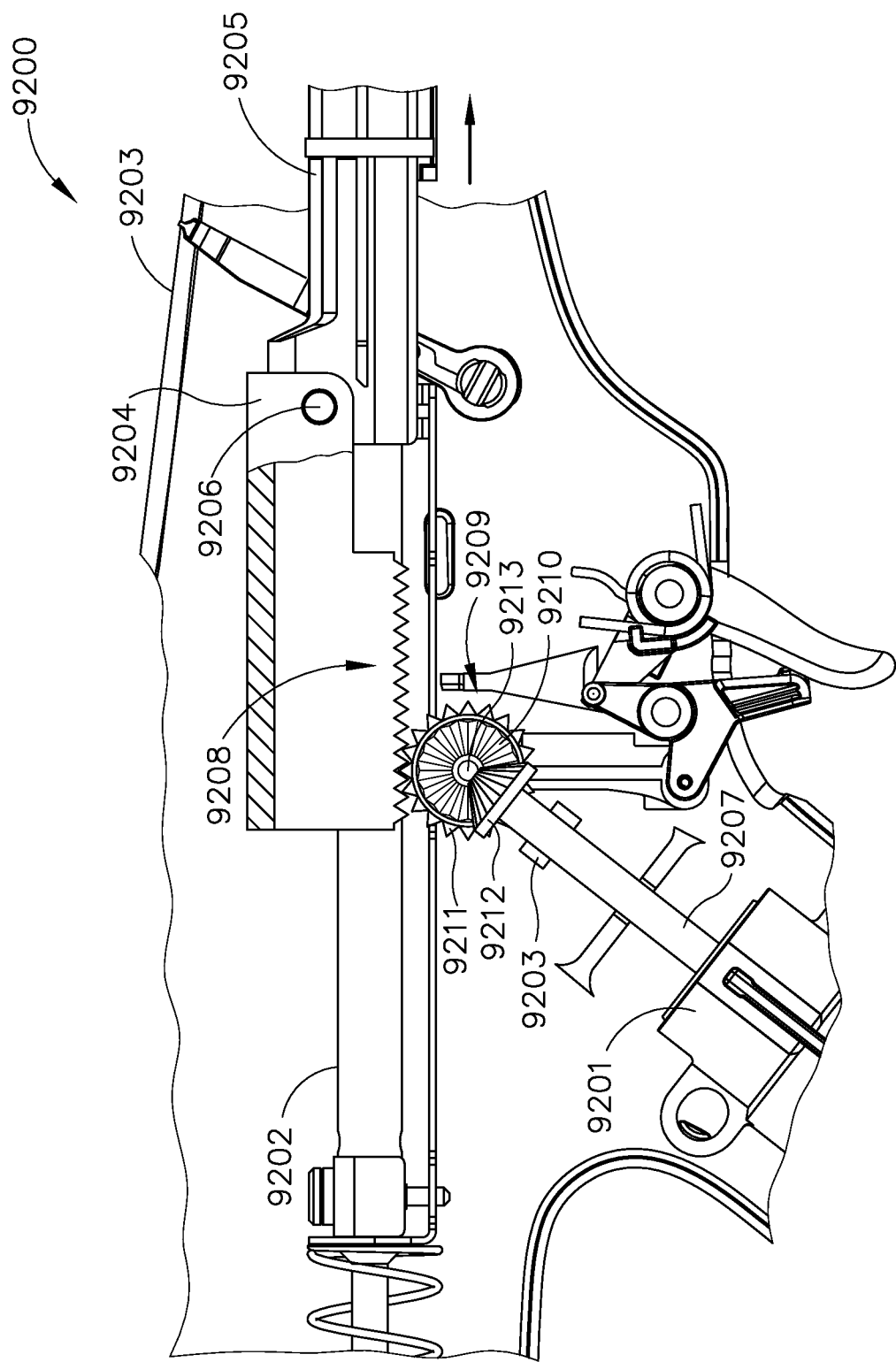
FIG. 26B depicts a partial side elevational view of the stapling head actuation assembly of FIG. 26A, with the drive bracket in a second linear position.
Figure 26C:
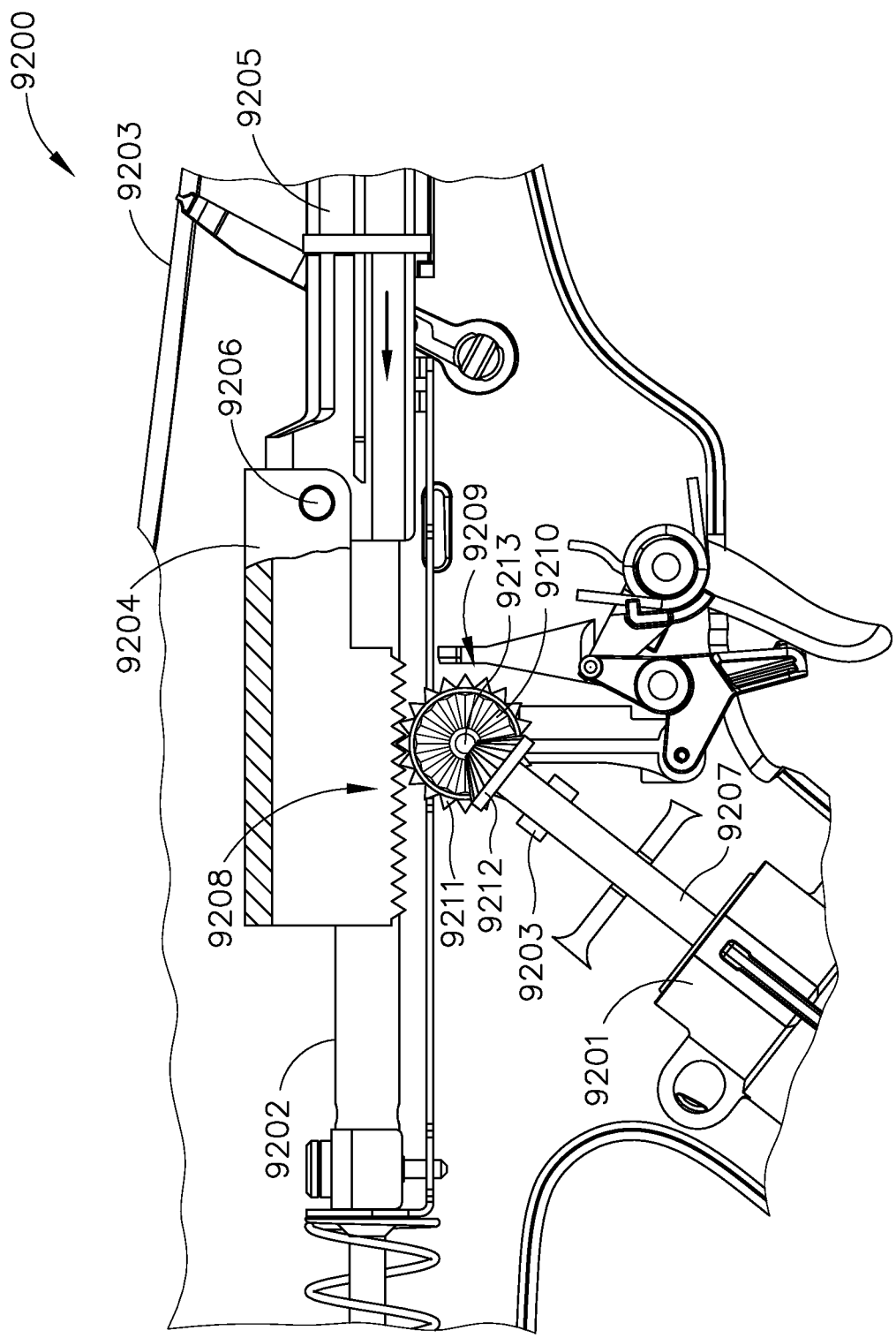
FIG. 26C depicts a partial side elevational view of the stapling head actuation assembly of FIG. 26A, with drive bracket in a third linear position.

FIGS. 26A-26C show various components of another exemplary stapling head actuation assembly (9200) that is operable to actuate stapling head assembly (300). These components include a motor (9201), a motor drive shaft (9207) that is driven by motor (9201), a drive gear assembly (9209), a drive bracket (9204), and a stapling head assembly driver (9205). Motor (9201) is similar to motor (160) described above. In particular, motor (9201) is coupled with motor drive shaft (9207) and is further coupled with a first bevel gear (9212). Therefore, activation of motor (9201) causes rotation of first bevel gear (9212). Various suitable configurations that may be used for motor (9201) will be apparent to those of ordinary skill in the art in view of the teachings herein. In the present example, assembly (9200) lacks a gearbox that is analogous to gearbox (162), though it should be understood that a gearbox and/or any other suitable components may be interposed between motor (9201) and first bevel gear (9212) to provide desired operational characteristics (e.g., torque, speed, etc.).

Drive gear assembly (9209) comprises first bevel gear (9212), a second bevel gear (9210), and a spur gear (9211) extending around the circumference of second bevel gear (9210). First bevel gear (9212) is attached to the distal end of motor drive shaft (9207) and is configured to rotate in two angular directions as determined by motor drive shaft (9207). First bevel gear (9212) and second bevel gear (9210) are connected by complementary teeth in such a way that rotation of first bevel gear (9212) about a first axis drives rotation of second bevel gear (9210) about a second axis that is perpendicular to the first axis. Second bevel gear (9210) is rotatably coupled to pin (9213) which is also fixed to casing (9203). Therefore, while first bevel gear (9212) and second bevel gear (9210) unitarily rotate with each other relative to casing (9203), gears (9212, 9210) are incapable of translating relative to casing (9203). Spur gear (9211) is unitarily fixed to the circumference of second bevel gear (9210). Therefore, spur gear (9211) also rotates in response to first bevel gear (9212). Casing (9203) is substantially similar to casing (110) described above.

Trocar actuation rod (9202) is substantially similar to trocar actuation rod (220) described above. In the present example, trocar actuation rod (9202) is presumed to be located at a position to define a desirable "clinically acceptable range" for gap distance (d). So while trocar actuation rod (9202) is in fact movable, it is assumed to be stationary through the stages shown in FIGS. 26A-26C.

Drive bracket (9204) is substantially similar to drive bracket (250) described above, except that drive bracket (9204) comprises a spur rack (9208). Spur rack (9208) is configured to mate with spur gear (9211) of drive gear assembly (9209) instead of being pivotably coupled to cam follower (600). Therefore, rotation of spur gear (2011) translates drive bracket (9204) longitudinally due to spur gear (2011) driving spur rack (9208). Drive bracket (9204) is fixed to stapling head assembly driver (9205) via pin (9206). However, drive bracket (9204) and stapling head assembly driver (9205) may instead be formed together as a single unitary piece if desired. Stapling head assembly driver (9205) is substantially similar to stapling head assembly driver (240) described above. Therefore, it should be understood that staple driver member (350) will translate longitudinally relative to trocar actuation rod (9202) in response to translation of stapling head assembly driver (9205) and drive bracket (9205) relative to trocar actuation rod (9202).

FIGS. 26A-26C schematically depict the interaction between drive gear assembly (9209), drive bracket (9204), and stapling head assembly driver (9205). It should be understood that the rotation of drive gear assembly (9209) throughout the stages shown in FIGS. 26A-26C is driven by motor (9201).

FIG. 26A shows stapling head actuation assembly (9200) in a first, pre-firing configuration. Spur gear (9211) of drive gear assembly (9209) is located on a distal portion of spur rack (9208) of drive bracket (9204). At this stage, knife member (340) and staple driver member (350) are in proximal positions, such that stapling head assembly driver (9205) and therefore stapling head assembly (300) are in a non-actuated state.

As first bevel gear (9212) is rotated by motor drive shaft (9207) in a first angular direction, this causes second bevel gear (9210) and spur gear (9211) to rotate about pin (9213) in a clockwise direction. Spur gear (9211) translates drive bracket (9204) via spur rack (9208) in a distal direction to the position shown in FIG. 26B. Drive gear assembly (9209) thus drives knife member (340) and staple driver member (350) distally via drive bracket (9204) and stapling head assembly driver (9205). Stapling head assembly (300) is thus in an actuated states at the stage shown in FIG. 23B.

After drive bracket (9204) reaches the position shown in FIG. 26B, first bevel gear (9212) is rotated by motor drive shaft (9207) in reverse in a second angular direction. This reversal causes second bevel gear (9210) and spur gear (9211) to rotate about pin (9213) in a counterclockwise direction. Spur gear (9211) translates drive bracket (9204) via spur rack (9208) in a proximal direction to the position shown in FIG. 26C. At this stage, knife member (340) and staple driver member (350) are back to proximal positions, such that stapling head assembly driver (9205) and therefore stapling head assembly (300) are back in a non-actuated state.

D. Lead Screw Based Firing and Return System

Figure 27A:
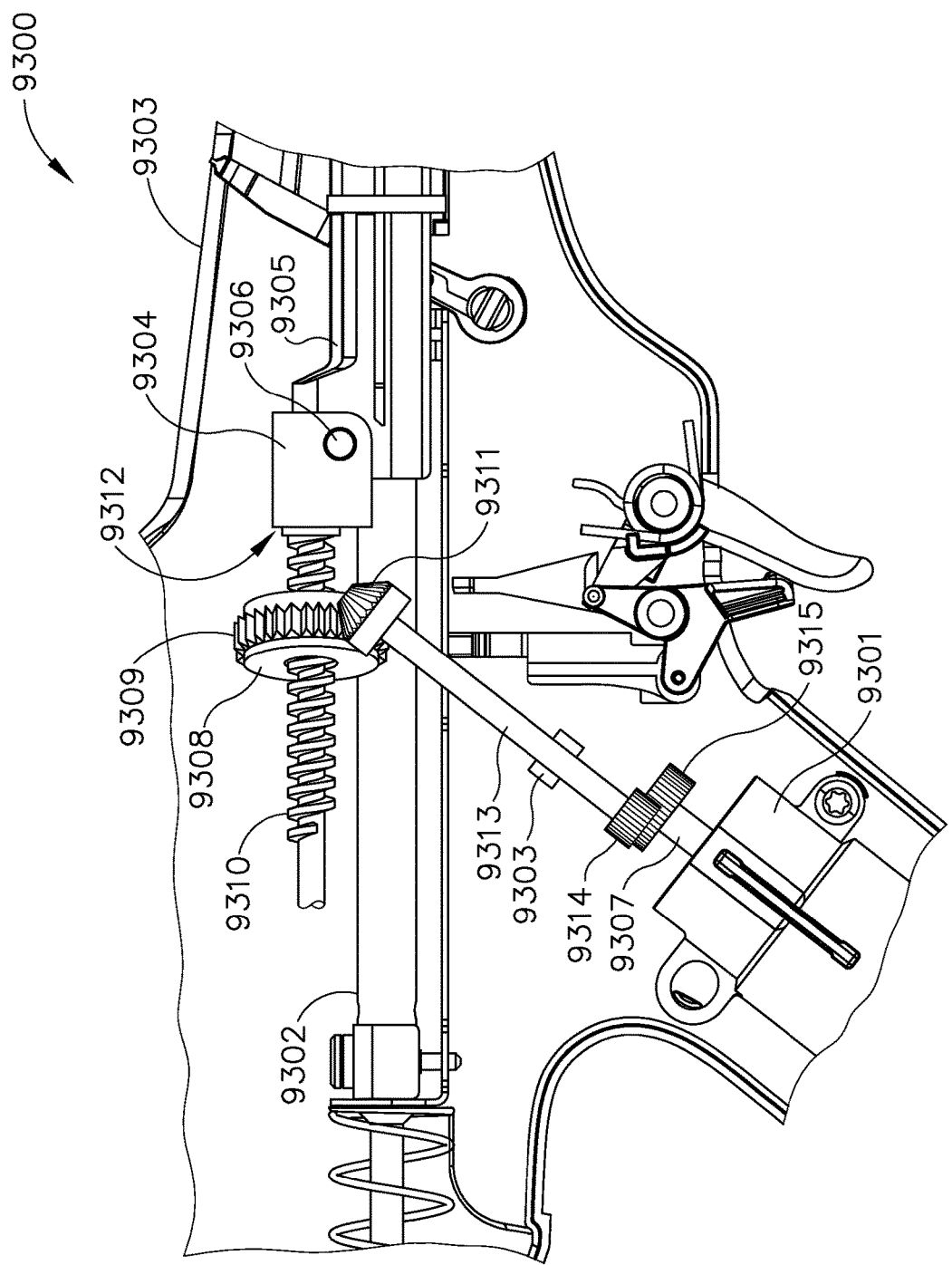
FIG. 27A depicts a partial side elevational view of another alternative stapling head actuation assembly that may be incorporated into the circular stapler of FIG. 1, with a drive bracket in a first linear position.
Figure 27B:
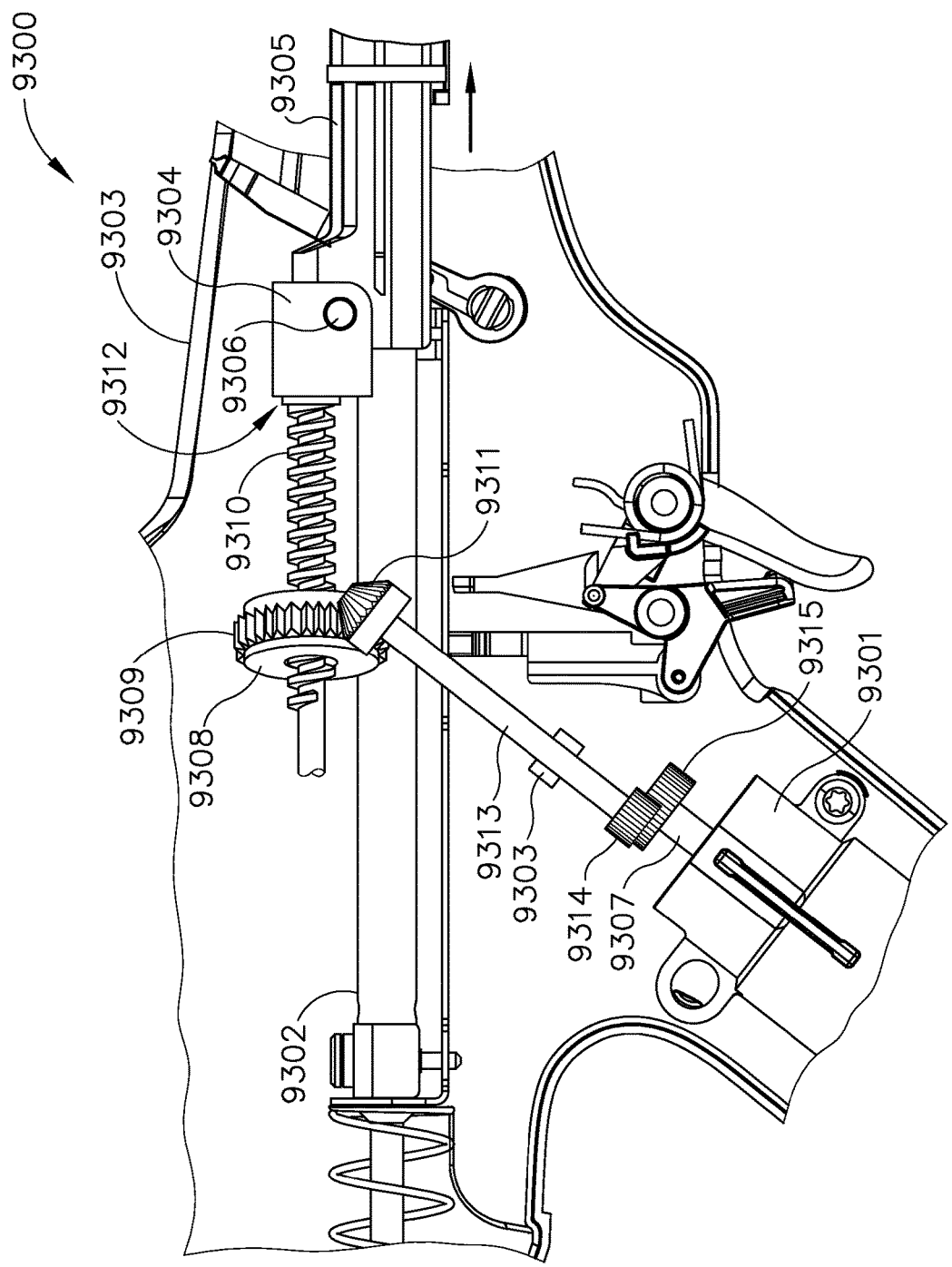
FIG. 27B depicts a partial side elevational view of the stapling head actuation assembly of FIG. 27A, with the drive bracket in a second linear position.
Figure 27C:
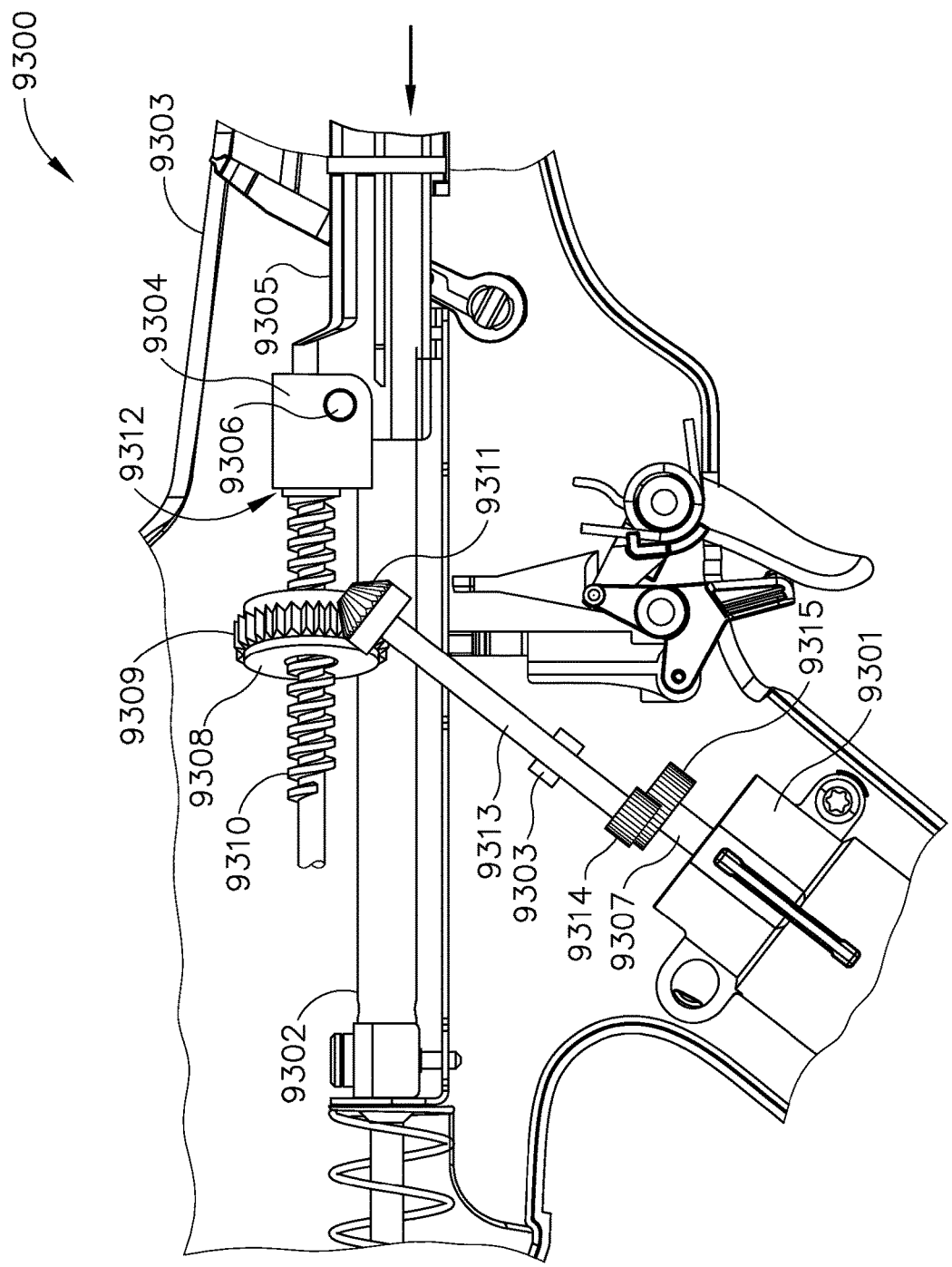
FIG. 27C depicts a partial side elevational view of the stapling head actuation assembly of FIG. 27A, with the drive bracken in a third linear position.

FIGS. 27A-27C show various components of another stapling head actuation assembly (3200) that are operable to actuate stapling head assembly (300). These components include a motor (9301), a motor drive shaft (9307) that is driven by motor (9301), a first spur gear (9315) coupled to the distal end of motor drive shaft (9307), a second spur gear (9214) coupled to the proximal end of an extending shaft (9313), a bevel gear (9311) coupled to the distal end of extending shaft (9313), a third spur gear (9309), a drive nut (9308) with interior threading, a lead screw (9310), a drive bracket (9304), and a stapling head assembly driver (9305).

Motor (9301) is similar to motor (160) described above. In particular, motor (9301) is coupled with motor drive shaft (9307) and is further coupled with spur gear (9315). Therefore, activation of motor (9301) causes rotation of spur gear (9315). Various suitable configurations that may be used for motor (9301) will be apparent to those of ordinary skill in the art in view of the teachings herein. In the present example, assembly (9300) lacks a gearbox that is analogous to gearbox (162), though it should be understood that a gearbox and/or any other suitable components may be interposed between motor (9301) and first bevel gear (9312) to provide desired operational characteristics (e.g., torque, speed, etc.).

Trocar actuation rod (9302) is substantially similar to trocar actuation rod (220) described above. In the present example, trocar actuation rod (9302) is presumed to be located at a position to define a desirable "clinically acceptable range" for gap distance (d). So while trocar actuation rod (9302) is in fact movable, it is assumed to be stationary through the stages shown in FIGS. 26A-26C.

First spur gear (9315) connects with second spur gear (9314) in such a way that rotation of first spur gear (9315)

rotates second spur gear (9314). Second spur gear is fixedly secured to extending shaft (9313). Extending shaft (9313) is rotatably secured to casing (9303). Bevel gear (9311) is fixedly secured to the distal end of extending shaft (9313) so that bevel gear (9311) rotates unitarily with second spur gear (9314). Bevel gear (9311) has teeth that complement the teeth of third spur gear (9309) so that rotation of bevel gear (9311) rotates third spur gear (9309). In some variations, gears (9311, 9309) have meshing helical teeth or threads. It should be understood that gear (9311) rotates about an axis that is obliquely oriented relative to (and laterally offset from) the axis about which gear (9309) rotates. Various suitable ways in which gears (9311, 9309) may be engaged will be apparent to those of ordinary skill in the art in view of the teachings herein.

Third spur gear (9309) encompasses and is fixed to the circumference of drive nut (9308). Drive nut (9308) is rotatably coupled to casing (9303) such that casing (9303) permits drive nut (9308) to rotate within casing (9303) yet permits drive nut (9308) to rotate within casing (9303). Drive nut (9308) comprises internal threading that mates with external threading of lead screw (9310). Lead screw (9310) is permitted to translate within casing (9303) but is prevented from rotating in casing (9303). Lead screw (9310) translates longitudinally in response to rotation of drive nut (9308).

Drive bracket (9304) is substantially similar to drive bracket (250) described above, except that the proximal end of drive bracket (9304) is fixedly secured to lead screw (9310) instead of being pivotably coupled to cam follower (600). Thus, rotation of drive nut (9308) translates drive bracket (9204) longitudinally due to internal threading of drive nut (9308) driving lead screw (9310), which is fixed to proximal end (9312) of drive bracket (9204). Drive bracket (9304) is fixed to stapling head assembly driver (9305) via pin (9306). However, drive bracket (9304) and stapling head assembly driver (9305) may instead be formed together as a single unitary piece if desired. Stapling head assembly driver (9305) is substantially similar to stapling head assembly driver (240) described above. Therefore, it should be understood that staple driver member (350) will translate longitudinally relative to trocar actuation rod (9302) in response to translation of stapling head assembly driver (9305) and drive bracket (9305) relative to trocar actuation rod (9302).

FIGS. 27A-27C schematically depict the interaction between motor drive shaft (9307), first spur gear (9315), second spur gear (9314), extending shaft (9313), bevel gear (9311), third spur gear (9309), drive nut (9308), lead screw (9310), drive bracket (9304) and stapling head assembly driver (9305). It should be understood that the rotation of first spur gear (9315) throughout the stages shown in FIGS. 27A-27C is driven by a motor similar to motor (160) and gearbox (9301).

FIG. 27A shows stapling head actuation assembly (9300) in a first, pre-firing configuration. Drive nut (9308) is located at a distal position along lead screw (9310), thereby holding drive bracket (9304) in a proximal position. At this stage, knife member (340) and staple driver member (350) are in proximal positions, such that stapling head assembly driver (9305) and therefore stapling head assembly (300) are in a non-actuated state.

As first spur gear (9315) is rotated by motor drive shaft (9307) in a first angular direction, this causes second spur gear (9314), extending shaft (9313) and bevel gear (9311) to rotate in a second (opposite) direction. Bevel gear (9311) engages spur gear (9309) to rotate spur gear (9311). Spur gear (9311) drives drive nut (9308) to rotate. Internal threading of drive nut (9308) then drives lead screw (9310) in a distal direction. Lead screw (9310) translates drive bracket (9304) in a distal direction to the position shown in FIG. 27B. Motor (9301) thus drives knife member (340) and staple driver member (350) distally via drive bracket (9304) and stapling head assembly driver (9305). Stapling head assembly (300) is thus in an actuated state at the stage shown in FIG. 27B.

After drive bracket (9304) reaches the position shown in FIG. 27B, first spur gear (9315) is rotated by motor drive shaft (9307) in reverse to a second angular direction. This reversal causes second spur gear (9314), extending shaft (9313), and bevel gear (9311) to rotate in a reverse direction. Bevel gear (9311) engages spur gear (9309) to rotate spur gear (9211) in reverse. Spur gear (9311) drives drive nut (9308) to rotate in reverse. Internal threading of drive nut (9308) then drives lead screw (9310) in a proximal direction. Lead screw (9310) translates drive bracket (9304) back in a proximal direction to the position shown in FIG. 27C. At this stage, knife member (340) and staple driver member (350) are back to proximal positions, such that stapling head assembly driver (9205) and therefore stapling head assembly (300) are back in a non-actuated state.

III. Circular Stapler with Rotatable Shaft

In some instances, it may be desirable to rotate a shaft (9502) relative to a handle assembly (9503) of a circular stapler (9500). In particular, it may be desirable from an ergonomic standpoint to enable an operator to rotate shaft (9502) relative to handle assembly (9503), particularly when shaft (9502) includes a preformed bend. This may enable the operator to more easily position a stapling head assembly (9530) in relation to handle assembly (9503). Such rotatability thus might benefit an operator by limiting arm or hard motion required of the operator in order to place circular stapler (9500) in the proper location or orientation required to fire circular stapler (9500).

Figure 28:
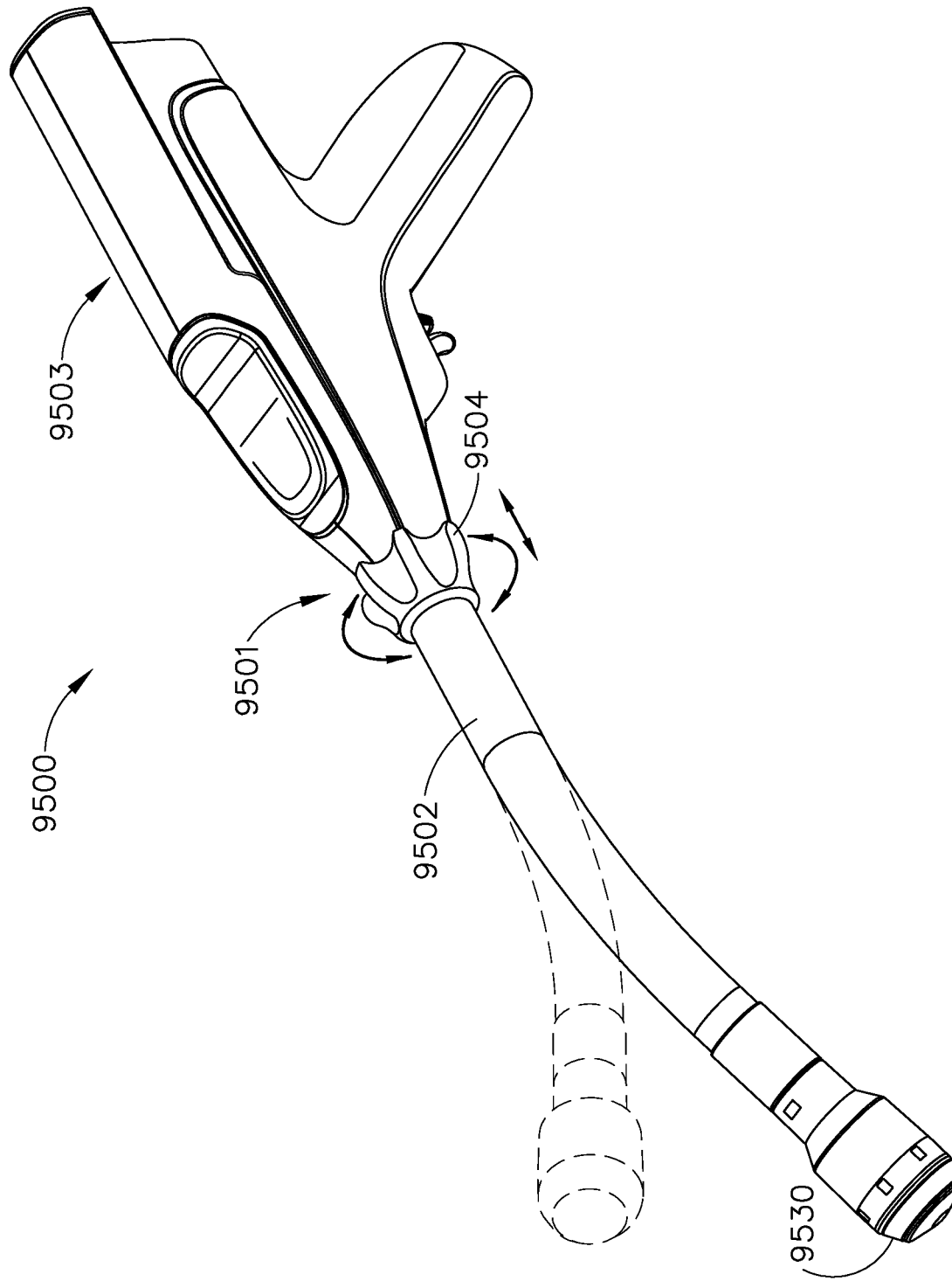
FIG. 28 depicts a perspective view of a circular stapler where the distal end of the shaft assembly is rotatable relative to the casing.

FIG. 28 depicts circular stapler (9500) with handle assembly (9503), shaft (9502), and a rotator knob (9501) configured to rotate shaft (9502) relative to handle assembly (9503). Rotator knob (9501) comprises an array of gripping features (9504) that are configured to be gripped by user.

Figure 29:
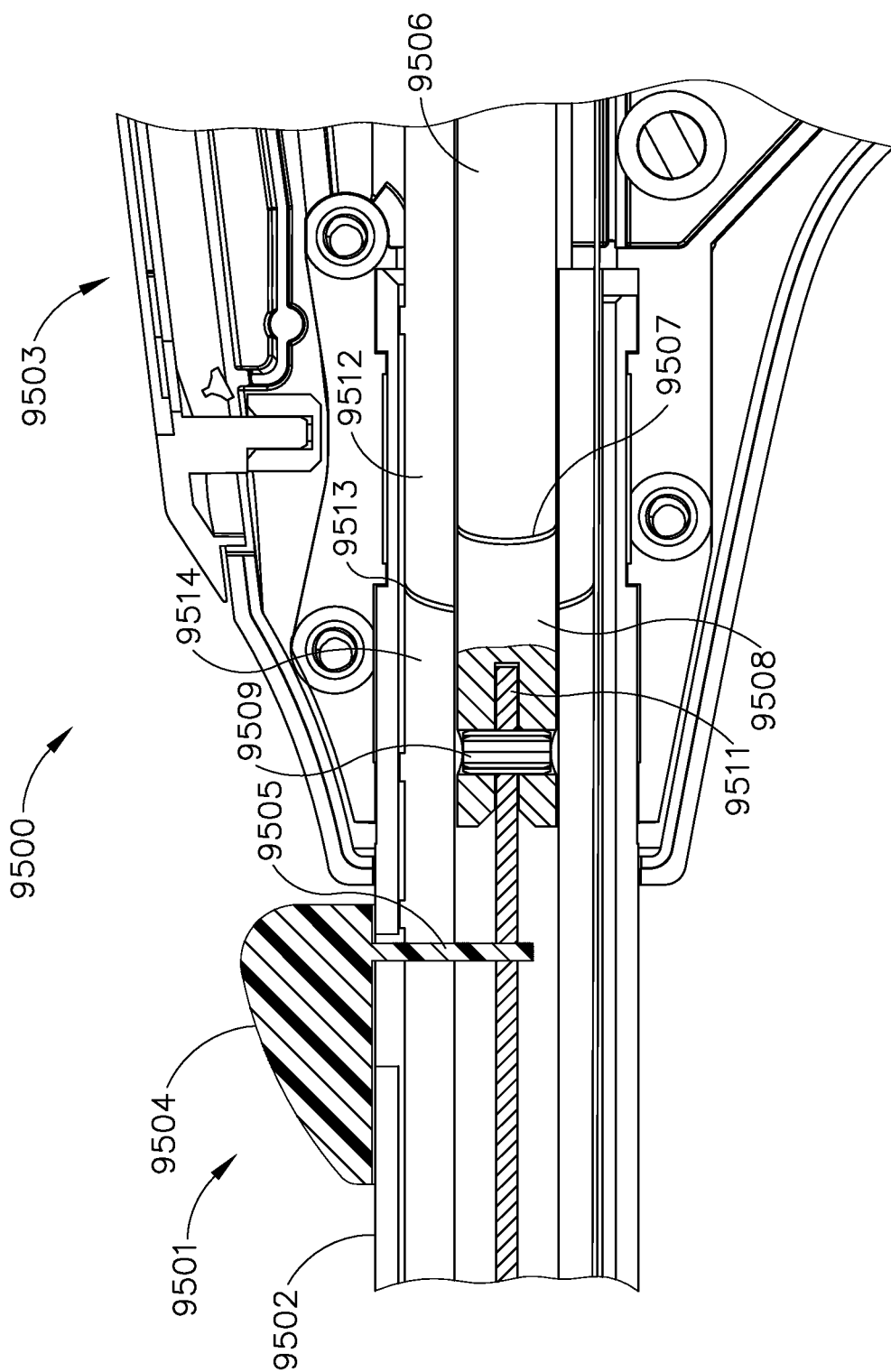
FIG. 29 depicts a side cross-sectional view of the circular stapler of FIG. 28.

FIG. 29 depicts a cross-sectional view of rotator knob (9501) slidably attached to rotatable shaft (9502) in such a way that rotator knob (9501) can translate along shaft (9502) and rotate shaft (9502) about the longitudinal axis. A trocar actuation band (9511) is unitarily fixed to distal end of trocar actuation rod (9508) by trocar band holder (9509) in such a way that trocar actuation band (9511) rotates and translates with distal trocar actuation rod (9508). Proximal trocar actuation rod (9506) is within handle assembly (9503) and terminates at trocar actuation rod ball joint (9507). Trocar actuation rod ball joint (9507) rotatably connects proximal trocar actuation rod (9506) with distal trocar actuation rod (9508).

Similarly, proximal end stapling head assembly driver (9512) is within handle assembly (9503) and terminates at stapling head assembly driver ball joint (9513). Stapling head assembly driver ball joint (9513) rotatably connects proximal stapling head assembly driver (9512) and distal end stapling head assembly driver (9514).

Rotator knob (9501) comprises grip (9504) and strip (9505) unitarily coupled to grip (9504). Strip (9505) extends into both distal end stapling head assembly driver (9514) and trocar actuation band (9511). Therefore, when rotator knob (9501) rotates about shaft (9502), strip (9505) causes trocar actuation band (9511), trocar band holder (9509), distal trocar actuation rod (9508), and distal stapling head assembly driver (9514) to unitarily rotate relative to proximal end stapling head assembly driver (9512) and proximal trocar actuation rod (9506) due to ball joints (9507, 9513). Since rotator knob (9501) is slidably connected to rotatable shaft (9502), trocar actuation band (9511), trocar band holder (9509), distal trocar actuation rod (9508), and distal stapling head assembly driver (9514) are also able to translate relative to rotatable shaft (9502). Of course, any other means known in the art in view of the teachings herein may be utilized to rotate rotatable shaft (9502). It should also be understood that one or more features may be provided to selectively lock the angular position of shaft (9502) relative to handle assembly (5503).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a body, (b) a shaft assembly extending distally from the body, wherein the shaft assembly comprises an actuator; (c) a stapling head assembly located at the distal end of the shaft assembly, wherein the stapling head assembly is operable to drive an annularly arranged array of staples into tissue in response to translation of the actuator along a first axis relative to the body; and (d) a drive assembly coupled with the actuator, wherein the drive assembly is operable to translate the actuator along the first axis relative to the body, wherein the drive assembly comprises: (i) a first rotary member, wherein the first rotary member is rotatable about a second axis, wherein the second axis is non-parallel with the first axis, and (ii) a second rotary member, wherein the second rotary member is rotatable about a third axis, wherein the third axis is non-parallel with the first axis, wherein the third axis is non-parallel with the second axis, wherein the first rotary member is operable to drive the second rotary member to rotate about the third axis to thereby drive the actuator along the first axis relative to the body.

Example 2

The surgical instrument of Example 1, wherein the drive assembly further comprises a motor disposed within the body, wherein the motor is operable to drive the first rotary member about the second axis.

Example 3

The surgical instrument of any one or more of Examples 1 through 2, wherein the first rotary member comprises a first gear having teeth.

Example 4

The surgical instrument of Example 3, wherein the second rotary member comprises a second gear having teeth.

Example 5

The surgical instrument of Example 4, wherein the teeth of the second gear extend along a plane in an arcuate arrangement.

Example 6

The surgical instrument of any one or more of Examples 1 through 5, wherein the drive assembly further comprises a link, wherein a first end of the link is pivotably coupled with the second rotary member, wherein a second end of the link is pivotably coupled with the actuator.

Example 7

The surgical instrument of Example 6, wherein the second rotary member includes an outwardly projecting arm, wherein the first end of the link is pivotably coupled with the second rotary member via the outwardly projecting arm.

Example 8

The surgical instrument of any one or more of Examples 6 through 7, wherein the second rotary member is coupled with the body via a first pin, wherein the first end of the link is pivotably coupled with the second rotary member via a second pin, wherein the second end of the link is pivotably coupled with the actuator via a third pin.

Example 9

The surgical instrument of Example 8, wherein the drive assembly is configured to position the first, second, and third pins along a single axis to thereby translate the actuator to a distal-most position.

Example 10

The surgical instrument of any one or more of Examples 8 through 9, wherein the single axis is parallel with the first axis.

Example 11

The surgical instrument of any one or more of Examples 1 through 10, wherein the first rotary member is rotatable through a first range of motion in a first angular direction to drive the actuator distally along the first axis relative to the body, wherein the first rotary member is rotatable through a second range of motion in the first angular direction to drive the actuator proximally along the first axis relative to the body.

Example 12

The surgical instrument of Example 11, wherein the second rotary member is operable to push the actuator distally in response to rotation of the first rotary member through the first range of motion, wherein the second rotary member is operable to pull the actuator distally in response to rotation of the first rotary member through the second range of motion.

Example 13

The surgical instrument of any one or more of Examples 1 through 12, wherein the second axis is obliquely oriented relative to the first axis.

Example 14

The surgical instrument of any one or more of Examples 1 through 13, wherein the third axis is perpendicular to the first axis.

Example 15

The surgical instrument of any one or more of Examples 1 through 14, wherein the second axis is obliquely oriented relative to the third axis.

Example 16

The surgical instrument of any one or more of Examples 1 through 15, wherein the drive assembly further comprises an idler gear, wherein the idler gear is configured to communicate rotation of the first rotary member to the second rotary member.

Example 17

A surgical instrument comprising: (a) a body, (b) a shaft assembly extending distally from the body, wherein the shaft assembly comprises an actuator; (c) a stapling head assembly located at the distal end of the shaft assembly, wherein the stapling head assembly is operable to drive an annularly arranged array of staples into tissue in response to translation of the actuator along a first axis relative to the body; and (d) a drive assembly coupled with the actuator, wherein the drive assembly is operable to translate the actuator along the first axis relative to the body, wherein the drive assembly comprises: (i) a gear, wherein the gear is rotatable about a second axis, wherein the second axis is non-parallel with the first axis, and (ii) a rotary member, wherein the rotary member is rotatable about a third axis, wherein the third axis is non-parallel with the first axis, wherein the third axis is non-parallel with the second axis, wherein the rotary member includes a set of teeth positioned along a plane in an arcuate array, wherein the teeth of the rotary member are engaged with the gear such that the gear is operable to drive the rotary member to rotate about the third axis to thereby drive the actuator along the first axis relative to the body.

Example 18

The surgical instrument of Example 17, wherein the drive assembly further comprises a link, wherein a first end of the link is pivotably coupled with the rotary member, wherein a second end of the link is pivotably coupled with the actuator, wherein the rotary member and the link are configured to transition between the following states: (A) a first collapsed configuration, wherein the actuator is configured to be in a proximal position in response to the rotary member and the link being in the first collapsed configuration, (B) a straight configuration, wherein the actuator is configured to be in a distal position in response to the rotary member and the link being in the straight configuration, and (C) a second collapsed configuration, wherein the actuator is configured to be in the proximal position in response to the rotary member and the link being in the second collapsed configuration.

Example 19

The surgical instrument of Example 18, wherein the rotary member is rotatable through a first range of motion in a first direction to transition the rotary member and the link from the first collapsed configuration to the straight configuration, wherein the rotary member is further rotatable through a second range of motion in the first direction to transition the rotary member and the link from the straight configuration to the second collapsed configuration.

Example 20

A surgical instrument comprising: (a) a body, (b) a shaft assembly extending distally from the body, wherein the shaft assembly comprises an actuator; (c) a stapling head assembly located at the distal end of the shaft assembly, wherein the stapling head assembly is operable to drive an annularly arranged array of staples into tissue in response to translation of the actuator along a first axis relative to the body; and (d) a drive assembly coupled with the actuator, wherein the drive assembly is operable to translate the actuator along the first axis relative to the body, wherein the drive assembly comprises: (i) a gear, wherein the gear is rotatable about a second axis, wherein the second axis is non-parallel with the first axis, and (ii) a rotary member, wherein the rotary member is rotatable about a third axis, wherein the third axis is non-parallel with the first axis, wherein the third axis is non-parallel with the second axis, wherein the rotary member extends along a plane, wherein the rotary member is rotatable along the plane such that the third axis is perpendicular to the plane, wherein the gear is laterally offset from the plane.

V. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may be readily combined with one or more teachings of U.S. Pat. No. 7,794,475, entitled "Surgical Staples Having Compressible or Crushable Members for Securing Tissue Therein and Stapling Instruments for Deploying the Same," issued Sep. 14, 2010, the disclosure of which is incorporated by reference herein; U.S. Pub. No. 2014/0151429, entitled "Trans-Oral Circular Anvil Introduction System with Dilation Feature," published Jun. 5, 2014, issued as U.S. Pat. No. 9,572,573 on Feb. 21, 2017, the disclosure of which is incorporated by reference herein; U.S. Pub. No. 2014/0144968, entitled "Surgical Staple with Integral Pledget for Tip Deflection," published May 29, 2014, issued as U.S. Pat. No.

9,289,207 on Mar. 22, 2016, the disclosure of which is incorporated by reference herein; U.S. Pub. No. 2014/0158747, entitled "Surgical Stapler with Varying Staple Widths along Different Circumferences," published Jun. 12, 2014, now abandoned, the disclosure of which is incorporated by reference herein; U.S. Pub. No. 2014/0144969, entitled "Pivoting Anvil for Surgical Circular Stapler," published May 29, 2014, issued as U.S. Pat. No. 9,498,222 on Nov. 22, 2016, the disclosure of which is incorporated by reference herein; U.S. Pub. No. 2014/0151430, entitled "Circular Anvil Introduction System with Alignment Feature," published Jun. 5, 2014, issued as U.S. Pat. No. 9,724,100 on Aug. 8, 2017, the disclosure of which is incorporated by reference herein; U.S. Pub. No. 2014/0166717, entitled "Circular Stapler with Selectable Motorized and Manual Control, Including a Control Ring," published Jun. 19, 2014, issued as U.S. Pat. No. 9,532,783 on Jan. 3, 2017, the disclosure of which is incorporated by reference herein; U.S. Pub. No. 2014/0166728, entitled "Motor Driven Rotary Input Circular Stapler with Modular End Effector," published Jun. 19, 2014, issued as U.S. Pat. No. 9,597,081 on Mar. 21, 2017, the disclosure of which is incorporated by reference herein; and/or U.S. Pub. No. 2014/0166718, entitled "Motor Driven Rotary Input Circular Stapler with Lockable Flexible Shaft," published Jun. 19, 2014, issued as U.S. Pat. No. 9,463,022 issued on Oct. 11, 2016, the disclosure of which is incorporated by reference herein. Various suitable ways in which such teachings may be combined will be apparent to those of ordinary skill in the art.

While the examples herein have been provided in the context of a circular stapling instrument, it should be understood that the various teachings herein may be readily applied to various other kinds of surgical instruments. By way of example only, the various teachings herein may be readily applied to linear stapling devices (e.g., endocutters). For instance, various teachings herein may be readily combined with various teachings of U.S. Pub. No. 2012/0239012, entitled "Motor-Driven Surgical Cutting Instrument with Electric Actuator Directional Control Assembly," published Sep. 20, 2012, issued as U.S. Pat. No. 8,453,914 on Jun. 4, 2013, the disclosure of which is incorporated by reference herein, and/or U.S. Pub. No. 2010/0264193, entitled "Surgical Stapling Instrument with An Articulatable End Effector," published Oct. 21, 2010, issued as U.S. Pat. No. 8,408,439 on Apr. 2, 2013, the disclosure of which is incorporated by reference herein, as will be apparent to those of ordinary skill in the art. As another merely illustrative example, the various teachings herein may be readily applied to a motorized electrosurgical device. For instance, various teachings herein may be readily combined with various teachings of U.S. Pub. No. 2012/0116379, entitled "Motor Driven Electrosurgical Device with Mechanical and Electrical Feedback," published May 10, 2012, issued as U.S. Pat. No. 9,161,803 on Oct. 20, 2015, the disclosure of which is incorporated by reference herein, as will be apparent to those of ordinary skill in the art. Other suitable kinds of instruments in which the teachings herein may be applied, and various ways in which the teachings herein may be applied to such instruments, will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of firing a surgical instrument with a motor by driving translation of an actuator along a first axis, wherein the actuator is operable to actuate a staple driver to drive an annularly arranged array of staples into tissue in response to translation of the actuator along the first axis in a first linear direction, the method comprising:

(a) rotating a first rotary member about a second axis through a first range of motion in a first angular direction such that the first rotary member drives translation of the actuator along the first axis in the first linear direction, wherein the first rotary member comprises a cam member coupled to the motor, wherein rotating the first rotary member through the first range of motion further comprises driving a cam follower with the cam member to rotate the cam follower about a third axis in a second angular direction; and (b) rotating the first rotary member through a second range of motion in the first angular direction subsequent to rotating through the first range of motion in the first angular direction, wherein rotating through the second range of motion comprises driving rotation of the first rotary member about the second axis such that the first rotary member drives translation of the actuator along the first axis in a second linear direction, wherein the second linear direction is opposite relative to the first linear direction.

2. The method of claim 1, wherein rotating through the second range of motion further comprises activating a kill switch, wherein activating the kill switch prevents the motor from further rotation.

3. The method of claim 1, wherein rotating through the second range of motion further comprises the cam member driving the cam follower about the third axis in a third angular direction, wherein the third angular direction is opposite the second angular direction.

4. The method of claim 3, wherein the cam member comprises a first cam feature, wherein the cam follower comprises a first bearing feature, wherein rotating through the first range of motion further comprises the first cam feature bearing against the first bearing feature.

5. The method of claim 4, wherein the cam member comprises a second cam feature, wherein the cam follower comprises a second bearing feature, wherein rotating through the second range of motion further comprises the second cam feature bearing against the second bearing feature.

6. The method of claim 1, wherein the cam follower is pivotably coupled with the actuator, wherein rotating through the first range of motion further comprises the cam follower pivoting relative to the actuator.

7. The method of claim 6, wherein rotating through the second range of motion further comprises the cam follower pivoting relative to the actuator.

8. The method of claim 1, further comprising a body housing the motor and the actuator, wherein rotating the first angular direction comprises translating the actuator relative to the body.

9. The method of claim 8, wherein rotating in the first angular direction comprises rotating relative to the body.

10. A method of firing a surgical instrument with a motor by driving translation of an actuator along a first axis, wherein the actuator is operable to actuate a staple driver to drive an annularly arranged array of staples into tissue in response to translation of the actuator along the first axis in a first linear direction, the method comprising:

(a) rotating through a first range of motion in a first angular direction, wherein rotating through the first range of motion comprises:

(i) driving a first rotary member about a second axis, wherein the first rotary member is operatively engaged with a second rotary member, wherein the first rotary member comprises a cam member fixed to a drive shaft of the motor, and (ii) driving the second rotary member about a third axis in a second angular direction, wherein the second rotary member is pivotably coupled with the actuator such that rotation of the second rotary member about the third axis in the second angular direction drives translation of the actuator along the first axis in the first linear direction, wherein the second rotary member comprises a cam follower pivotable relative to a body of the surgical instrument, wherein rotating through the first range of motion further comprises driving the cam follower in a second angular direction with the cam member; and (b) rotating through a second range of motion in the first angular direction subsequent to rotating through the first range of motion in the first angular direction, wherein rotating through the second range of motion comprises:

(i) driving the first rotary member about the second axis, and (ii) driving the second rotary member about the third axis in a third angular direction such that rotation of the second rotary member about the third axis in the third angular direction drives translation of the actuator along the first axis in a second linear direction.

11. The method of claim 10, cam follower is pivotably coupled to the body of the surgical instrument.

12. The method of claim 10, wherein rotating through the second range of motion further comprises the cam member driving the cam follower in the third angular direction.

13. A method of firing a surgical instrument with a motor by driving translation of an actuator along a first axis, wherein the actuator is operable to actuate a staple driver to drive an annularly arranged array of staples into tissue in response to translation of the actuator along the first axis in a first linear direction, the method comprising:

(a) rotating through a first range of motion in a first angular direction, wherein rotating through the first range of motion comprises driving rotation of a first rotary member about a second axis such that the first rotary member pivots a follower in a first follower direction about a third axis to thereby drive translation of the actuator along the first axis in the first linear direction thereby actuating the staple driver to drive the annularly arranged array of staples into tissue, wherein the second axis extends in a non-parallel orientation relative to the first axis, wherein the follower is pivotable relative to a housing, wherein the first rotary member comprises a cam, wherein the follower comprises a cam follower pivotably coupled with the housing; and (b) rotating through a second range of motion in the first angular direction, wherein rotating through the second range of motion comprises driving rotation of the first rotary member about the second axis such that the first rotary member pivots the follower in a second follower direction about the third axis to thereby drive translation of the actuator along the first axis in a second linear direction thereby retracting the staple driver away from the annularly arranged array of staples, wherein the second linear direction is opposite relative to the first linear direction.

14. The method of claim 13, wherein the third axis is fixed relative to the housing.

* * * * *